(12) United States Patent
Wengner

(10) Patent No.: US 11,690,911 B2
(45) Date of Patent: Jul. 4, 2023

(54) COMBINATION OF ATR KINASE INHIBITORS AND PD-1/PD-L1 INHIBITORS

(71) Applicants: Bayer Pharma Aktiengesellschaft, Berlin (DE); Bayer Aktiengesellschaft, Leverkusen (DE)

(72) Inventor: Antje Margret Wengner, Berlin (DE)

(73) Assignees: Bayer Aktiengesellschaft, Berlin (DE); Bayer Pharma Aktiengesellschaft, Leverkusen (DE)

( * ) Notice: Subject to any disclaimer, the term of this patent is extended or adjusted under 35 U.S.C. 154(b) by 398 days.

(21) Appl. No.: 16/635,812

(22) PCT Filed: Jul. 31, 2018

(86) PCT No.: PCT/EP2018/070729
§ 371 (c)(1),
(2) Date: Jan. 31, 2020

(87) PCT Pub. No.: WO2019/025440
PCT Pub. Date: Feb. 7, 2019

(65) Prior Publication Data
US 2021/0128723 A1    May 6, 2021

(30) Foreign Application Priority Data
Aug. 4, 2017   (EP) .................................... 17184950

(51) Int. Cl.
*A61K 39/395*       (2006.01)
*A61P 35/00*        (2006.01)
(Continued)

(52) U.S. Cl.
CPC ........ *A61K 39/3955* (2013.01); *A61K 31/497* (2013.01); *A61K 31/519* (2013.01);
(Continued)

(58) Field of Classification Search
None
See application file for complete search history.

(56) References Cited

U.S. PATENT DOCUMENTS 9,549,932 B2    1/2017  Wortmann et al.
9,993,484 B2    6/2018  Wortmann et al.
(Continued)

FOREIGN PATENT DOCUMENTS

WO   WO-2016020320 A1 *  2/2016  ......... A61K 31/5377
WO   WO2016020320 A1     2/2016
(Continued)

OTHER PUBLICATIONS

Sundar R, Brown J, Ingles Russo A, Yap TA. Targeting ATR in cancer medicine. Curr Probl Cancer. Jul.-Aug. 2017;41(4):302-315 (Year: 2017).*

(Continued)

*Primary Examiner* — Scarlett Y Goon
*Assistant Examiner* — Miles Joseph Delahoussaye

(57) ABSTRACT

The present invention covers combinations of at least two components, component A and component B, comprising component A being an inhibitor of ATR kinase, particularly an inhibitor of ATR kinase selected from VX-803, VX-970, AZD-6738, a compound of general formula (I) described herein, a compound of general formula (Ib) described herein and Compound A described infra, and component B being a PD-1/PD-L1 inhibitor described herein. Another aspect of the present invention covers the use of such combinations as described herein for the preparation of a medicament for the treatment or prophylaxis of a disease, particularly for the treatment of a hyper-proliferative disease.

15 Claims, 7 Drawing Sheets

(51) Int. Cl.
    *A61K 31/497* (2006.01)
    *A61K 31/519* (2006.01)
    *A61K 31/5377* (2006.01)
    *A61K 39/00* (2006.01)

(52) U.S. Cl.
    CPC .......... *A61K 31/5377* (2013.01); *A61P 35/00* (2018.01); *A61K 2039/505* (2013.01)

(56) References Cited

U.S. PATENT DOCUMENTS

| | | |
|---|---|---|
| 10,729,680 B2 | 8/2020 | Lücking et al. |
| 10,772,893 B2 | 9/2020 | Wortmann et al. |
| 2016/0287604 A1 | 10/2016 | Wortmann et al. |
| 2017/0216304 A1 | 8/2017 | Wortmann et al. |
| 2018/0256591 A1 | 9/2018 | Wortmann et al. |
| 2019/0142812 A1 | 5/2019 | Lücking et al. |
| 2020/0016283 A1 | 1/2020 | Cuthbertson |
| 2020/0063212 A1 | 2/2020 | Wengner et al. |
| 2020/0375997 A1 | 12/2020 | Wengner et al. |
| 2020/0383991 A1 | 12/2020 | Wortmann et al. |
| 2021/0128572 A1 | 5/2021 | Wengner et al. |
| 2021/0128723 A1 | 5/2021 | Wengner |
| 2021/0253573 A1 | 8/2021 | Platzek et al. |
| 2021/0369724 A1 | 12/2021 | Wengner et al. |
| 2022/0117973 A1 | 4/2022 | Krickau et al. |

FOREIGN PATENT DOCUMENTS

| | | |
|---|---|---|
| WO | WO2017106556 A1 | 6/2017 |
| WO | WO2017121684 A1 | 7/2017 |

OTHER PUBLICATIONS

Yap, T. A. et al. (2016). "Exploiting Genomic Instability as a Target," European Journal of Cancer 69(1): S2.

International Search Report dated Oct. 8, 2018 for PCT Application No. PCT/EP2018/070729 filed Jul. 31, 2018, 3 pages.

\* cited by examiner

COMBINATION OF ATR KINASE INHIBITORS AND PD-1/PD-L1 INHIBITORS

CROSS REFERENCE TO RELATED APPLICATIONS

This application is a national stage application under 35 U.S.C. § 371 of International Application No. PCT/EP2018/070729, filed internationally on Jul. 31, 2018, which claims the benefit of priority to European Application No. 17184950.8, filed Aug. 4, 2017.

The present invention covers combinations of at least two components, component A and component B, comprising component A being an inhibitor of ATR kinase, particularly an inhibitor of ATR kinase selected from VX-803, VX-970, AZD-6738, a compound of general formula (I) described infra, a compound of general formula (Ib) described infra and Compound A described infra, and component B being a PD-1/PD-L1 inhibitor. Another aspect of the present invention covers the use of such combinations as described herein for the preparation of a medicament for the treatment or prophylaxis of a disease, particularly for the treatment of a hyper-proliferative disease.

BACKGROUND

Cancer is the second most prevalent cause of death in the United States, causing 450,000 deaths per year. While substantial progress has been made in identifying some of the likely environmental and hereditary causes of cancer, there is a need for additional therapeutic modalities that target cancer and related diseases. In particular there is a need for therapeutic methods for treating diseases associated with dysregulated growth/proliferation.

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

The integrity of the genome of eukaryotic cells is secured by complex signaling pathways, referred to as the DNA damage response (DDR), and multiple DNA repair mechanisms. Upon recognizing DNA damage activation of the DDR pathways results in cell cycle arrest, suppression of general translation, induction of DNA repair, and, finally, in cell survival or cell death. Proteins that directly recognize aberrant DNA structures, such as the MRE11-Rad50-Nbs1 complex recognizing DNA double strand breaks by binding to double-stranded DNA ends, or RPA (replication protein A) binding to single stranded DNA, recruit and activate the most upstream kinases of the DDR pathway, ATM (ataxia-telangiectasia mutated), ATR (ATM- and Rad3-related, UniProtKB/Swiss-Prot Q13535), and DNA-PKcs (DNA-dependent protein kinase). Whereas ATM is primarily activated by DNA double strand breaks, and DNA-PKcs is mainly involved in non-homologous end joining process of DNA repair, ATR responds to a broad spectrum of DNA damage, including double-strand breaks and lesions derived from interference with DNA replication. Major components of downstream signaling of ATM include Chk2 and p53, whereas ATR signaling involves Chk1 and cdc25. Knockout of the ATR gene in mice is embryonically lethal and ATR knockout cells develop chromosome breaks and undergo apoptosis [E. J. Brown, D. Baltimore: ATR disruption leads to chromosomal fragmentation and early embryonic lethality. Genes Dev. 14, 397-402, 2000]. In contrast, ATM is not essential for cell survival although ATM knockout cells are hypersensitive to ionizing radiation and agents which cause DNA double-strand breaks.

ATR, which forms a complex with ATRIP (ATR-interacting protein, UniProtKB/Swiss-Prot Q8WXE1) is mainly activated by long stretches of single-stranded DNA which are generated by the continuing DNA unwinding activity of helicases upon stalled replication. This replication stress with stalled replication forks may be induced by ultraviolet light, certain chemotherapeutic drugs, hydroxyurea, or aberrant oncogenic signaling resulting in increased replication initiation or origin firing. Activation of ATR results in inhibition of the cell cycle in S or G2 phase via the Chk1-cdc25 pathway and in suppression of late origin firing. The cell gains time to resolve the replication stress and, eventually, to restart replication after the source of stress has been removed. As the ATR pathway ensures cell survival after replication stress it potentially contributes to resistance to chemotherapy. Thus inhibition of ATR kinase activity could be useful for cancer treatment.

In oncogene-driven tumor cells (e.g. Ras mutation/upregulation, Myc upregulation, CyclinE overexpression) increased replication stress has been observed as compared to healthy normal cells. ATR suppression in Ras oncogene driven cells was reported to result in substantial tumor cell killing [O. Gilad, B Y Nabet, et al.: Combining ATR suppression with oncogenic Ras synergistically increases genomic instability, causing synthetic lethality or tumorigenesis in a dosage-dependent manner. Cancer Res. 70, 9693-9702, 2010].

Although ATM and ATR are principally activated by different types of DNA damage their signaling includes some cross-talk thus that they can, at least partially, substitute for each other's function. This finding suggests some tumor-cell selectivity of pharmaceutical inhibition of ATR. A healthy normal cell, which has ATM and ATR pathways in parallel, arrests in G1 phase of the cell cycle upon induced DNA damage even in presence of an ATR inhibitor. In contrast, a tumor cell which most often deficient in ATM and/or p53 signaling relies on the ATR pathway and undergoes cell death in presence of an ATR inhibitor. This suggests that ATR inhibitors may be used for the treatment of tumors with deficient ATM signaling and/or p53 function.

Details of DDR signaling and the functional role of ATM and ATR were recently reviewed in: E. Fokas, R. Prevo et al.: Targeting ATR in DNA damage response and cancer therapeutics. Cancer Treatment Rev 40, 109-117, 2014. J. M. Wagner & S. H. Kaufmann: Prospects for the use of ATR inhibitors to treat cancer. Pharmaceuticals 3, 1311-1334, 2010. D. Woods & J. J. Tuchi: Chemotherapy induced DNA damage response. Cancer Biol. Thera. 14, 379-389, 2013. A. Marechal & L. Zou: DNA damage sensing by the ATM and ATR kinases. Cold Spring Harb. Perspect. Biol. 5, a012716, 2013. M. K. Zeman & K. A. Cimprich: Causes and consequences of replication stress. Nat. Cell Biol. 16, 2-9, 2014. S. Llona-Minguez, A. Höglund et al.: Chemical strategies for development of ATR inhibitors. Exp. Rev. Mol. Med. 16, e10, 2014.

Thus inhibitors of ATR kinase represent valuable compounds that should complement therapeutic options not only as single agents but also in combination with other drugs, which are used in the treatment of hyperproliferative diseases. There is an acute medical need for additional therapeutic options for the treatment of hyper-proliferative diseases.

Recently, the PD-1/PD-L1 signalling pathway has emerged as important regulator of the activity of the immune system. In cancer, tumor cells express PD-L1, the ligand of PD-1, by which they can evade their killing by the host immune system Inhibitors against PD-1 and its ligands PD-L1 and PD-L2 have recently been developed which interfere with this immune-suppressive mechanism and have shown amazing clinical efficacy, by extension of the overall survival of patients with various types of cancer. Some of these inhibitors have been approved for various cancer indications such as melanoma, NSCLC, HNSCC, RCC, bladder cancer and NHL. A large number of additional clinical trials are in progress in other indications and/or in combination with a variety of other antitumor agents in order to improve the therapeutic activity (Iwai et al, J. Biomedical Sci. (2017) 24:26, 1-11; Sweis and Luke, Pharm. Res. (2017) 120, 1-9; Bersanelle and Buti, World Journal of Clinical Oncology, (2017) 8(1), 37-53; Park et al., Arch. Pharm. Res. (2016) 39, 1577-1587).

PD-1 inhibitors are biologics, primarily immunoglobulins of the G subclass, which bind to programmed cell death protein 1 also known as PD-1 and block its activity. Known PD-1 inhibitors are nivolumab (Opdivo, BMS-936558, MDX1106), pembrolizumab (Keytruda, MK-3475, lambrolizumab), PDR-001, JS001 and STI-A1110.

PD-1 (also known as CD279) is a receptor protein which is expressed as monomer on the surface of various immune cells mainly on activated CD4+ and CD8+ T cells, on macrophages and on activated B cells, but was also found on natural killer (NK) cells and antigen presenting cells (APC). The extracellular domain of this type I membrane protein consists of a single IgV-like domain, followed by a transmembrane domain and a cytoplasmic region, which contains an immunoreceptor tyrosine-based inhibitory and switch motifs (ITIM and ITSM). Upon binding to its ligand PD-L1 or PD-L2, the phosphatase SHP-2 is recruited which dephosphorylates the kinase ZAP70, a major component of the T cell receptor (TCR) signaling complex. This shuts down TCR signaling and inhibits the cytotoxic activity of the T cells, their interferon gamma production and proliferation. In addition, PD-1 ligation up-regulates E3-ubiquitin ligases CBL-b and c-CBL that trigger T cell receptor downmodulation. PD-1 is encoded by the Pdcd1 gene in humans and is transcriptionally activated by transcription factors NFATc1, IRF9 and FoxO1, which are activated upon TCR activation and by T cell exhaustion signals such as transforming growth factor β and eomesodermin. The activation induced expression of PD-1 suggests that this receptor regulates rather the later phase of the immune response in the peripheral tissue (effector phase, memory response and chronic infection). This is in contrast to CTLA-4, another immune check point protein, which is more active in the earlier priming phase of the immune response and inhibitors of CTLA-4 (e.g. ipilimumab) appear to be less well tolerated in patients. (Iwai et al, J. Biomedical Sci. (2017) 24:26, 1-11; Sweis and Luke, Pharm. Res. (2017) 120, 1-9; Park et al., Arch. Pharm. Res. (2016) 39, 1577-1587).

PD-L1 inhibitors are biologics, primarily immunoglobulins of the G subclass, which bind to the ligand of PD-1 and block its activity. Known PD-L1 inhibitors are atezolizumab (Tecentriq, MPDL3280A), durvalumab (MEDI4736), avelumab (MSB0010718C), BMS-936559 (MDX1105) and LY3300054.

PD-L1 (also known as B7-H1, CD274) is one of the ligands of PD-1. PD-L1 is broadly expressed on the cell surface of many different immune cell populations (e.g. T-, B- NK-cells, DC, monocytes, macrophages), on activated vascular endothelial cells, but also epithelial cells including tumor cells of various entities such as melanoma, lung, ovarian and colon cancers. The expression of PD-L1 is enhanced by proinflammatory cytokines such as interferon gamma, interferon Type I and gamma chain cytokines (IL-2, -4, -7, -9, -15, -21). As described above, T cell activation is inhibited upon interaction with PD-1 and thereby the immune response is dampened (Park et al., Arch. Pharm. Res. (2016) 39, 1577-1587; Menon et al., Cancers (2016) 8, 106, 1-21).

Yap et al. (European Journal of Cancer, Volume 69, Supplement 1, December 2016, Page S2) describe the results of a phase I modular study of AZD6738, a novel oral, potent and selective ataxia telangiectasia Rad3-related (ATR) inhibitor in combination with carboplatin, olaparib or durvalumab (a PD-L1 inhibitor) in patients with advanced cancers. AZD6738 was given as 80 mg twice per day at days 1-14 monotherapy run-in. After this run-in combination treatment started. 1500 mg durvalumab was given once per day at day 1 and at day 28 and 80 mg of AZD6738 was given twice per day at days 22 to 28. Two RECIST (=Response Evaluation Criteria In Solid Tumors) PRs (=Partial Response) were observed after this combination treatment. However, Yap et al. do not demonstrate any synergistic effect for the combination of AZD6738 with durvalumab. Further, the state of the art does not disclose a combination of an ATR inhibitor with a PD-1 inhibitor.

SUMMARY OF THE INVENTION

Surprising effects in an in vivo tumor model were observed when administering Compound A (as defined infra), an ATR kinase inhibitor, in combination with a PD-1/PD-L1 inhibitor. The therapeutic efficacy of the combination described in the present invention has shown superiority to the efficacy achieved by maximum effective/tolerated doses of a PD-1/PD-L1 inhibitor or ATR kinase inhibitor alone.

Therefore, in accordance with a first aspect, the present invention provides combinations of at least two components, component A and component B, comprising component A being an inhibitor of ATR kinase, particularly an inhibitor of ATR kinase selected from VX-803, VX-970, AZD-6738, a compound of general formula (I) described infra, a compound of general formula (Ib) described infra and Compound A described infra, and component B being a PD-1/PD-L1 inhibitor, particularly a PD-1 inhibitor selected from nivolumab (Opdivo, BMS-936558, MDX1106), pembrolizumab (Keytruda, MK-3475, lambrolizumab), PDR-001, JS001, STI-A1110, or particularly a PD-L1 inhibitor selected from atezolizumab (Tecentriq, MPDL3280A), durvalumab (MEDI4736), avelumab (MSB0010718C), BMS-936559 (MDX1105) and LY3300054.

The combinations comprising at least two components A and B, particularly two components, as described herein, are also referred to as "combinations of the present invention".

Further, the present invention covers a kit comprising:
component A: one or more ATR kinase inhibitor(s) as described herein, or a stereoisomer, a tautomer, an N-oxide, a hydrate, a solvate, or a pharmaceutically acceptable salt thereof;
component B: one or more PD-1/PD-L1 inhibitor(s) as described herein,
in which kit optionally either or both of said components A and B in any of the above-mentioned combinations are in the form of a pharmaceutical composition which is ready for use to be administered simultaneously, concurrently, separately or sequentially.

The components may be administered independently of one another by the oral, intravenous, topical, local installations, intraperitoneal or nasal route.

In accordance with another aspect, the present invention concerns the combinations as described herein for the treatment or prophylaxis of a disease, preferably a hyper-proliferative disease as described infra.

In accordance with another aspect, the present invention covers the use of such combinations as described herein for the preparation of a medicament for the treatment or prophylaxis of a disease, preferably a hyper-proliferative disease as described infra.

In accordance with another aspect, the present invention concerns methods for the treatment and/or prophylaxis of a disease, preferably a hyper-proliferative disease as described infra, using an effective amount of the combinations as described herein.

DETAILED DESCRIPTION OF THE INVENTION

The term "inhibitor of ATR kinase" or the term "ATR kinase inhibitor" as used herein means any compound that inhibits ATR kinase. Examples of such compounds are described infra ("COMPONENT A OF THE COMBINATION").

The term "comprising" when used in the specification includes "consisting of".

The terms as mentioned in the present text in context with compounds of general formula (I) or (Ib) have the following meanings:

The term "halogen atom", "halo-" or "Hal-" is to be understood as meaning a fluorine, chlorine, bromine or iodine atom.

The term "$C_1$-$C_6$-alkyl" is to be understood as meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl or iso-propyl group.

The term "$C_1$-$C_6$-haloalkyl" is to be understood as meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said $C_1$-$C_6$-haloalkyl group is, for example, —$CF_3$, —$CHF_2$, —$CH_2F$, —$CF_2CF_3$ or —$CH_2CF_3$.

The term "$C_1$-$C_4$-hydroxyalkyl" is to be understood as meaning a linear or branched, saturated, monovalent hydrocarbon group in which the term "$C_1$-$C_4$-alkyl" is defined supra, and in which one or more hydrogen atoms is replaced by a hydroxy group, e.g. a hydroxymethyl, 1-hydroxyethyl, 2-hydroxyethyl, 1,2-dihydroxyethyl, 3-hydroxypropyl, 2-hydroxypropyl, 2,3-dihydroxypropyl, 1,3-dihydroxypropan-2-yl, 3-hydroxy-2-methyl-propyl, 2-hydroxy-2-methyl-propyl, 1-hydroxy-2-methyl-propyl group.

The term "$C_1$-$C_6$-alkoxy" is to be understood as meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof. Particularly, said "$C_1$-$C_6$-alkoxy" can contain 1, 2, 3, 4 or 5 carbon atoms, (a "$C_1$-$C_5$-alkoxy"), preferably 1, 2, 3 or 4 carbon atoms ("$C_1$-$C_4$-alkoxy").

The term "$C_1$-$C_6$-haloalkoxy" is to be understood as meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said $C_1$-$C_6$-haloalkoxy group is, for example, —$OCF_3$, —$OCHF_2$, —$OCH_2F$, —$OCF_2CF_3$, or —$OCH_2CF_3$.

The term "$C_2$-$C_6$-alkenyl" is to be understood as meaning a linear or branched, monovalent hydrocarbon group, which contains one or more double bonds, and which has 2, 3, 4, 5 or 6 carbon atoms or 2, 3 or 4 carbon atoms ("$C_2$-$C_4$-alkenyl"), particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)

ethenyl, buta-1,3-dienyl, penta-1,4-dienyl, hexa-1,5-dienyl, or methylhexadienyl group. Particularly, said group is vinyl or allyl.

The term "$C_3$-$C_{10}$-cycloalkyl" is to be understood as meaning a saturated, monovalent, mono-, or bicyclic hydrocarbon ring which contains 3, 4, 5, 6, 7, 8, 9 or 10 carbon atoms ("$C_3$-$C_{10}$-cycloalkyl"). Said $C_3$-$C_{10}$-cycloalkyl group is for example, a monocyclic hydrocarbon ring, e.g. a cyclopropyl, cyclobutyl, cyclopentyl, cyclohexyl, cycloheptyl, cyclooctyl, cyclononyl or cyclodecyl, or a bicyclic hydrocarbon ring, e.g. a perhydropentalenylene or decalin ring. Particularly, said ring contains 3, 4, 5 or 6 carbon atoms ("$C_3$-$C_6$-cycloalkyl"), preferably cyclopropyl.

The term "3- to 10-membered heterocycloalkyl" is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NR$_a$, in which R$_a$ represents a hydrogen atom, or a $C_1$-$C_6$-alkyl or $C_1$-$C_6$-haloalkyl group; it being possible for said heterocycloalkyl group to be attached to the rest of the molecule via any one of the carbon atoms or, if present, the nitrogen atom.

Particularly, said 3- to 10-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example. Optionally, said heterocycloalkyl can be benzo fused. Preferably, the 3- to 6-membered heterocycloalkyl is a tetrahydrofuranyl, tetrahydropyranyl or piperazinyl.

Said heterocycloalkyl can be bicyclic, such as, without being limited thereto, a 5,5-membered ring, e.g. a hexahydrocyclopenta[c]pyrrol-2(1H)-yl ring, or a 5,6-membered bicyclic ring, e.g. a hexahydropyrrolo[1,2-a]pyrazin-2(1H)-yl ring.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiacliazinyl, 4,5-dihydrooxazolyl, or 4H-[1,4]thiazinyl ring, for example, or, it may be benzo-fused, such as, without being limited thereto, a dihydroisoquinolinyl ring, for example.

The term "3- to 10-membered heterocycloalkoxy" of formula —O-heterocycloalkyl, in which the term "heterocycloalkyl" is defined supra, is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NR$_a$, in which R$_a$ represents a hydrogen atom, a $C_1$-$C_6$-alkyl or $C_1$-$C_6$-haloalkyl group and which is connected to the rest of the molecule via an oxygen atom, e.g. a pyrrolidineoxy, tetrahydrofuraneoxy or tetrahydropyranoxy.

The term "4- to 10-membered heterocycloalkenyl" is to be understood as meaning an unsaturated, monovalent, mono- or bicyclic hydrocarbon ring which contains 3, 4, 5, 6, 7, 8 or 9 carbon atoms, and one or more heteroatom-containing groups selected from C(=O), O, S, S(=O), S(=O)$_2$, NR$_a$, in which R$_a$ represents a hydrogen atom, or a $C_1$-$C_6$-alkyl or $C_1$-$C_6$-haloalkyl group; it being possible for said heterocycloalkenyl group to be attached to the rest of the molecule via any one of the carbon atoms or, if present, the nitrogen atom. Examples of said heterocycloalkenyl may contain one or more double bonds, e.g. 4H-pyranyl, 2H-pyranyl, 3,6-dihydro-2H-pyran-4-yl, 3,6-dihydro-2H-thiopyran-4-yl, 1,2,3,6-tetrahydropyridin-4-yl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, 4H-[1,4]thiazinyl or 5,6-dihydroimidazo[1,2-a]pyrazin-7(8H)-yl group or it may be benzo fused.

The term "heteroaryl" is understood as meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), 5 or 6 or 9 or 10 ring atoms (a "5- to 10-membered heteroaryl" group) or particularly 5 or 6 ring atoms ("5- to 6-membered heteroaryl" group), and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, oxepinyl or 1H-pyrrolo[2,3-b]pyridin-4-yl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_5$-$C_6$; particularly $C_3$-$C_6$.

Further, as used herein, the term "$C_2$-$C_4$", as used throughout this text, e.g. in the context of "$C_2$-$C_4$-alkenyl" is to be understood as meaning a alkenyl group having a finite number of carbon atoms of 2 to 4, i.e. 2, 3 or 4 carbon atoms. It is to be understood further that said term "$C_2$-$C_4$" is to be interpreted as any sub-range comprised therein, e.g. $C_2$-$C_4$, $C_2$-$C_3$, $C_3$-$C_4$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

By "stable compound" or "stable structure" is meant a compound that is sufficiently robust to survive isolation to a useful degree of purity from a reaction mixture, and formulation into an efficacious therapeutic agent.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of the compound of component A, particularly of Compound A. An isotopic variation of the compound of component A is defined as one in which at least one atom is replaced by an atom having the same atomic number but an atomic mass different from the atomic mass usually or predominantly found in nature. Examples of isotopes that can be incorporated into the compound of component A include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$PF, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of the compound of component A, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of the compound of component A can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

The compounds of component A may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of component A may contain sulphur atoms which are asymmetric, such as an asymmetric sulphoxide or sulphoximine group, of structure:

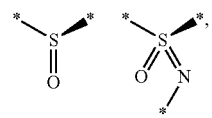

for example, in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds of component A are those which produce the more desirable biological activity, most preferred is Compound A. Separated, pure or partially purified isomers and stereoisomers or racemic or diastereomeric mixtures of the compounds of component A are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of component A as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of component A may be achieved by any suitable state of the art method, such as chromatography, especially chiral chromatography, for example.

Further, the compounds of component A, particularly of Compound A, may exist as tautomers. For example, any compound of component A which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

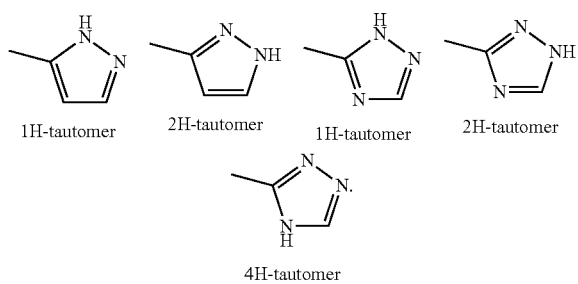

The present combination includes all possible tautomers of the compounds of component A, particularly the 1H-tautomer or the 2H-tautomer of the pyrazol-5-yl group in 8-position of the naphthyridine core of Compound A, as single tautomers, or as any mixture of said tautomers, in any ratio.

Further, the compounds of component A, particularly Compound A, can exist as N-oxides, which are defined in that at least one nitrogen of the compounds of the present invention is oxidised. The present combination includes all such possible N-oxides of component A.

The present combination also relates to useful forms of the compounds as disclosed herein, such as metabolites, hydrates, solvates, prodrugs, salts, in particular pharmaceutically acceptable salts, and co-precipitates.

The compounds of the present combination can exist as a hydrate, or as a solvate, wherein the compounds of the present combination contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present combination includes all such hydrates or solvates.

Further, the compounds of the present combination can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The present invention includes all possible salts of the components of the present combination as single salts, or as any mixture of said salts, in any ratio.

Furthermore, the present invention includes all possible crystalline forms, or polymorphs, of the compounds of components of the present combination, either as single polymorphs, or as a mixture of more than one polymorph, in any ratio.

When radicals in the compounds of the present combination are substituted, the radicals may be mono- or poly-substituted, unless specified otherwise. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease or the development, the course or the progression of such states and/or the symptoms of such states. The term "disease" includes but is not limited a condition, a disorder, an injury or a health problem. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease or a development or advancement of such states and/or the symptoms of such states. The treatment or prevention of a disease may be partial or complete.

Component a of the Combination

Component A can be selected from inhibitors of ATR kinase specifically or generically disclosed in the following publications: J. Med. Chem. 2013, 56, 2125-2138; Exp. Rev. Mol. Med. 16, e10, 2014; WO2010054398A1; WO-2010071837A1; WO2010073034A1; WO2011143399A1; WO2011143419A1; WO2011143422A1; WO2011-143423A2; WO2011143425A2; WO2011143426A1; WO-2011154737A1; WO2011163527A1; WO2012138938A1; WO2012178123A1; WO2012178124A1; WO2012-178125A1; WO2013049719A1; WO2013049720A1; WO-2013049722A1; WO2013049859A1; WO2013071085A1; WO2013071088A1; WO2013071090A1; WO2013-071093A1; WO2013071094A1; WO2013152298A1; WO2014062604A1; WO2014089379A1; WO2014143240; WO 2014143241; WO 2014143242; ACS Med. Chem. Lett. 2015. 6, 37-41; ACS Med. Chem. Lett. 2015. 6, 42-46, WO 2015085132, WO 2015187451.

In another embodiment of the present invention component A is a compound selected from VX-803, VX-970, AZD-6738 and/or a compound of general formula (I)

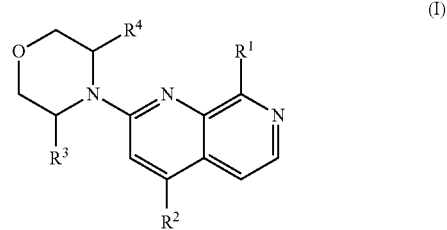

in which:

R$^1$ represents a group selected from:

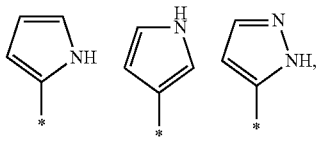

wherein * indicates the point of attachment of said group with the rest of the molecule;

R$^2$ represents hydrogen, halogen, —NR$^7$R$^8$, CN, C$_1$-C$_6$-alkyl, C$_1$-C$_6$-alkoxy, 3- to 10-membered heterocycloalkoxy, C$_2$-C$_6$-alkenyl, C$_3$-C$_6$-cycloalkyl, 3- to 10-membered heterocycloalkyl, 4- to 10-membered heterocycloalkenyl, phenyl, heteroaryl, —(CO)OR$^7$, —(CO)NR$^7$R$^8$, —(SO$_2$)R$^9$, —(SO)R$^9$, —SR$^9$, —(SO$_2$)NR$^7$R$^8$, —NR$^7$(SO$_2$)R$^9$, —((SO)=NR$^{11}$)R$^{10}$, —N=(SO)R$^9$R$^{10}$, —SiR$^{10}$R$^{11}$R$^{12}$, —(PO)(OR$^7$)$_2$, —(PO)(OR$^7$)R$^{10}$ or —(PO)(R$^{10}$)$_2$, wherein each C$_1$-C$_6$-alkyl, C$_1$-C$_6$-alkoxy, 3- to 10-membered heterocycloalkoxy, C$_2$-C$_6$-alkenyl, C$_3$-C$_6$-cycloalkyl, 3- to 10-membered heterocycloalkyl, phenyl or heteroaryl is optionally substituted, one or more times, independently from each other, with halogen, OH, —NR$^7$R$^8$, C$_1$-C$_6$-alkyl optionally substituted one or more times with hydroxyl or phenyl, C$_1$-C$_6$-haloalkyl, C$_1$-C$_6$-alkoxy, C$_3$-C$_6$-cycloalkyl, 3- to 6-membered heterocycloalkyl, phenyl, —(CO)OR$^7$, —(CO)NR$^7$R$^8$, —NR$^7$(CO)R$^{10}$, —NR$^8$(CO)OR$^7$, —NR$^8$(CO)NR$^7$R$^8$, —(SO$_2$)R$^9$, —(SO)R$^9$, —SR$^9$, —(SO$_2$)NR$^7$R$^8$, —NR$^7$(SO$_2$)R$^9$, —((SO)=NR$^{11}$)R$^{10}$, —N=(SO)R$^9$R$^{10}$, —(PO)(OR$^7$)$_2$, —(PO)(OR$^7$)R$^{10}$, —(PO)(R$^{10}$)$_2$ or with a heteroaryl group which is optionally substituted, one or more times, with C$_1$-C$_4$-alkyl;

wherein each 4- to 10-membered heterocycloalkenyl is optionally substituted, one or more times, independently from each other, with C$_1$-C$_4$-alkyl;

R$^3$, R$^4$ represent, independently from each other, hydrogen or methyl;

R$^7$, R$^8$ represent, independently from each other, hydrogen, C$_1$-C$_6$-alkyl, C$_3$-C$_6$-cycloalkyl or phenyl, which phenyl is optionally substituted, one or more times, with halogen; or R$^7$ and R$^8$ together represent a 4-, 5-, 6- or 7-membered cyclic amine group, which is optionally substituted, one or more times, independently from each other, with a substituent selected from C$_1$-C$_6$-alkyl, C$_1$-C$_6$-haloalkyl, said 4-, 5-, 6- or 7-membered cyclic amine group optionally containing one further heteroatom selected from the group consisting of O, N and S;

R$^9$ represents C$_1$-C$_4$-alkyl or phenyl, wherein each C$_1$-C$_4$-alkyl or phenyl is optionally substituted, one or more times, independently from each other, with R$^{13}$;

R$^{10}$ represents C$_1$-C$_4$-alkyl; or

R$^9$ and R$^{10}$ together, in case of —N=(SO)R$^9$R$^{10}$ group, represent a 5- to 8-membered heterocycloalkyl group;

R$^{11}$ represents hydrogen, C$_1$-C$_4$-alkyl, —(CO)OR$^7$, —(CO)NR$^7$R$^8$ or CN;

R$^{12}$ represents hydrogen or C$_1$-C$_4$-alkyl;

R$^{13}$ represents halogen, OH, —NR$^7$R$^8$, CN, NO$_2$, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, C$_3$-C$_6$-cycloalkyl, —(CO)OR$^7$ or —(CO)NR$^7$R$^8$;

or a stereoisomer, a tautomer, an N-oxide, a hydrate, a solvate, or a pharmaceutically acceptable salt thereof.

In context with the present invention the term "VX-803" is understood as meaning 2-amino-6-fluoro-N-[5-fluoro-4-(4-{[4-(oxetan-3-yl)piperazin-1-yl]carbonyl}piperidin-1-yl)pyridin-3-yl]pyrazolo[1,5-a]pyrimidine-3-carboxamide. It has the following structure:

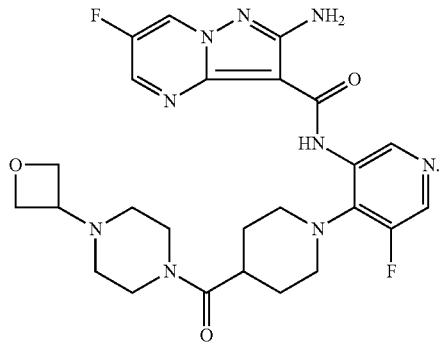 [SMILES: Nc1nn2cc(F)cnc2c1C(=O)Nc1cncc(F)c1N1CCC(C(=O)N2CCN(C3COC3)CC2)CC1]

In context with the present invention the term "VX-970" is understood as meaning 3-(3-{4-[(methylamino)methyl]phenyl}-1,2-oxazol-5-yl)-5-[4-(propan-2-ylsulfonyl)phenyl]pyrazin-2-amine. It has the following structure:

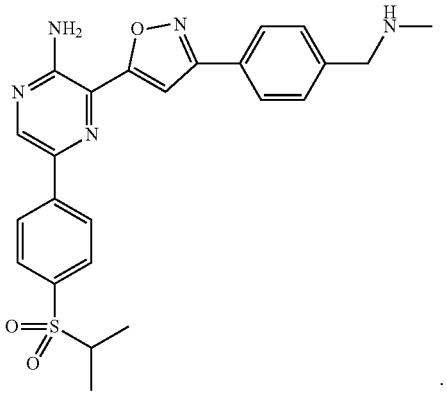 [SMILES: CNCc1ccc(-c2cc(-c3nc(-c4ccc(S(=O)(=O)C(C)C)cc4)cnc3N)on2)cc1]

In context with the present invention the term "AZD-6738" is understood as meaning 4-{4-[(3R)-3-methylmorpholin-4-yl]-6-[1-(S-methyl sulfonimidoyl)cyclopropyl]pyrimidin-2-yl}-1H-pyrrolo[2,3-b]pyridine. It has the following structure:

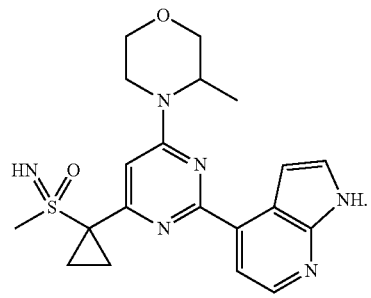

In another embodiment of the invention, component A is a compound selected from VX-803, VX-970, AZD-6738 and/or a compound of general formula (Ib)

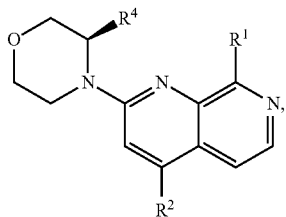

(Ib)

in which $R^1$, $R^2$, $R^4$, $R^7$, $R^8$, $R^9$, $R^{10}$, $R^{11}$, $R^{12}$ and $R^{13}$ are as defined for the compound of general formula (I) supra.

In another embodiment of the invention, component A is a compound selected from VX-803, VX-970, AZD-6738 and/or a compound of general formula (Ib)

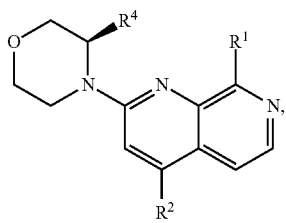

(Ib)

in which
$R^1$ represents:

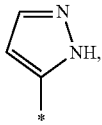

wherein * indicates the point of attachment of said group with the rest of the molecule;
$R^2$ represents hydrogen, fluoro, chloro, CN, methyl, $C_1$-$C_4$-alkoxy, $C_2$-$C_3$-alkenyl, cyclopropyl, 3- to 6-membered heterocycloalkyl, 4- to 6-membered heterocycloalkenyl, phenyl, pyridinyl, thiazolyl, —(SO$_2$)R$^9$, —SR$^9$, —((SO)=NR$^{11}$)R$^{10}$, —N=(SO)R$^9$R$^{10}$,
wherein each methyl, $C_1$-$C_4$-alkoxy, $C_2$-$C_3$-alkenyl, cyclopropyl, 3- to 6-membered heterocycloalkyl, phenyl, pyridinyl or thiazolyl is optionally substituted, one or more times, independently from each other, with fluoro, chloro, OH, —NR$^7$R$^8$, methyl, 5-membered heterocycloalkyl, —NR$^8$(CO)OR$^7$, —(SO$_2$)R$^9$, —((SO)=NR$^{11}$)R$^{10}$, —(PO)(OR$^7$)$_2$, or with a group selected from:

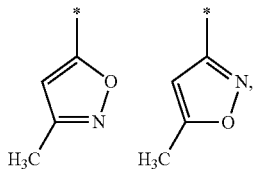

wherein * indicates the point of attachment of said group with the rest of the molecule;
wherein each 4- to 6-membered heterocycloalkenyl is optionally substituted, one or more times, with methyl;

$R^4$ represents hydrogen or methyl;
$R^7$, $R^8$ represent, independently from each other, hydrogen or $C_1$-$C_4$-alkyl;
$R^9$ represents $C_1$-$C_4$-alkyl;
$R^{10}$ represents $C_1$-$C_4$-alkyl; or
$R^9$ and $R^{10}$ together, in case of —N=(SO)R$^9$R$^{10}$ group, represent a 6-membered heterocycloalkyl group;
$R^{11}$ represents hydrogen, methyl, —(CO)OR$^7$;
or a stereoisomer, a tautomer, an N-oxide, a hydrate, a solvate, or a pharmaceutically acceptable salt thereof.

In another embodiment of the invention, component A is a compound of general formula (Ib)

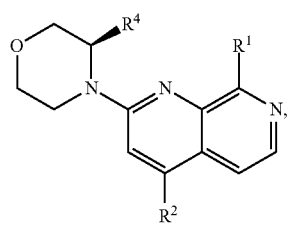

(Ib)

in which
$R^1$ represents:

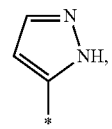

wherein * indicates the point of attachment of said group with the rest of the molecule;
$R^2$ represents hydrogen, fluoro, chloro, CN, methyl, $C_1$-$C_4$-alkoxy, $C_2$-$C_3$-alkenyl, cyclopropyl, 3- to 6-membered heterocycloalkyl, 4- to 6-membered heterocycloalkenyl, phenyl, pyridinyl, thiazolyl, —(SO$_2$)R$^9$, —SR$^9$, —((SO)=NR$^{11}$)R$^{10}$, —N=(SO)R$^9$R$^{10}$,
wherein each methyl, $C_1$-$C_4$-alkoxy, $C_2$-$C_3$-alkenyl, cyclopropyl, 3- to 6-membered heterocycloalkyl, phenyl, pyridinyl or thiazolyl is optionally substituted, one or more times, independently from each other, with fluoro, chloro, OH, —NR$^7$R$^8$, methyl, 5-membered heterocycloalkyl, —NR$^8$(CO)OR$^7$, —(SO$_2$)R$^9$, —((SO)=NR$^{11}$)R$^{10}$, —(PO)(OR$^7$)$_2$, or with a group selected from:

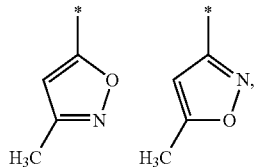

wherein * indicates the point of attachment of said group with the rest of the molecule;
wherein each 4- to 6-membered heterocycloalkenyl is optionally substituted, one or more times, with methyl;
$R^4$ represents hydrogen or methyl;
$R^7$, $R^8$ represent, independently from each other, hydrogen or $C_1$-$C_4$-alkyl;

R⁹ represents $C_1$-$C_4$-alkyl;
R¹⁰ represents $C_1$-$C_4$-alkyl; or
R⁹ and R¹⁰ together, in case of —N═(SO)R⁹R¹⁰ group, represent a 6-membered heterocycloalkyl group;
R¹¹ represents hydrogen, methyl, —(CO)OR⁷;
or a stereoisomer, a tautomer, an N-oxide, a hydrate, a solvate, or a pharmaceutically acceptable salt thereof.

In another embodiment, component A is a compound selected from:

4-[(2-(morpholin-4-yl)-8-[2H-pyrazol-3-yl]-[1,7]¬aphthyridine-4-yl]phenyl-N-ethoxycarbonyl-S-methylsulphoximide 4-[(2-(morpholin-4-yl)-8-(2H-pyrazol-3-yl)-[1,7]naphthyridine-4-yl]phenyl-S-methylsulphoximide 4-[6-(methylsulfonyflpyridin-3-yl]-2-(morpholin-4-yl)-8-(1H-pyrazol-5-yl)-1,7-naphthyridine 4-(3,6-dihydro-2H-pyran-4-yl)-2-(morpholin-4-yl)-8-(1H-pyrazol-3-yl)-[1,7]naphthyridine 4-[4-(N,S-dimethylsulfonimidoyl)phenyl]-2-[morpholin-4-yl]-8-(1H-pyrazol-5-yl)-1,7-naphthyridine 4-[4-methyl-6-(methylsulfonyflpyridin-3-yl]-2-(morpholin-4-yl)-8-(1H-pyrazol-5-yl)-1,7-naphthyridine 4-(4-methanesulphonylphenyl)-2-(morpholin-4-yl)-8-(1H-pyrazol-3-yl)-[1,7]naphthyridine 4-(2-methanesulphonylphenyl)-2-(morpholin-4-yl)-8-(1H-pyrazol-3-yl)-[1,7]naphthyridine hydrochloride dimethyl {4-[2-(morpholin-4-yl)-8-(1H-pyrazol-5-yl)-1,7-naphthyridin-4-yl]phenyl}phosphonate 4-isopropenyl-2-(morpholin-4-yl)-8-(1H-pyrazol-3-yl)-[1,7]naphthyridine 2-(morpholin-4-yl)-4-phenyl-8-(1H-pyrazol-3-yl)-[1,7]naphthyridine 4-[4-(S-ethylsulfonimidoyl)phenyl]-2-(morpholin-4-yl)-8-(1H-pyrazol-5-yl)-1,7-naphthyridine 3-[(2-(morpholin-4-yl)-8-[2H-pyrazol-3-yl]-[1,7]naphthyridine-4-yl]phenyl-N-ethoxycarbonyl-S-methylsulphoximide 4-(1-methyl-1,2,3,6-tetrahydropyridin-4-yl)-2-(morpholin-4-yl)-8-(1H-pyrazol-5-yl)-1,7-naphthyridine 4-(3-methanesulphonylphenyl)-2-(morpholin-4-yl)-8-(1H-pyrazol-3-yl)-[1,7]naphthyridine 4-[5-methyl-6-(methylsulfonyflpyridin-3-yl]-2-(morpholin-4-yl)-8-(1H-pyrazol-5-yl)-1,7-naphthyridine 2-(morpholin-4-yl)-8-(1H-pyrazol-5-yl)-4-(1,2,3,6-tetrahydropyridin-4-yl)-1,7-naphthyridine 4-cyclopropyl-2-(morpholin-4-yl)-8-(1H-pyrazol-3-yl)-[1,7]naphthyridine 3-[(2-(morpholin-4-yl)-8-(2H-pyrazol-3-yl)-[1,7]naphthyridine-4-yl]phenyl-S-methylsulphoximide 4-methyl-2-(morpholin-4-yl)-8-(1H-pyrazol-3-yl)-[1,7]naphthyridine hydrochloride 4-[2-(methylsulfonyl)-1,3-thiazol-4-yl]-2-(morpholin-4-yl)-8-(1H-pyrazol-5-yl)-1,7-naphthyridine 4-[2-(morpholin-4-yl)-8-(1H-pyrazol-5-yl)-1,7-naphthyridin-4-yl]pyridin-2(1H)-one 5-[2-(morpholin-4-yl)-8-(1H-pyrazol-5-yl)-1,7-naphthyridin-4-yl]pyridin-2(1H)-one 4-[2-fluoro-4-(methylsulfonyl)phenyl]-2-(morpholin-4-yl)-8-(1H-pyrazol-5-yl)-1,7-naphthyridine 2-(morpholin-4-yl)-4-{4-[S-(propan-2-yl)sulfonimidoyl]phenyl}-8-(1H-pyrazol-5-yl)-1,7-naphthyridine 4-(4-methanesulphonylphenyl)-2-((R)-3-methylmorpholin-4-yl)-8-(2H-pyrazol-3-yl)-[1,7]naphthyridine 2-((R)-3-methylmorpholin-4-yl)-4-phenyl-8-(2H-pyrazol-3-yl)-[1,7]naphthyridine 4-(3-methanesulphonylphenyl)-2-((R)-3-methylmorpholin-4-yl)-8-(2H-pyrazol-3-yl)-[1,7]naphthyridine 4-cyclopropyl-2-((R)-3-methylmorpholin-4-yl)-8-(1H-pyrazol-3-yl)-[1,7]naphthyridine 4-[2-((R)-3-methylmorpholin-4-yl)-8-(2H-pyrazol-3-yl)-[1,7]naphthyridine-4-yl]phenyl-S-methylsulphoximide 3-[2-((R)-3-methylmorpholin-4-yl)-8-(2H-pyrazol-3-yl)-[1,7]naphthyridine-4-yl]phenyl-S-methylsulphoximide 4-methanesulphonyl-2-(morpholin-4-yl)-8-[2-(tetrahydropyran-2-yl)-2H-pyrazol-3-yl]-[1,7]naphthyridine 2-[(3R)-3-methylmorpholin-4-yl]-4-(methylsulfonyl)-8-(1H-pyrazol-5-yl)-1,7-naphthyridine 2-(morpholin-4-yl)-8-(1H-pyrazol-3-yl)-[1,7]naphthyridine-4-carbonitrile 2-((R)-3-methylmorpholin-4-yl)-8-(-2H-pyrazol-3-yl)-[1,7]naphthyridine-4-carbonitrile 2-morpholin-4-yl-8-(1H-pyrazol-3-yl)-[1,7]naphthyridine-4-carboxamide 4-methanesulphonylmethyl-2-morpholin-4-yl-8-(2H-pyrazol-3-yl)-[1,7]naphthyridine

[2-(morpholin-4-yl)-8-(2H-pyrazol-3-yl)-[1,7]naphthyridine-4-yl]methanol 4-(1-methanesulphonylcyclopropyl)-2-(morpholin-4-yl)-8-(2H-pyrazol-3-yl)-[1,7]naphthyridine 4-isopropoxy-2-(morpholin-4-yl)-8-(1H-pyrazol-3-yl)-[1,7]naphthyridine 2-(morpholin-4-yl)-4-(propan-2-yloxy)-8-(1H-pyrrol-2-yl)-1,7-naphthyridine 4-[3-(S-methylsulfonimidoyl)propoxy]-2-(morpholin-4-yl)-8-(1H-pyrazol-5-yl)-1,7-naphthyridine 4-ethoxy-2-(morpholin-4-yl)-8-(1H-pyrazol-3-yl)-[1,7]naphthyridine 4-methoxy-2-(morpholin-4-yl)-8-(1H-pyrazol-3-yl)-[1,7]naphthyridine 2-methyl-1-{[2-(morpholin-4-yl)-8-(1H-pyrazol-5-yl)-1,7-naphthyridin-4-yl]oxy}propan-2-ol 2-(morpholin-4-yl)-8-(1H-pyrazol-5-yl)-4-(tetrahydrofuran-2-ylmethoxy)-1,7-naphthyridine 3-{[2-(morpholin-4-yl)-8-(1H-pyrazol-5-yl)-1,7-naphthyridin-4-yl]oxy}dihydrofuran-2(3H)-one 4-[(3-methyl-1,2-oxazol-5-yl)methoxy]-2-(morpholin-4-yl)-8-(1H-pyrazol-5-yl)-1,7-naphthyridine 4-[(5-methyl-1,2-oxazol-3-yl)methoxy]-2-(morpholin-4-yl)-8-(1H-pyrazol-5-yl)-1,7-naphthyridine 4-benzyloxy-2-(morpholin-4-yl)-8-(1H-pyrazol-3-yl)-[1,7]naphthyridine 4-isopropoxy-2-((R)-3-methylmorpholin-4-yl)-8-(1H-pyrazol-3-yl)-[1,7]naphthyridine tert-butyl [4-({2-[(3R)-3-methylmorpholin-4-yl]-8-(1H-pyrazol-5-yl)-1,7-naphthyridin-4-yl}oxy)butyl]carbamate 4-methoxy-2-((R)-3-methylmorpholin-4-yl)-8-(1H-pyrazol-3-yl)-[1,7]naphthyridine tert-butyl [3-({2-[(3R)-3-methylmorpholin-4-yl]-8-(1H-pyrazol-5-yl)-1,7-naphthyridin-4-yl}oxy)propyl]carbamate 2-({2-[(3R)-3-methylmorpholin-4-yl]-8-(1H-pyrazol-5-yl)-1,7-naphthyridin-4-yl}oxy)ethanamine tert-butyl [2-({2-[(3R)-3-methylmorpholin-4-yl]-8-(1H-pyrazol-5-yl)-1,7-naphthyridin-4-yl}oxy)ethyl]carbamate 4-({2-[(3R)-3-methylmorpholin-4-yl]-8-(1H-pyrazol-5-yl)-1,7-naphthyridin-4-yl}oxy)butan-1-amine 2-[(3R,5S)-3,5-dimethylmorpholin-4-yl]-4-isopropoxy-8-(1H-pyrazol-5-yl)-1,7-naphthyridine 2-[(3R,5R)-3,5-dimethylmorpholin-4-yl]-4-isopropoxy-8-(1H-pyrazol-5-yl)-1,7-naphthyridine 2-(morpholin-4-yl)-8-(1H-pyrazol-5-yl)-4-(tetrahydro-2H-pyran-4-yl)-1,7-naphthyridine 2-(morpholin-4-yl)-8-(1H-pyrazol-3-yl)-[1,7]naphthyridine hydrochloride
4-chloro-2-morpholin-4-yl-8-(1H-pyrazol-3-yl)-[1,7]naphthyridine
2-[(3R)-3-methylmorpholin-4-yl]-4-(methylsulfanyl)-8-(1H-pyrazol-5-yl)-1,7-naphthyridine
N-{2-[(3R)-3-methylmorpholin-4-yl]-8-(1H-pyrazol-5-yl)-1,7-naphthyridin-4-yl}-1,4$\lambda^4$-oxathian-4-imine 4-oxide
4-{[dimethyl(oxido)-$\lambda^6$-sulfanylidene]amino}-2-(morpholin-4-yl)-8-(1H-pyrazol-5-yl)-1,7-naphthyridine
2-[(3R)-3-methylmorpholin-4-yl]-4-(piperazin-1-yl)-8-(1H-pyrazol-5-yl)-1,7-naphthyridine
4-isopropoxy-2-((S)-3-methylmorpholin-4-yl)-8-(1H-pyrazol-3-yl)-[1,7]naphthyridine
2-(morpholin-4-yl)-4-(propan-2-yloxy)-8-(1H-pyrrol-3-yl)-1,7-naphthyridine
4-(1-ethyl-1H-pyrazol-5-yl)-2-[(3R)-3-methylmorpholin-4-yl]-8-(1H-pyrazol-5-yl)-1,7-naphthyridine
4-(1-methyl-1H-imidazol-5-yl)-2-[(3R)-3-methylmorpholin-4-yl]-8-(1H-pyrazol-5-yl)-1,7-naphthyridine
2-{2-[(3R)-3-methylmorpholin-4-yl]-8-(1H-pyrazol-5-yl)-1,7-naphthyridin-4-yl}aniline
4-(2,3-difluorophenyl)-2-[(3R)-3-methylmorpholin-4-yl]-8-(1H-pyrazol-5-yl)-1,7-naphthyridine
4-[2-methyl-6-(methylsulfonyl)pyridin-3-yl]-2-[(3R)-3-methylmorpholin-4-yl]-8-(1H-pyrazol-5-yl)-1,7-naphthyridine
4-[2-fluoro-4-(methylsulfonyl)phenyl]-2-[(3R)-3-methylmorpholin-4-yl]-8-(1H-pyrazol-5-yl)-1,7-naphthyridine
4-fluoro-2-{2-[(3R)-3-methylmorpholin-4-yl]-8-(1H-pyrazol-5-yl)-1,7-naphthyridin-4-yl}aniline
4-(1-benzyl-1H-imidazol-5-yl)-2-[(3R)-3-methylmorpholin-4-yl]-8-(1H-pyrazol-5-yl)-1,7-naphthyridine
4-(2-fluorophenyl)-2-[(3R)-3-methylmorpholin-4-yl]-8-(1H-pyrazol-5-yl)-1,7-naphthyridine
2-[(3R)-3-methylmorpholin-4-yl]-4-(2-methyl-1,3-thiazol-5-yl)-8-(1H-pyrazol-5-yl)-1,7-naphthyridine
4-[4-methyl-6-(methylsulfonyl)pyridin-3-yl]-2-[(3R)-3-methylmorpholin-4-yl]-8-(1H-pyrazol-5-yl)-1,7-naphthyridine
4-(1-cyclopropyl-1H-pyrazol-5-yl)-2-[(3R)-3-methylmorpholin-4-yl]-8-(1H-pyrazol-5-yl)-1,7-naphthyridine
4-[2-fluoro-4-(piperazin-1-yl)phenyl]-2-[(3R)-3-methylmorpholin-4-yl]-8-(1H-pyrazol-5-yl)-1,7-naphthyridine
2-[(3R)-3-methylmorpholin-4-yl]-4-[4-(methylsulfonyl)piperazin-1-yl]-8-(1H-pyrazol-5-yl)-1,7-naphthyridine
N-(2,2-dimethylpropyl)-N-methyl-2-[(3R)-3-methylmorpholin-4-yl]-8-(1H-pyrazol-5-yl)-1,7-naphthyridin-4-amine
(1-{2-[(3R)-3-methylmorpholin-4-yl]-8-(1H-pyrazol-5-yl)-1,7-naphthyridin-4-yl}piperidin-4-yl)methanol
N-cyclopropyl-N-methyl-2-[(3R)-3-methylmorpholin-4-yl]-8-(1H-pyrazol-5-yl)-1,7-naphthyridin-4-amine
4-(5,6-dihydroimidazo[1,2-a]pyrazin-7(8H)-yl)-2-[(3R)-3-methylmorpholin-4-yl]-8-(1H-pyrazol-5-yl)-1,7-naphthyridine
N-(4-fluorophenyl)-N-methyl-2-[(3R)-3-methylmorpholin-4-yl]-8-(1H-pyrazol-5-yl)-1,7-naphthyridin-4-amine
2-[(3R)-3-methylmorpholin-4-yl]-4-(6-methylpyridin-3-yl)-8-(1H-pyrazol-5-yl)-1,7-naphthyridine
4-(2-fluoropyridin-3-yl)-2-[(3R)-3-methylmorpholin-4-yl]-8-(1H-pyrazol-5-yl)-1,7-naphthyridine
4-(2-fluoro-4-methylpyridin-3-yl)-2-[(3R)-3-methylmorpholin-4-yl]-8-(1H-pyrazol-5-yl)-1,7-naphthyridine
2-[(3R)-3-methylmorpholin-4-yl]-4-(1-methyl-1H-pyrrol-2-yl)-8-(1H-pyrazol-5-yl)-1,7-naphthyridine
4-(6-fluoro-5-methylpyridin-3-yl)-2-[(3R)-3-methylmorpholin-4-yl]-8-(1H-pyrazol-5-yl)-1,7-naphthyridine
4-(2-fluoro-6-methylpyridin-3-yl)-2-[(3R)-3-methylmorpholin-4-yl]-8-(1H-pyrazol-5-yl)-1,7-naphthyridine
4-(6-fluoropyridin-3-yl)-2-[(3R)-3-methylmorpholin-4-yl]-8-(1H-pyrazol-5-yl)-1,7-naphthyridine
4-(6-methoxypyridin-3-yl)-2-[(3R)-3-methylmorpholin-4-yl]-8-(1H-pyrazol-5-yl)-1,7-naphthyridine
4-(6-methoxy-5-methylpyridin-3-yl)-2-[(3R)-3-methylmorpholin-4-yl]-8-(1H-pyrazol-5-yl)-1,7-naphthyridine
4-(6-fluoro-2-methylpyridin-3-yl)-2-[(3R)-3-methylmorpholin-4-yl]-8-(1H-pyrazol-5-yl)-1,7-naphthyridine
2-[(3R)-3-methylmorpholin-4-yl]-4-[1-methyl-3-(trifluoromethyl)-1H-pyrazol-5-yl]-8-(1H-pyrazol-5-yl)-1,7-naphthyridine
2-[(3R)-3-methylmorpholin-4-yl]-4-(3-methyl-2-thienyl)-8-(1H-pyrazol-5-yl)-1,7-naphthyridine
2-[(3R)-3-methylmorpholin-4-yl]-4-(5-methyl-2-thienyl)-8-(1H-pyrazol-5-yl)-1,7-naphthyridine
2-[(3R)-3-methylmorpholin-4-yl]-4-(4-methyl-3-thienyl)-8-(1H-pyrazol-5-yl)-1,7-naphthyridine
4-(3-chloro-2-thienyl)-2-[(3R)-3-methylmorpholin-4-yl]-8-(1H-pyrazol-5-yl)-1,7-naphthyridine
2-[(3R)-3-methylmorpholin-4-yl]-4-(2-methyl-3-thienyl)-8-(1H-pyrazol-5-yl)-1,7-naphthyridine
2-[(3R)-3-methylmorpholin-4-yl]-8-(1H-pyrazol-5-yl)-4-(1H-pyrrolo[2,3-b]pyridin-4-yl)-1,7-naphthyridine
4-(3,5-dimethyl-1,2-oxazol-4-yl)-2-[(3R)-3-methylmorpholin-4-yl]-8-(1H-pyrazol-5-yl)-1,7-naphthyridine
4-(3-chloro-2-methoxypyridin-4-yl)-2-[(3R)-3-methylmorpholin-4-yl]-8-(1H-pyrazol-5-yl)-1,7-naphthyridine
2-[(3R)-3-methylmorpholin-4-yl]-8-(1H-pyrazol-5-yl)-4-(tetrahydro-2H-pyran-4-yl)-1,7-naphthyridine
4-(3,6-dihydro-2H-thiopyran-4-yl)-2-[(3R)-3-methylmorpholin-4-yl]-8-(1H-pyrazol-5-yl)-1,7-naphthyridine
2-[(3R)-3-methylmorpholin-4-yl]-4-(4-methylpiperidin-1-yl)-8-(1H-pyrazol-5-yl)-1,7-naphthyridine
4-(1-tert-butyl-1H-pyrazol-5-yl)-2-[(3R)-3-methylmorpholin-4-yl]-8-(1H-pyrazol-5-yl)-1,7-naphthyridine
2-[(3R)-3-methylmorpholin-4-yl]-4-(1-methyl-1H-pyrazol-5-yl)-8-(1H-pyrazol-5-yl)-1,7-naphthyridine
2-[(3R)-3-methylmorpholin-4-yl]-4-(3-methyl-1,2-oxazol-5-yl)-8-(1H-pyrazol-5-yl)-1,7-naphthyridine
4-(1-ethyl-3-methyl-1H-pyrazol-5-yl)-2-[(3R)-3-methylmorpholin-4-yl]-8-(1H-pyrazol-5-yl)-1,7-naphthyridine
4-(1,4-dimethyl-1H-pyrazol-5-yl)-2-[(3R)-3-methylmorpholin-4-yl]-8-(1H-pyrazol-5-yl)-1,7-naphthyridine
4-[2-methyl-6-(methylsulfanyl)pyridin-3-yl]-2-[(3R)-3-methylmorpholin-4-yl]-8-(1H-pyrazol-5-yl)-1,7-naphthyridine
4-[2-methyl-6-(S-methylsulfonimidoyl)pyridin-3-yl]-2-[(3R)-3-methylmorpholin-4-yl]-8-(1H-pyrazol-5-yl)-1,7-naphthyridine
2-[(3R)-3-methylmorpholin-4-yl]-4-(1-propyl-1H-pyrazol-5-yl)-8-(1H-pyrazol-5-yl)-1,7-naphthyridine
4-(6,7-dihydro-5H-pyrrolo[1,2-a]imidazol-3-yl)-2-[(3R)-3-methylmorpholin-4-yl]-8-(1H-pyrazol-5-yl)-1,7-naphthyridine
4-[1-ethyl-3-(trifluoromethyl)-1H-pyrazol-5-yl]-2-[(3R)-3-methylmorpholin-4-yl]-8-(1H-pyrazol-5-yl)-1,7-naphthyridine
methyl 5-{2-[(3R)-3-methylmorpholin-4-yl]-8-(1H-pyrazol-5-yl)-1,7-naphthyridin-4-yl}-1H-pyrrole-2-carboxylate
2-[(3R)-3-methylmorpholin-4-yl]-8-(1H-pyrazol-5-yl)-4-(1,2-thiazol-5-yl)-1,7-naphthyridine N,N-dimethyl-2-{2-[(3R)-3-methylmorpholin-4-yl]-8-(1H-pyrazol-5-yl)-1,7-naphthyridin-4-yl}aniline
4-(2,4-difluorophenyl)-2-[(3R)-3-methylmorpholin-4-yl]-8-(1H-pyrazol-5-yl)-1,7-naphthyridine
4-(1-isopropyl-1H-pyrazol-5-yl)-2-[(3R)-3-methylmorpholin-4-yl]-8-(1H-pyrazol-5-yl)-1,7-naphthyridine
ethyl methyl{2-[(3R)-3-methylmorpholin-4-yl]-8-(1H-pyrazol-5-yl)-1,7-naphthyridin-4-yl}phosphinate
4-{[diethyl(oxido)-$\lambda^6$-sulfanylidene]amino}-2-[(3R)-3-methylmorpholin-4-yl]-8-(1H-pyrazol-5-yl)-1,7-naphthyridine
isobutyl methyl{2-[(3R)-3-methylmorpholin-4-yl]-8-(1H-pyrazol-5-yl)-1,7-naphthyridin-4-yl}phosphinate
2-{2-[(3R)-3-methylmorpholin-4-yl]-8-(1H-pyrazol-5-yl)-1,7-naphthyridin-4-yl}propan-2-ol
3-{2-[(3R)-3-methylmorpholin-4-yl]-8-(1H-pyrazol-5-yl)-1,7-naphthyridin-4-yl}pentan-3-ol
4-(5-chloropyridin-3-yl)-2-[(3R)-3-methylmorpholin-4-yl]-8-(1H-pyrazol-5-yl)-1,7-naphthyridine
5-fluoro-2-{2-[(3R)-3-methylmorpholin-4-yl]-8-(1H-pyrazol-5-yl)-1,7-naphthyridin-4-yl}aniline
4-[2-fluoro-3-(methylsulfonyl)phenyl]-2-[(3R)-3-methylmorpholin-4-yl]-8-(1H-pyrazol-5-yl)-1,7-naphthyridine
2-[(3R)-3-methylmorpholin-4-yl]-4-[1-(oxetan-3-yl)-1H-pyrazol-5-yl]-8-(1H-pyrazol-5-yl)-1,7-naphthyridine
4-[2-fluoro-4-(pyrrolidin-1-yl)phenyl]-2-[(3R)-3-methylmorpholin-4-yl]-8-(1H-pyrazol-5-yl)-1,7-naphthyridine
4-[3-(methoxymethyl)-5-methyl-1,2-oxazol-4-yl]-2-[(3R)-3-methylmorpholin-4-yl]-8-(1H-pyrazol-5-yl)-1,7-naphthyridine
2-[(3R)-3-methylmorpholin-4-yl]-4-(5-methyl-1,3,4-oxadiazol-2-yl)-8-(1H-pyrazol-5-yl)-1,7-naphthyridine
N-{2-[(3R)-3-methylmorpholin-4-yl]-8-(1H-pyrazol-5-yl)-1,7-naphthyridin-4-yl}tetrahydro-1H-1$\lambda^4$-thiophen-1-imine 1-oxide
4-{[(4-fluorophenyl)(methyl)oxido-$\lambda^6$-sulfanylidene]amino}-2-[(3R)-3-methylmorpholin-4-yl]-8-(1H-pyrazol-5-yl)-1,7-naphthyridine, mixture of 2 diastereoisomers
4-{[(2-fluorophenyl)(methyl)oxido-$\lambda^6$-sulfanylidene]amino}-2-[(3R)-3-methylmorpholin-4-yl]-8-(1H-pyrazol-5-yl)-1,7-naphthyridine, mixture of 2 diastereoisomers
4-{[(R)(2-fluorophenyl)(methyl)oxido-$\lambda^6$-sulfanylidene]amino}-2-[(3R)-3-methylmorpholin-4-yl]-8-(1H-pyrazol-5-yl)-1,7-naphthyridine, diastereoisomer
4-{[(S)(2-fluorophenyl)(methyl)oxido-$\lambda^6$-sulfanylidene]amino}-2-[(3R)-3-methylmorpholin-4-yl]-8-(1H-pyrazol-5-yl)-1,7-naphthyridine, diastereoisomer
4-(dimethylphosphoryl)-2-[(3R)-3-methylmorpholin-4-yl]-8-(1H-pyrazol-5-yl)-1,7-naphthyridine
4-(diethylphosphoryl)-2-[(3R)-3-methylmorpholin-4-yl]-8-(1H-pyrazol-5-yl)-1,7-naphthyridine
ethyl isobutyl{2-[(3R)-3-methylmorpholin-4-yl]-8-(1H-pyrazol-5-yl)-1,7-naphthyridin-4-yl}phosphinate
2-[(3R)-3-methylmorpholin-4-yl]-4-(morpholin-4-yl)-8-(1H-pyrazol-5-yl)-1,7-naphthyridine
4-(1-isobutyl-1H-pyrazol-5-yl)-2-[(3R)-3-methylmorpholin-4-yl]-8-(1H-pyrazol-5-yl)-1,7-naphthyridine
4-[5-fluoro-6-(methylsulfonyl)pyridin-3-yl]-2-[(3R)-3-methylmorpholin-4-yl]-8-(1H-pyrazol-5-yl)-1,7-naphthyridine
4-[(3R)-3-methylmorpholin-4-yl]-2-(morpholin-4-yl)-8-(1H-pyrazol-5-yl)-1,7-naphthyridine
2-[(3R)-3-methylmorpholin-4-yl]-4-(4-methyl-1H-pyrazol-5-yl)-8-(1H-pyrazol-5-yl)-1,7-naphthyridine
4-[2-fluoro-5-(methylsulfonyl)phenyl]-2-[(3R)-3-methylmorpholin-4-yl]-8-(1H-pyrazol-5-yl)-1,7-naphthyridine
4-[4-(isopropylsulfonyl)phenyl]-2-[(3R)-3-methylmorpholin-4-yl]-8-(1H-pyrazol-5-yl)-1,7-naphthyridine
4-(6-fluoropyridin-2-yl)-2-[(3R)-3-methylmorpholin-4-yl]-8-(1H-pyrazol-5-yl)-1,7-naphthyridine
4-(1-ethyl-1H-imidazol-4-yl)-2-[(3R)-3-methylmorpholin-4-yl]-8-(1H-pyrazol-5-yl)-1,7-naphthyridine
1-{2-[(3R)-3-methylmorpholin-4-yl]-8-(1H-pyrazol-5-yl)-1,7-naphthyridin-4-yl}prolinamide
3-{2-[(3R)-3-methylmorpholin-4-yl]-8-(1H-pyrazol-5-yl)-1,7-naphthyridin-4-yl}pyridin-2-amine
2-[(3R)-3-methylmorpholin-4-yl]-8-(1H-pyrazol-5-yl)-4-[1-(2,2,2-trifluoroethyl)-1H-pyrazol-5-yl]-1,7-naphthyridine
1-methyl-4-{2-[(3R)-3-methylmorpholin-4-yl]-8-(1H-pyrazol-5-yl)-1,7-naphthyridin-4-yl}piperazin-2-one
4-[1-(2-fluoroethyl)-1H-pyrazol-3-yl]-2-[(3R)-3-methylmorpholin-4-yl]-8-(1H-pyrazol-5-yl)-1,7-naphthyridine
4-[1-(2-fluoroethyl)-1H-pyrazol-5-yl]-2-[(3R)-3-methylmorpholin-4-yl]-8-(1H-pyrazol-5-yl)-1,7-naphthyridine
2-(3-{2-[(3R)-3-methylmorpholin-4-yl]-8-(1H-pyrazol-5-yl)-1,7-naphthyridin-4-yl}-1H-pyrazol-1-yl)ethanol
2-methyl-1-(3-{2-[(3R)-3-methylmorpholin-4-yl]-8-(1H-pyrazol-5-yl)-1,7-naphthyridin-4-yl}-1H-pyrazol-1-yl)propan-2-ol
4-[(2R)-2-methylmorpholin-4-yl]-2-(morpholin-4-yl)-8-(1H-pyrazol-5-yl)-1,7-naphthyridine
4-(5-fluoropyridin-2-yl)-2-[(3R)-3-methylmorpholin-4-yl]-8-(1H-pyrazol-5-yl)-1,7-naphthyridine
2-[(3R)-3-methylmorpholin-4-yl]-4-(6-methylpyridin-2-yl)-8-(1H-pyrazol-5-yl)-1,7-naphthyridine
2-[(3R)-3-methylmorpholin-4-yl]-4-(3-methylpyridin-2-yl)-8-(1H-pyrazol-5-yl)-1,7-naphthyridine
N-(2-{2-[(3R)-3-methylmorpholin-4-yl]-8-(1H-pyrazol-5-yl)-1,7-naphthyridin-4-yl}phenyl) acetamide
3-{2-[(3R)-3-methylmorpholin-4-yl]-8-(1H-pyrazol-5-yl)-1,7-naphthyridin-4-yl}pyridin-2-ol
2-(3-{2-[(3R)-3-methylmorpholin-4-yl]-8-(1H-pyrazol-5-yl)-1,7-naphthyridin-4-yl}phenyl)propan-2-ol
4-(5,6-dihydroimidazo[1,2-a]pyrazin-7(8H)-yl)-2-(morpholin-4-yl)-8-(1H-pyrazol-5-yl)-1,7-naphthyridine
4-[(2S)-2-methylmorpholin-4-yl]-2-(morpholin-4-yl)-8-(1H-pyrazol-5-yl)-1,7-naphthyridine
4-[(trans)-2-methylcyclopropyl]-2-[(3R)-3-methylmorpholin-4-yl]-8-(1H-pyrazol-5-yl)-1,7-naphthyridine
4-(difluoromethoxy)-2-[(3R)-3-methylmorpholin-4-yl]-8-(1H-pyrazol-5-yl)-1,7-naphthyridine
2-[2-(morpholin-4-yl)-8-(1H-pyrazol-5-yl)-1,7-naphthyridin-4-yl]propan-2-ol
2-(morpholin-4-yl)-4-(3-oxa-8-azabicyclo[3.2.1]oct-8-yl)-8-(1H-pyrazol-5-yl)-1,7-naphthyridine
2-[(3R)-3-methylmorpholin-4-yl]-8-(1H-pyrazol-5-yl)-4-(pyrrolidin-1-yl)-1,7-naphthyridine
4-[2-(morpholin-4-yl)-8-(1H-pyrazol-5-yl)-1,7-naphthyridin-4-yl]piperazin-2-one
4-(dimethylphosphoryl)-2-(morpholin-4-yl)-8-(1H-pyrazol-5-yl)-1,7-naphthyridine
4-[(trans)-2,5-dimethylpiperazin-1-yl]-2-(morpholin-4-yl)-8-(1H-pyrazol-5-yl)-1,7-naphthyridine
4-[(cis)-3,5-dimethylpiperazin-1-yl]-2-(morpholin-4-yl)-8-(1H-pyrazol-5-yl)-1,7-naphthyridine
1-[2-(morpholin-4-yl)-8-(1H-pyrazol-5-yl)-1,7-naphthyridin-4-yl]-3-(trifluoromethyl)azetidin-3-ol
methyl hydrogen{4-[2-(morpholin-4-yl)-8-(1H-pyrazol-5-yl)-1,7-naphthyridin-4-yl]phenyl}phosphonate 4-(4-methylpiperazin-1-yl)-2-(morpholin-4-yl)-8-(1H-pyrazol-5-yl)-1,7-naphthyridine
2-(morpholin-4-yl)-8-(1H-pyrazol-5-yl)-4-[(3aR,6aS)-tetrahydro-1H-furo[3,4-c]pyrrol-5(3H)-yl]-1,7-naphthyridine
4-(3-methoxy-3-methylazetidin-1-yl)-2-(morpholin-4-yl)-8-(1H-pyrazol-5-yl)-1,7-naphthyridine
2-(morpholin-4-yl)-4-[(1S,4S)-2-oxa-5-azabicyclo[2.2.1]hept-5-yl]-8-(1H-pyrazol-5-yl)-1,7-naphthyridine
2-[(3R)-3-methylmorpholin-4-yl]-4-[(methylsulfanyl)methyl]-8-(1H-pyrazol-5-yl)-1,7-naphthyridine
N,N-dimethyl-5-[2-(morpholin-4-yl)-8-(1H-pyrazol-5-yl)-1,7-naphthyridin-4-yl]pyridin-2-amine
4-(2-methylpyridin-4-yl)-2-(morpholin-4-yl)-8-(1H-pyrazol-5-yl)-1,7-naphthyridine
1-{2-[(3R)-3-methylmorpholin-4-yl]-8-(1H-pyrazol-5-yl)-1,7-naphthyridin-4-yl}cyclohexanol
2-fluoro-6-{2-[(3R)-3-methylmorpholin-4-yl]-8-(1H-pyrazol-5-yl)-1,7-naphthyridin-4-yl}aniline
(methyl{4-[2-(morpholin-4-yl)-8-(1H-pyrazol-5-yl)-1,7-naphthyridin-4-yl]phenyl}oxido-$\lambda^6$-sulfanylidene)cyanamide
1-ethyl-3-(methyl{4-[2-(morpholin-4-yl)-8-(1H-pyrazol-5-yl)-1,7-naphthyridin-4-yl]phenyl}oxido-$\lambda^6$-sulfanylidene)urea
3-({2-[(3R)-3-methylmorpholin-4-yl]-8-(1H-pyrazol-5-yl)-1,7-naphthyridin-4-yl}oxy)propan-1-amine
4-(4-cyclopropyl-1H-1,2,3-triazol-5-yl)-2-[(3R)-3-methylmorpholin-4-yl]-8-(1H-pyrazol-5-yl)-1,7-naphthyridine
4-ethylsulfinyl-2-(morpholin-4-yl)-8-(1H-pyrazol-5-yl)-1,7-naphthyridine
2-(morpholin-4-yl)-4-[propan-2-ylsulfinyl]-8-(1H-pyrazol-5-yl)-1,7-naphthyridine
2-[(3R)-3-methylmorpholin-4-yl]-4-[3-(methylsulfonyl)propoxy]-8-(1H-pyrazol-5-yl)-1,7-naphthyridine
2-(morpholin-4-yl)-4-(phenylsulfonyl)-8-(1H-pyrazol-5-yl)-1,7-naphthyridine
2-(morpholin-4-yl)-4-(propan-2-ylsulfonyl)-8-(1H-pyrazol-5-yl)-1,7-naphthyridine
4-(ethylsulfonyl)-2-(morpholin-4-yl)-8-(1H-pyrazol-5-yl)-1,7-naphthyridine
2-(morpholin-4-yl)-4-(phenylsulfinyl)-8-(1H-pyrazol-5-yl)-1,7-naphthyridine
4-(methylsulfinyl)-2-(morpholin-4-yl)-8-(1H-pyrazol-5-yl)-1,7-naphthyridine
2-[(3R)-3-methylmorpholin-4-yl]-4-[1-oxidotetrahydro-2H-thiopyran-4-yl]-8-(1H-pyrazol-5-yl)-1,7-naphthyridine
4-(1,1-dioxidotetrahydro-2H-thiopyran-4-yl)-2-[(3R)-3-methylmorpholin-4-yl]-8-(1H-pyrazol-5-yl)-1,7-naphthyridine
2-[(3R)-3-methylmorpholin-4-yl]-4,8-di(1H-pyrazol-5-yl)-1,7-naphthyridine
N,N-dimethyl-2-(morpholin-4-yl)-8-(1H-pyrazol-5-yl)-1,7-naphthyridin-4-amine
2-(morpholin-4-yl)-4-(phenylsulfanyl)-8-(1H-pyrazol-5-yl)-1,7-naphthyridine
2-(morpholin-4-yl)-N-(propan-2-yl)-8-(1H-pyrazol-5-yl)-1,7-naphthyridin-4-amine
4-(ethylsulfanyl)-2-(morpholin-4-yl)-8-(1H-pyrazol-5-yl)-1,7-naphthyridine
2-(morpholin-4-yl)-4-(propan-2-ylsulfanyl)-8-(1H-pyrazol-5-yl)-1,7-naphthyridine
2-(morpholin-4-yl)-8-(1H-pyrazol-5-yl)-4-(1H-pyrrol-2-yl)-1,7-naphthyridine
2-(morpholin-4-yl)-8-(1H-pyrazol-5-yl)-4-(1H-pyrrol-3-yl)-1,7-naphthyridine
4-[(4-methoxyphenyl)sulfanyl]-2-(morpholin-4-yl)-8-(1H-pyrazol-5-yl)-1,7-naphthyridine
4-(5-methyl-1H-pyrazol-3-yl)-2-(morpholin-4-yl)-8-(1H-pyrazol-5-yl)-1,7-naphthyridine
1-[2-(morpholin-4-yl)-8-(1H-pyrazol-5-yl)-1,7-naphthyridin-4-yl]pyrrolidin-2-one
4-(1,1-dioxido-1,2-thiazolidin-2-yl)-2-(morpholin-4-yl)-8-(1H-pyrazol-5-yl)-1,7-naphthyridine
1-[2-(morpholin-4-yl)-8-(1H-pyrazol-5-yl)-1,7-naphthyridin-4-yl]piperidin-2-one
2-[(3R)-3-methylmorpholin-4-yl]-4-(2-methylpyridin-3-yl)-8-(1H-pyrazol-5-yl)-1,7-naphthyridine
2-[(3R)-3-methylmorpholin-4-yl]-4-[2-(propan-2-yloxy)pyridin-3-yl]-8-(1H-pyrazol-5-yl)-1,7-naphthyridine
4-(2-methoxypyridin-3-yl)-2-[(3R)-3-methylmorpholin-4-yl]-8-(1H-pyrazol-5-yl)-1,7-naphthyridine
2-(morpholin-4-yl)-8-(1H-pyrazol-5-yl)-4-(pyridin-4-yl)-1,7-naphthyridine
4-[(4-methoxyphenyl)sulfanyl]-2-[(3R)-3-methylmorpholin-4-yl]-8-(1H-pyrazol-5-yl)-1,7-naphthyridine
4-[3-fluoro-2-(morpholin-4-yl)pyridin-4-yl]-2-[(3R)-3-methylmorpholin-4-yl]-8-(1H-pyrazol-5-yl)-1,7-naphthyridine
4-(6-fluoro-5-methylpyridin-3-yl)-2-(morpholin-4-yl)-8-(1H-pyrazol-5-yl)-1,7-naphthyridine
3-[2-(morpholin-4-yl)-8-(1H-pyrazol-5-yl)-1,7-naphthyridin-4-yl]-1,3-oxazinan-2-one
3-[2-(morpholin-4-yl)-8-(1H-pyrazol-5-yl)-1,7-naphthyridin-4-yl]-1,3-oxazolidin-2-one
4-(3-methoxypyridin-4-yl)-2-[(3R)-3-methylmorpholin-4-yl]-8-(1H-pyrazol-5-yl)-1,7-naphthyridine
4-(2,6-difluoropyridin-3-yl)-2-[(3R)-3-methylmorpholin-4-yl]-8-(1H-pyrazol-5-yl)-1,7-naphthyridine
4-(5-chloro-2-fluoropyridin-3-yl)-2-[(3R)-3-methylmorpholin-4-yl]-8-(1H-pyrazol-5-yl)-1,7-naphthyridine
4-(3-fluoropyridin-4-yl)-2-[(3R)-3-methylmorpholin-4-yl]-8-(1H-pyrazol-5-yl)-1,7-naphthyridine
4-(2-chloro-6-methylpyridin-3-yl)-2-[(3R)-3-methylmorpholin-4-yl]-8-(1H-pyrazol-5-yl)-1,7-naphthyridine
4-(5,6-dimethylpyridin-3-yl)-2-[(3R)-3-methylmorpholin-4-yl]-8-(1H-pyrazol-5-yl)-1,7-naphthyridine
4-(5-fluoro-6-methylpyridin-3-yl)-2-[(3R)-3-methylmorpholin-4-yl]-8-(1H-pyrazol-5-yl)-1,7-naphthyridine
2-[(3R)-3-methylmorpholin-4-yl]-4-(5-methylthiophen-3-yl)-8-(1H-pyrazol-5-yl)-1,7-naphthyridine
4-(3-methoxythiophen-2-yl)-2-[(3R)-3-methylmorpholin-4-yl]-8-(1H-pyrazol-5-yl)-1,7-naphthyridine
4-(2-chlorothiophen-3-yl)-2-[(3R)-3-methylmorpholin-4-yl]-8-(1H-pyrazol-5-yl)-1,7-naphthyridine
4-(isoquinolin-4-yl)-2-[(3R)-3-methylmorpholin-4-yl]-8-(1H-pyrazol-5-yl)-1,7-naphthyridine
4-(5-chlorothiophen-2-yl)-2-[(3R)-3-methylmorpholin-4-yl]-8-(1H-pyrazol-5-yl)-1,7-naphthyridine
2-[(3R)-3-methylmorpholin-4-yl]-4-(4-methylthiophen-2-yl)-8-(1H-pyrazol-5-yl)-1,7-naphthyridine
4-(2,5-dimethylthiophen-3-yl)-2-[(3R)-3-methylmorpholin-4-yl]-8-(1H-pyrazol-5-yl)-1,7-naphthyridine
2-[(3R)-3-methylmorpholin-4-yl]-8-(1H-pyrazol-5-yl)-4-(tetrahydro-2H-thiopyran-4-yl)-1,7-naphthyridine
2-[(3R)-3-methylmorpholin-4-yl]-4-(1-methyl-1,2,5,6-tetrahydropyridin-3-yl)-8-(1H-pyrazol-5-yl)-1,7-naphthyridine
2-[(3R)-3-methylmorpholin-4-yl]-4-(1-methyl-1,2,3,6-tetrahydropyridin-4-yl)-8-(1H-pyrazol-5-yl)-1,7-naphthyridine
2-[(3R)-3-methylmorpholin-4-yl]-4-[1-methylpiperidin-3-yl]-8-(1H-pyrazol-5-yl)-1,7-naphthyridine
2-[(3R)-3-methylmorpholin-4-yl]-8-(1H-pyrazol-5-yl)-4-(1,2,3,6-tetrahydropyridin-4-yl)-1,7-naphthyridine 2-[(3R)-3-methylmorpholin-4-yl]-8-(1H-pyrazol-5-yl)-4-[1-(tetrahydro-2H-pyran-4-yl)-1H-pyrazol-3-yl]-1,7-naphthyridine
4-(4,6-difluoropyridin-3-yl)-2-[(3R)-3-methylmorpholin-4-yl]-8-(1H-pyrazol-5-yl)-1,7-naphthyridine
2-[(3R)-3-methylmorpholin-4-yl]-4-(1-methyl-1H-pyrazol-4-yl)-8-(1H-pyrazol-5-yl)-1,7-naphthyridine
4-(1,3-dimethyl-1H-pyrazol-4-yl)-2-[(3R)-3-methylmorpholin-4-yl]-8-(1H-pyrazol-5-yl)-1,7-naphthyridine
4-(1,5-dimethyl-1H-pyrazol-4-yl)-2-[(3R)-3-methylmorpholin-4-yl]-8-(1H-pyrazol-5-yl)-1,7-naphthyridine
2-[(3R)-3-methylmorpholin-4-yl]-4-(piperidin-4-yl)-8-(1H-pyrazol-5-yl)-1,7-naphthyridine
2-[(3R)-3-methylmorpholin-4-yl]-8-(1H-pyrazol-5-yl)-4-[3-(trifluoromethyl)-1H-pyrazol-4-yl]-1,7-naphthyridine
4-(1-cyclobutyl-1H-pyrazol-4-yl)-2-[(3R)-3-methylmorpholin-4-yl]-8-(1H-pyrazol-5-yl)-1,7-naphthyridine
4-(1-cyclopropyl-1H-pyrazol-4-yl)-2-[(3R)-3-methylmorpholin-4-yl]-8-(1H-pyrazol-5-yl)-1,7-naphthyridine
2-[(3R)-3-methylmorpholin-4-yl]-4-[1-(propan-2-yl)-1H-pyrazol-4-yl]-8-(1H-pyrazol-5-yl)-1,7-naphthyridine
4-[1-(difluoromethyl)-1H-pyrazol-4-yl]-2-[(3R)-3-methylmorpholin-4-yl]-8-(1H-pyrazol-5-yl)-1,7-naphthyridine
4-(1-tert-butyl-1H-pyrazol-4-yl)-2-[(3R)-3-methylmorpholin-4-yl]-8-(1H-pyrazol-5-yl)-1,7-naphthyridine
2-[(3R)-3-methylmorpholin-4-yl]-8-(1H-pyrazol-5-yl)-4-(1,3,5-trimethyl-1H-pyrazol-4-yl)-1,7-naphthyridine
2-[(3R)-3-methylmorpholin-4-yl]-4-[1-methyl-3-(trifluoromethyl)-1H-pyrazol-4-yl]-8-(1H-pyrazol-5-yl)-1,7-naphthyridine
2-(4-{2-[(3R)-3-methylmorpholin-4-yl]-8-(1H-pyrazol-5-yl)-1,7-naphthyridin-4-yl}-1H-pyrazol-1-yl)ethanol
4-(1-ethyl-1H-pyrazol-4-yl)-2-[(3R)-3-methylmorpholin-4-yl]-8-(1H-pyrazol-5-yl)-1,7-naphthyridine
2-[(3R)-3-methylmorpholin-4-yl]-4-(1-methyl-1H-pyrrol-3-yl)-8-(1H-pyrazol-5-yl)-1,7-naphthyridine
2-[(3R)-3-methylmorpholin-4-yl]-4-[1-(propan-2-yl)-1H-pyrazol-3-yl]-8-(1H-pyrazol-5-yl)-1,7-naphthyridine
2-[(3R)-3-methylmorpholin-4-yl]-8-(1H-pyrazol-5-yl)-4-(1,2,5-trimethyl-1H-pyrrol-3-yl)-1,7-naphthyridine
2-[(3R)-3-methylmorpholin-4-yl]-4-(1-phenyl-1H-pyrazol-4-yl)-8-(1H-pyrazol-5-yl)-1,7-naphthyridine
2-[(3R)-3-methylmorpholin-4-yl]-4-(3-methyl-1H-pyrazol-4-yl)-8-(1H-pyrazol-5-yl)-1,7-naphthyridine
2-[(3R)-3-methylmorpholin-4-yl]-8-(1H-pyrazol-5-yl)-1,7-naphthyridin-4-amine
2-[(3R)-3-methylmorpholin-4-yl]-4-[1-(2-methylpropyl)-1H-pyrazol-4-yl]-8-(1H-pyrazol-5-yl)-1,7-naphthyridine
2-[(3R)-3-methylmorpholin-4-yl]-4-(1H-pyrazol-4-yl)-8-(1H-pyrazol-5-yl)-1,7-naphthyridine
2-[(3R)-3-methylmorpholin-4-yl]-4-(1,3-oxazol-2-yl)-8-(1H-pyrazol-5-yl)-1,7-naphthyridine
4-(1,3-dimethyl-1H-pyrazol-4-yl)-2-(morpholin-4-yl)-8-(1H-pyrazol-5-yl)-1,7-naphthyridine
4-(1,5-dimethyl-1H-pyrazol-4-yl)-2-(morpholin-4-yl)-8-(1H-pyrazol-5-yl)-1,7-naphthyridine
2-(morpholin-4-yl)-8-(1H-pyrazol-5-yl)-4-(1,3,5-trimethyl-1H-pyrazol-4-yl)-1,7-naphthyridine
4-{[(2-methoxyethyl)(methyl)oxido-$\lambda^6$-sulfanylidene]amino}-2-[(3R)-3-methylmorpholin-4-yl]-8-(1H-pyrazol-5-yl)-1,7-naphthyridine
4-{[(4-bromophenyl)(oxido)propan-2-yl-$\lambda^6$-sulfanylidene]amino}-2-[(3R)-3-methylmorpholin-4-yl]-8-(1H-pyrazol-5-yl)-1,7-naphthyridine
2-(methyl-N-{2-[(3R)-3-methylmorpholin-4-yl]-8-(1H-pyrazol-5-yl)-1,7-naphthyridin-4-yl}sulfonimidoyl)phenol
4-{[(4-bromophenyl)(methyl)oxido-$\lambda^6$-sulfanylidene]amino}-2-[(3R)-3-methylmorpholin-4-yl]-8-(1H-pyrazol-5-yl)-1,7-naphthyridine
4-{[tert-butyl(methyl)oxido-$\lambda^6$-sulfanylidene]amino}-2-[(3R)-3-methylmorpholin-4-yl]-8-(1H-pyrazol-5-yl)-1,7-naphthyridine
formic acid-N-[2-(morpholin-4-yl)-8-(1H-pyrazol-5-yl)-1,7-naphthyridin-4-yl]-1,4$\lambda^4$-oxathian-4-imine 4-oxide (1:1)
N-[2-(morpholin-4-yl)-8-(1H-pyrazol-5-yl)-1,7-naphthyridin-4-yl]hexahydro-1$\lambda^4$-thiopyran-1-imine 1-oxide
3-methyl-2-{2-[(3R)-3-methylmorpholin-4-yl]-8-(1H-pyrazol-5-yl)-1,7-naphthyridin-4-yl}butan-2-ol
1-{2-[(3R)-3-methylmorpholin-4-yl]-8-(1H-pyrazol-5-yl)-1,7-naphthyridin-4-yl}-1-(tetrahydro-2H-pyran-4-yl)ethanol
3,3-dimethyl-2-{2-[(3R)-3-methylmorpholin-4-yl]-8-(1H-pyrazol-5-yl)-1,7-naphthyridin-4-yl}butan-2-ol
2-{2-[(3R)-3-methylmorpholin-4-yl]-8-(1H-pyrazol-5-yl)-1,7-naphthyridin-4-yl}hexan-2-ol
2-[(3R)-3-methylmorpholin-4-yl]-8-(1H-pyrazol-3-yl)-1,7-naphthyridine-4-carboxamide
2-[(3R)-3-methylmorpholin-4-yl]-4-[1-(methylsulfonyl)cyclopropyl]-8-(1H-pyrazol-5-yl)-1,7-naphthyridine
2-(morpholin-4-yl)-8-(1H-pyrazol-5-yl)-4-(tetrahydro-2H-pyran-4-ylmethoxy)-1,7-naphthyridine
N,N-dimethyl-3-[2-(morpholin-4-yl)-8-(1H-pyrazol-5-yl)-1,7-naphthyridin-4-yl]benzamide
{4-[2-(morpholin-4-yl)-8-(1H-pyrazol-5-yl)-1,7-naphthyridin-4-yl]phenyl}(piperidin-1-yl)methanone
N,N-dimethyl-2-[2-(morpholin-4-yl)-8-(1H-pyrazol-5-yl)-1,7-naphthyridin-4-yl]benzamide
N-cyclopropyl-4-[2-(morpholin-4-yl)-8-(1H-pyrazol-5-yl)-1,7-naphthyridin-4-yl]benzamide
4-(4-methylpyridin-3-yl)-2-(morpholin-4-yl)-8-(1H-pyrazol-5-yl)-1,7-naphthyridine
4-(1H-indol-6-yl)-2-(morpholin-4-yl)-8-(1H-pyrazol-5-yl)-1,7-naphthyridine
4-(1H-indol-4-yl)-2-(morpholin-4-yl)-8-(1H-pyrazol-5-yl)-1,7-naphthyridine
3-[2-(morpholin-4-yl)-8-(1H-pyrazol-5-yl)-1,7-naphthyridin-4-yl]benzamide
4-[2-(morpholin-4-yl)-8-(1H-pyrazol-5-yl)-1,7-naphthyridin-4-yl]benzamide
N-methyl-3-[2-(morpholin-4-yl)-8-(1H-pyrazol-5-yl)-1,7-naphthyridin-4-yl]benzamide
4-(3-fluorophenyl)-2-(morpholin-4-yl)-8-(1H-pyrazol-5-yl)-1,7-naphthyridine
4-(5-chlorothiophen-2-yl)-2-(morpholin-4-yl)-8-(1H-pyrazol-5-yl)-1,7-naphthyridine
4-(2-methoxyphenyl)-2-(morpholin-4-yl)-8-(1H-pyrazol-5-yl)-1,7-naphthyridine
2-(morpholin-4-yl)-8-(1H-pyrazol-5-yl)-4-[2-(trifluoromethyl)phenyl]-1,7-naphthyridine
2-(morpholin-4-yl)-8-(1H-pyrazol-5-yl)-4-[4-(trifluoromethyl)phenyl]-1,7-naphthyridine
2-(morpholin-4-yl)-8-(1H-pyrazol-5-yl)-4-[3-(trifluoromethyl)phenyl]-1,7-naphthyridine
4-(3-chlorophenyl)-2-(morpholin-4-yl)-8-(1H-pyrazol-5-yl)-1,7-naphthyridine
N-{3-[2-(morpholin-4-yl)-8-(1H-pyrazol-5-yl)-1,7-naphthyridin-4-yl]phenyl}acetamide
4-(3-methoxyphenyl)-2-(morpholin-4-yl)-8-(1H-pyrazol-5-yl)-1,7-naphthyridine
4-(3,5-dimethoxyphenyl)-2-(morpholin-4-yl)-8-(1H-pyrazol-5-yl)-1,7-naphthyridine 4-(3-methylphenyl)-2-(morpholin-4-yl)-8-(1H-pyrazol-5-yl)-1,7-naphthyridine
4-(4-methoxyphenyl)-2-(morpholin-4-yl)-8-(1H-pyrazol-5-yl)-1,7-naphthyridine
4-(furan-2-ylmethyl)-2-(morpholin-4-yl)-8-(1H-pyrazol-5-yl)-1,7-naphthyridine
2,6-dimethyl-4-[2-(morpholin-4-yl)-8-(1H-pyrazol-5-yl)-1,7-naphthyridin-4-yl]phenol
4-(2,3-dimethylphenyl)-2-(morpholin-4-yl)-8-(1H-pyrazol-5-yl)-1,7-naphthyridine
{3-[2-(morpholin-4-yl)-8-(1H-pyrazol-5-yl)-1,7-naphthyridin-4-yl]phenyl}methanol
4-(4-fluorophenyl)-2-(morpholin-4-yl)-8-(1H-pyrazol-5-yl)-1,7-naphthyridine
4-(4-methylphenyl)-2-(morpholin-4-yl)-8-(1H-pyrazol-5-yl)-1,7-naphthyridine
4-(4-chlorophenyl)-2-(morpholin-4-yl)-8-(1H-pyrazol-5-yl)-1,7-naphthyridine
4-(2-fluoro-3-methoxyphenyl)-2-(morpholin-4-yl)-8-(1H-pyrazol-5-yl)-1,7-naphthyridine
4-(2-methylphenyl)-2-(morpholin-4-yl)-8-(1H-pyrazol-5-yl)-1,7-naphthyridine
4-(2,3-dimethoxyphenyl)-2-(morpholin-4-yl)-8-(1H-pyrazol-5-yl)-1,7-naphthyridine
N,N-dimethyl-3-[2-(morpholin-4-yl)-8-(1H-pyrazol-5-yl)-1,7-naphthyridin-4-yl]aniline
N,N-dimethyl-2-[2-(morpholin-4-yl)-8-(1H-pyrazol-5-yl)-1,7-naphthyridin-4-yl]aniline
N-{2-[2-(morpholin-4-yl)-8-(1H-pyrazol-5-yl)-1,7-naphthyridin-4-yl]phenyl}methanesulfonamide
N-{4-[2-(morpholin-4-yl)-8-(1H-pyrazol-5-yl)-1,7-naphthyridin-4-yl]phenyl}methanesulfonamide
N,N-dimethyl-4-[2-(morpholin-4-yl)-8-(1H-pyrazol-5-yl)-1,7-naphthyridin-4-yl]benzamide
2-(morpholin-4-yl)-4-[(1E)-prop-1-en-1-yl]-8-(1H-pyrazol-5-yl)-1,7-naphthyridine
4-[2-(morpholin-4-yl)-8-(1H-pyrazol-5-yl)-1,7-naphthyridin-4-yl]phenol
4-(2-fluorophenyl)-2-(morpholin-4-yl)-8-(1H-pyrazol-5-yl)-1,7-naphthyridine
{3-[2-(morpholin-4-yl)-8-(1H-pyrazol-5-yl)-1,7-naphthyridin-4-yl]phenyl}(piperidin-1-yl)methanone
2-(morpholin-4-yl)-4-[4-(propan-2-yl)phenyl]-8-(1H-pyrazol-5-yl)-1,7-naphthyridine
N-cyclopropyl-3-[2-(morpholin-4-yl)-8-(1H-pyrazol-5-yl)-1,7-naphthyridin-4-yl]benz amide
4-(biphenyl-4-yl)-2-(morpholin-4-yl)-8-(1H-pyrazol-5-yl)-1,7-naphthyridine
4-(2,4-dimethoxyphenyl)-2-(morpholin-4-yl)-8-(1H-pyrazol-5-yl)-1,7-naphthyridine
4-(2-chlorophenyl)-2-(morpholin-4-yl)-8-(1H-pyrazol-5-yl)-1,7-naphthyridine
4-(2,5-dimethylphenyl)-2-(morpholin-4-yl)-8-(1H-pyrazol-5-yl)-1,7-naphthyridine
3-[2-(morpholin-4-yl)-8-(1H-pyrazol-5-yl)-1,7-naphthyridin-4-yl]aniline
2-(morpholin-4-yl)-8-(1H-pyrazol-5-yl)-4-[3-(1H-pyrazol-1-yl)phenyl]-1,7-naphthyridine
3-[2-(morpholin-4-yl)-8-(1H-pyrazol-5-yl)-1,7-naphthyridin-4-yl]phenol
4-(2-fluoro-5-methoxyphenyl)-2-(morpholin-4-yl)-8-(1H-pyrazol-5-yl)-1,7-naphthyridine
4-(5-fluoro-2-methoxyphenyl)-2-(morpholin-4-yl)-8-(1H-pyrazol-5-yl)-1,7-naphthyridine
4-(2,4-difluorophenyl)-2-(morpholin-4-yl)-8-(1H-pyrazol-5-yl)-1,7-naphthyridine
4-(2,3-difluorophenyl)-2-(morpholin-4-yl)-8-(1H-pyrazol-5-yl)-1,7-naphthyridine
4-(2,6-dimethoxyphenyl)-2-(morpholin-4-yl)-8-(1H-pyrazol-5-yl)-1,7-naphthyridine
2-[2-(morpholin-4-yl)-8-(1H-pyrazol-5-yl)-1,7-naphthyridin-4-yl]aniline
4-(3,5-dichlorophenyl)-2-(morpholin-4-yl)-8-(1H-pyrazol-5-yl)-1,7-naphthyridine
4-(biphenyl-2-yl)-2-(morpholin-4-yl)-8-(1H-pyrazol-5-yl)-1,7-naphthyridine
4-(2-chloropyridin-4-yl)-2-(morpholin-4-yl)-8-(1H-pyrazol-5-yl)-1,7-naphthyridine
4-(1-benzothiophen-2-yl)-2-(morpholin-4-yl)-8-(1H-pyrazol-5-yl)-1,7-naphthyridine
4-(1-methyl-1H-pyrazol-5-yl)-2-(morpholin-4-yl)-8-(1H-pyrazol-5-yl)-1,7-naphthyridine
2-(morpholin-4-yl)-8-(1H-pyrazol-5-yl)-4-(quinolin-5-yl)-1,7-naphthyridine
2-(morpholin-4-yl)-8-(1H-pyrazol-5-yl)-4-(pyridin-3-yl)-1,7-naphthyridine
4-(2-methoxypyridin-4-yl)-2-(morpholin-4-yl)-8-(1H-pyrazol-5-yl)-1,7-naphthyridine
4-(5-methylpyridin-3-yl)-2-(morpholin-4-yl)-8-(1H-pyrazol-5-yl)-1,7-naphthyridine
4-(5-methoxypyridin-3-yl)-2-(morpholin-4-yl)-8-(1H-pyrazol-5-yl)-1,7-naphthyridine
2-(morpholin-4-yl)-8-(1H-pyrazol-5-yl)-4-(quinolin-3-yl)-1,7-naphthyridine
2-(morpholin-4-yl)-4-[1-(phenylsulfonyl)-1H-indol-2-yl]-8-(1H-pyrazol-5-yl)-1,7-naphthyridine
4-(2-chloropyridin-3-yl)-2-(morpholin-4-yl)-8-(1H-pyrazol-5-yl)-1,7-naphthyridine
4-(6-chloropyridin-3-yl)-2-(morpholin-4-yl)-8-(1H-pyrazol-5-yl)-1,7-naphthyridine
{5-[2-(morpholin-4-yl)-8-(1H-pyrazol-5-yl)-1,7-naphthyridin-4-yl]thiophen-2-yl}methanol
4-(2-fluoropyridin-3-yl)-2-(morpholin-4-yl)-8-(1H-pyrazol-5-yl)-1,7-naphthyridine
4-(6-fluoropyridin-3-yl)-2-(morpholin-4-yl)-8-(1H-pyrazol-5-yl)-1,7-naphthyridine
4-(2-chloro-6-methylpyridin-3-yl)-2-(morpholin-4-yl)-8-(1H-pyrazol-5-yl)-1,7-naphthyridine
4-(2-methoxypyridin-3-yl)-2-(morpholin-4-yl)-8-(1H-pyrazol-5-yl)-1,7-naphthyridine
4-(isoquinolin-4-yl)-2-(morpholin-4-yl)-8-(1H-pyrazol-5-yl)-1,7-naphthyridine
4-(3-chloropyridin-4-yl)-2-(morpholin-4-yl)-8-(1H-pyrazol-5-yl)-1,7-naphthyridine
4-(3-fluoropyridin-4-yl)-2-(morpholin-4-yl)-8-(1H-pyrazol-5-yl)-1,7-naphthyridine
4-(2,6-difluoropyridin-3-yl)-2-(morpholin-4-yl)-8-(1H-pyrazol-5-yl)-1,7-naphthyridine
4-(1-methyl-1H-pyrazol-4-yl)-2-(morpholin-4-yl)-8-(1H-pyrazol-5-yl)-1,7-naphthyridine
tert-butyl 5-methoxy-2-[2-(morpholin-4-yl)-8-(1H-pyrazol-5-yl)-1,7-naphthyridin-4-yl]-1H-indole-1-carboxylate
2-(morpholin-4-yl)-4-[6-(morpholin-4-yl)pyridin-3-yl]-8-(1H-pyrazol-5-yl)-1,7-naphthyridine
4-(4-methylthiophen-3-yl)-2-(morpholin-4-yl)-8-(1H-pyrazol-5-yl)-1,7-naphthyridine
2-(morpholin-4-yl)-8-(1H-pyrazol-5-yl)-4-(thiophen-2-yl)-1,7-naphthyridine
2-(morpholin-4-yl)-8-(1H-pyrazol-5-yl)-4-(thiophen-3-yl)-1,7-naphthyridine
4-(3-methylthiophen-2-yl)-2-(morpholin-4-yl)-8-(1H-pyrazol-5-yl)-1,7-naphthyridine 4-(2-chloro-5-methylpyridin-3-yl)-2-(morpholin-4-yl)-8-(1H-pyrazol-5-yl)-1,7-naphthyridine
4-(4-methoxypyridin-3-yl)-2-(morpholin-4-yl)-8-(1H-pyrazol-5-yl)-1,7-naphthyridine
4-(5-chloro-2-methoxypyridin-3-yl)-2-(morpholin-4-yl)-8-(1H-pyrazol-5-yl)-1,7-naphthyridine
tert-butyl 5-methyl-2-[2-(morpholin-4-yl)-8-(1H-pyrazol-5-yl)-1,7-naphthyridin-4-yl]-1H-indole-1-carboxylate
4-(5-chloro-2-fluoropyridin-3-yl)-2-(morpholin-4-yl)-8-(1H-pyrazol-5-yl)-1,7-naphthyridine
4-(3,5-dimethyl-1,2-oxazol-4-yl)-2-(morpholin-4-yl)-8-(1H-pyrazol-5-yl)-1,7-naphthyridine
2-(morpholin-4-yl)-8-(1H-pyrazol-5-yl)-4-(quinolin-8-yl)-1,7-naphthyridine
4-(5-methylthiophen-2-yl)-2-(morpholin-4-yl)-8-(1H-pyrazol-5-yl)-1,7-naphthyridine
4-(6-ethoxypyridin-3-yl)-2-(morpholin-4-yl)-8-(1H-pyrazol-5-yl)-1,7-naphthyridine
4-(2-ethoxypyridin-3-yl)-2-(morpholin-4-yl)-8-(1H-pyrazol-5-yl)-1,7-naphthyridine
2-(morpholin-4-yl)-8-(1H-pyrazol-5-yl)-4-(quinolin-6-yl)-1,7-naphthyridine
4-(2-chlorothiophen-3-yl)-2-(morpholin-4-yl)-8-(1H-pyrazol-5-yl)-1,7-naphthyridine
5-[2-(morpholin-4-yl)-8-(1H-pyrazol-5-yl)-1,7-naphthyridin-4-yl]pyridin-2-amine
2-(morpholin-4-yl)-4-(1H-pyrazol-3-yl)-8-(1H-pyrazol-5-yl)-1,7-naphthyridine
4-(6-methylpyridin-3-yl)-2-(morpholin-4-yl)-8-(1H-pyrazol-5-yl)-1,7-naphthyridine
4-(1-methyl-1H-pyrrol-2-yl)-2-(morpholin-4-yl)-8-(1H-pyrazol-5-yl)-1,7-naphthyridine
5-[2-(morpholin-4-yl)-8-(1H-pyrazol-5-yl)-1,7-naphthyridin-4-yl]pyridin-2-ol
4-(5-chloropyridin-3-yl)-2-(morpholin-4-yl)-8-(1H-pyrazol-5-yl)-1,7-naphthyridine
4-(3-chloro-2-methoxypyridin-4-yl)-2-(morpholin-4-yl)-8-(1H-pyrazol-5-yl)-1,7-naphthyridine
4-(3-chlorothiophen-2-yl)-2-(morpholin-4-yl)-8-(1H-pyrazol-5-yl)-1,7-naphthyridine
4-(5-fluoropyridin-3-yl)-2-(morpholin-4-yl)-8-(1H-pyrazol-5-yl)-1,7-naphthyridine
4-[2-(methylsulfanyl)pyrimidin-5-yl]-2-(morpholin-4-yl)-8-(1H-pyrazol-5-yl)-1,7-naphthyridine
N-cyclopropyl-5-[2-(morpholin-4-yl)-8-(1H-pyrazol-5-yl)-1,7-naphthyridin-4-yl]pyrimidin-2-amine
4-(isoquinolin-5-yl)-2-(morpholin-4-yl)-8-(1H-pyrazol-5-yl)-1,7-naphthyridine
N-methyl-5-[2-(morpholin-4-yl)-8-(1H-pyrazol-5-yl)-1,7-naphthyridin-4-yl]pyridine-2-carboxamide
N-tert-butyl-5-[2-(morpholin-4-yl)-8-(1H-pyrazol-5-yl)-1,7-naphthyridin-4-yl]pyridine-3-carboxamide
4-[5-(methylsulfanyl)pyridin-3-yl]-2-(morpholin-4-yl)-8-(1H-pyrazol-5-yl)-1,7-naphthyridine
2-(morpholin-4-yl)-8-(1H-pyrazol-5-yl)-4-(1H-pyrrolo[2,3-b]pyridin-4-yl)-1,7-naphthyridine
3-[2-(morpholin-4-yl)-8-(1H-pyrazol-5-yl)-1,7-naphthyridin-4-yl]pyridin-2-amine
methyl 4-[2-(morpholin-4-yl)-8-(1H-pyrazol-5-yl)-1,7-naphthyridin-4-yl]thiophene-2-carboxylate
4-[2-methoxy-5-(trifluoromethyl)pyridin-3-yl]-2-(morpholin-4-yl)-8-(1H-pyrazol-5-yl)-1,7-naphthyridine
2-(morpholin-4-yl)-4-[2-(propan-2-yloxy)pyridin-3-yl]-8-(1H-pyrazol-5-yl)-1,7-naphthyridine
4-(5-chloro-6-ethoxypyridin-3-yl)-2-(morpholin-4-yl)-8-(1H-pyrazol-5-yl)-1,7-naphthyridine
4-(1-tert-butyl-1H-pyrazol-4-yl)-2-(morpholin-4-yl)-8-(1H-pyrazol-5-yl)-1,7-naphthyridine
2-(morpholin-4-yl)-4-(piperidin-1-yl)-8-(1H-pyrazol-5-yl)-1,7-naphthyridine
1-[2-(morpholin-4-yl)-8-(1H-pyrazol-5-yl)-1,7-naphthyridin-4-yl]piperidin-4-ol
N-methyl-2-(morpholin-4-yl)-N-phenyl-8-(1H-pyrazol-5-yl)-1,7-naphthyridin-4-amine
{1-[2-(morpholin-4-yl)-8-(1H-pyrazol-5-yl)-1,7-naphthyridin-4-yl]pyrrolidin-2-yl}methanol
N-methyl-2-(morpholin-4-yl)-N-propyl-8-(1H-pyrazol-5-yl)-1,7-naphthyridin-4-amine
4-(azepan-1-yl)-2-(morpholin-4-yl)-8-(1H-pyrazol-5-yl)-1,7-naphthyridine
4-(3-methylpiperidin-1-yl)-2-(morpholin-4-yl)-8-(1H-pyrazol-5-yl)-1,7-naphthyridine
4-(4-methylpiperidin-1-yl)-2-(morpholin-4-yl)-8-(1H-pyrazol-5-yl)-1,7-naphthyridine
1-[2-(morpholin-4-yl)-8-(1H-pyrazol-5-yl)-1,7-naphthyridin-4-yl]piperidine-3-carboxamide
4-(2,5-dihydro-1H-pyrrol-1-yl)-2-(morpholin-4-yl)-8-(1H-pyrazol-5-yl)-1,7-naphthyridine
4-(3,4-dihydroquinolin-1(2H)-yl)-2-(morpholin-4-yl)-8-(1H-pyrazol-5-yl)-1,7-naphthyridine
4-(3,4-dihydroisoquinolin-2(1H)-yl)-2-(morpholin-4-yl)-8-(1H-pyrazol-5-yl)-1,7-naphthyridine
4-(1,3-dihydro-2H-isoindol-2-yl)-2-(morpholin-4-yl)-8-(1H-pyrazol-5-yl)-1,7-naphthyridine
2-(morpholin-4-yl)-8-(1H-pyrazol-5-yl)-4-[1,3,3-trimethyl-6-azabicyclo[3.2.1]oct-6-yl]-1,7-naphthyridine
tert-butyl 1-[2-(morpholin-4-yl)-8-(1H-pyrazol-5-yl)-1,7-naphthyridin-4-yl]-prolinate
N-methyl-N-(2-methylpropyl)-2-(morpholin-4-yl)-8-(1H-pyrazol-5-yl)-1,7-naphthyridin-4-amine
N-(3-fluorophenyl)-N-methyl-2-(morpholin-4-yl)-8-(1H-pyrazol-5-yl)-1,7-naphthyridin-4-amine
4-(1,1-dioxido-1-thia-6-azaspiro[3.3]hept-6-yl)-2-(morpholin-4-yl)-8-(1H-pyrazol-5-yl)-1,7-naphthyridine
4-(3-fluoropiperidin-1-yl)-2-(morpholin-4-yl)-8-(1H-pyrazol-5-yl)-1,7-naphthyridine
N-(2-fluorophenyl)-N-methyl-2-(morpholin-4-yl)-8-(1H-pyrazol-5-yl)-1,7-naphthyridin-4-amine
1-[2-(morpholin-4-yl)-8-(1H-pyrazol-5-yl)-1,7-naphthyridin-4-yl]-prolinamide
{1-[2-(morpholin-4-yl)-8-(1H-pyrazol-5-yl)-1,7-naphthyridin-4-yl]piperidin-4-yl}methanol
4-(4-methoxypiperidin-1-yl)-2-(morpholin-4-yl)-8-(1H-pyrazol-5-yl)-1,7-naphthyridine
N-(4-fluorophenyl)-N-methyl-2-(morpholin-4-yl)-8-(1H-pyrazol-5-yl)-1,7-naphthyridin-4-amine
N-methyl-1-[2-(morpholin-4-yl)-8-(1H-pyrazol-5-yl)-1,7-naphthyridin-4-yl]-prolinamide
4-[4-(ethylsulfonyl)piperazin-1-yl]-2-(morpholin-4-yl)-8-(1H-pyrazol-5-yl)-1,7-naphthyridine
4-[4-(methylsulfonyl)piperazin-1-yl]-2-(morpholin-4-yl)-8-(1H-pyrazol-5-yl)-1,7-naphthyridine
N-cyclopropyl-N-methyl-2-(morpholin-4-yl)-8-(1H-pyrazol-5-yl)-1,7-naphthyridin-4-amine
N-(2,2-dimethylpropyl)-N-methyl-2-(morpholin-4-yl)-8-(1H-pyrazol-5-yl)-1,7-naphthyridin-4-amine
{1-[2-(morpholin-4-yl)-8-(1H-pyrazol-5-yl)-1,7-naphthyridin-4-yl]piperidin-3-yl}methanol
or a stereoisomer, a tautomer, an N-oxide, a hydrate, a solvate, or a pharmaceutically acceptable salt thereof.

The synthesis of the compounds of general formula (I) or (Ib) of component A listed above is described in International Patent Publication WO2016020320 (A1).

In a preferred embodiment, component A of the combination of the present invention is 2-[(3R)-3-methylmorpholin-4-yl]-4-(1-methyl-1H-pyrazol-5-yl)-8-(1H-pyrazol-5-yl)-1,7-naphthyridine ("Compound A"), or a stereoisomer, a tautomer, an N-oxide, a hydrate, a solvate, or a pharmaceutically acceptable salt thereof.

In another preferred embodiment, component A of the combination of the present invention is Compound A of structure

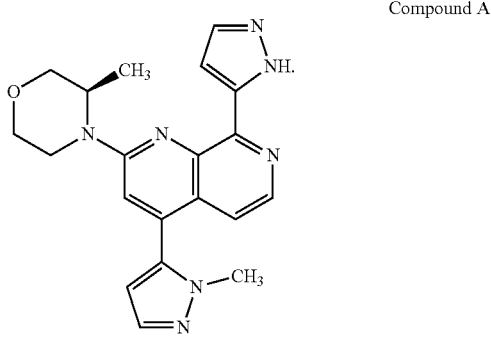

Compound A

The synthesis of Compound A is described in Example 111 of WO2016020320 (A1).

The term "pharmaceutically acceptable salt" of component A refers to a relatively non-toxic, inorganic or organic acid addition salt of a compound of the present invention. For example, see S. M. Berge, et al. "Pharmaceutical Salts," J. Pharm. Sci. 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and chorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

Representative salts of a component A of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, chloride, bromide, iodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, sulfate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine Additionally, basic nitrogen containing groups may be quaternized with such agents as lower alkyl halides such as methyl, ethyl, propyl, or butyl chlorides, bromides and iodides; dialkyl sulfates like dimethyl, diethyl, dibutyl sulfate, or diamyl sulfates, long chain halides such as decyl, lauryl, myristyl and strearyl chlorides, bromides and iodides, aralkyl halides like benzyl and phenethyl bromides and others.

Component A may be administered by the oral, intravenous, topical, local installations, intraperitoneal or nasal route.

Component A may be in the form of a pharmaceutical formulation which is ready for use to be administered simultaneously, concurrently, separately or sequentially with component B and optionally component C as further described infra. The components A and B and optionally C may be administered independently of one another by the oral, intravenous, topical, local installations, intraperitoneal or nasal route.

Component of the Combination

Component B of the combination of the present invention is a PD-1/PD-L1 inhibitor.

The term "PD-1/PD-L1 inhibitor" refers to a PD-1 inhibitor or to a PD-L1 inhibitor.

Particularly, the PD-1 inhibitor is an anti-PD-1 antibody including but not limited to nivolumab (Opdivo, BMS-936558, MDX1106), pembrolizumab (Keytruda, MK-3475, lambrolizumab), PDR-001, JS001, STI-A1110.

Particularly, the PD-L1 inhibitor is an anti-PD-L1 antibody including but not limited to atezolizumab (Tecentriq, MPDL3280A), durvalumab (MEDI4736), avelumab (MSB0010718C), BMS-936559 (MDX1105) and LY3300054.

According to another embodiment of the aspects of the present invention, component B is a "PD-1/PD-L1 inhibitor" selected from nivolumab (Opdivo, BMS-936558, MDX1106), pembrolizumab (Keytruda, MK-3475, lambrolizumab), PDR-001, JS001, STI-A1110, atezolizumab (Tecentriq, MPDL3280A), durvalumab (MEDI4736), avelumab (MSB0010718C), BMS-936559 (MDX1105) and LY3300054.

According to another embodiment of the aspects of the present invention, component B is a "PD-1 inhibitor" selected from nivolumab (Opdivo, BMS-936558, MDX1106), pembrolizumab (Keytruda, MK-3475, lambrolizumab), PDR-001, JS001, STI-A1110.

According to a preferred embodiment of the aspects of the present invention, component B is a PD-1 inhibitor selected from nivolumab and pembrolizumab.

According to a preferred embodiment of the aspects of the present invention, component B is pembrolizumab.

According to another embodiment of the present invention component B is the PD-1 inhibitor RMP1-14.

According to another embodiment of the aspects of the present invention, component B is a "PD-L1 inhibitor" selected from atezolizumab (Tecentriq, MPDL3280A), durvalumab (MEDI4736), avelumab (MSB0010718C), BMS-936559 (MDX1105) and LY3300054.

According to another embodiment of the aspects of the present invention, component B is a PD-L1 inhibitor selected from atezolizumab, durvalumab and avelumab, preferably component B is a PD-L1 inhibitor selected from atezolizumab and avelumab.

According to another embodiment of the aspects of the present invention, component B is atezolizumab.

According to another embodiment of the present invention component B is the PD-L1 inhibitor PPB-6721.

Nivolumab is a human IgG4 anti-PD-1 monoclonal antibody. For example it is used as a first line treatment for inoperable or metastatic melanoma in combination with ipilimumab if the cancer does not have a mutation in BRAF, as a second-line treatment following treatment with ipilimumab and if the cancer has a mutation in BRAF, with a BRAF inhibitor, as a second-line treatment for squamous non-small cell lung cancer, and as a second-line treatment for renal cell carcinoma.

Pembrolizumab is a humanized antibody which is for example indicated for the treatment of patients with unresectable or metastatic melanoma, as a single agent for the first-line treatment of patients with metastatic NSCLC whose tumors have high PD-L1 expression [(Tumor Proportion Score (TPS) ≥50%)] as determined by an FDA-approved test, with no EGFR or ALK genomic tumor aberrations, for the treatment of patients with recurrent or metastatic HNSCC with disease progression on or after platinum-containing chemotherapy.

PDR-001 is an intravenously administered anti-PD-1 antibody. In July 2017, Phase III trials for malignant melanoma, Phase II trials for nasopharyngeal cancer and for neuroendocrine tumors and Phase I/II trials for solid tumors and Phase I trials for hepatocellular carcinoma, lymphoma and colorectal cancer are ongoing.

JS001 is a recombinant humanised monoclonal antibody. Phase II development for melanoma and bladder cancer, Phase I/II trial for gastric cancer, nasopharyngeal cancer, oesophageal cancer and head and neck cancer and Phase I development in breast cancer, lymphoma, urogenital cancer, renal cancer, neuroendocrine tumors and solid tumors are ongoing in July 2017.

STI-A1110 is a lead monoclonal antibody (MAb) against programmed cell death protein 1 (PD-1), under development by Sorrento Therapeutics using its G-MAB fully human antibody library platform, for the treatment of cancer (Company presentation, Sorrento, 13 Mar. 2017, Slide 10, http://sorrentotherapeutics.com/wp-content/uploads/2017/03/Sorrento-Corporate-Presentation-ROTH-Mar-2017-FINAL.pdf; Company Web Page, Sorrento, 19 May 2017, http://sorrentotherapeutics.com/platforms/immuno-oncology-antibodies/). An initiation of clinical trial is expected in 2H 2017 (Company presentation, Sorrento, 1 Nov. 2016, Slide 7, http://sorrentotherapeutics.com/wp-content/uploads/2016/11/Sorrento-Corporate-Presentation-JefConf-FINAL.pdf).

Atezolizumab is a programmed death-ligand 1 (PD-L1) blocking antibody indicated for the treatment of patients with locally advanced or metastatic urothelial carcinoma who have disease progression during or following platinum-containing chemotherapy.

have disease progression within 12 months of neoadjuvant or adjuvant treatment with platinum-containing chemotherapy.

Atezolizumab is also indicated for the treatment of patients with metastatic non-small cell lung cancer who have disease progression during or following platinum-containing chemotherapy. Patients with EGFR or ALK genomic tumor aberrations should have disease progression on FDA-approved therapy for these aberrations prior to receiving Atezolizumab.

Durvalumab is a PD-L1 blocking antibody indicated for the treatment of patients with locally advanced or metastatic urothelial carcinoma who:

have disease progression during or following platinum-containing chemotherapy.

have disease progression within 12 months of neoadjuvant or adjuvant treatment with platinum-containing chemotherapy.

Avelumab is a PD-L1 blocking antibody indicated for the treatment of adults and pediatric patients 12 years and older with metastatic Merkel cell carcinoma (MCC).

BMS-936559 is a PD-L1 blocking antibody.

LY3300054 is a PD-L1 blocking antibody. Phase I development in solid tumors, Microsatellite Instability-High (MSI-H) solid tumors and in cutaneous melanoma are ongoing in July 2017.

Component B may be administered by the oral, intravenous, topical, local installations, intraperitoneal or nasal route.

Component B may be in the form of a pharmaceutical formulation which is ready for use to be administered simultaneously, concurrently, separately or sequentially with component A and optionally component C as further described infra. The components A and B and optionally C may be administered independently of one another by the oral, intravenous, topical, local installations, intraperitoneal or nasal route.

Combination

In accordance with another aspect, the present invention provides combinations of at least two components, preferably two components, component A and component B, component A being an inhibitor of ATR kinase, particularly an inhibitor of ATR kinase selected from VX-803, VX-970, AZD-6738, a compound of general formula (I) described infra, a compound of general formula (Ib) described infra and Compound A described infra, and component B being a PD-1/PD-L1 inhibitor, particularly a PD-1 inhibitor selected from nivolumab (Opdivo, BMS-936558, MDX1106), pembrolizumab (Keytruda, MK-3475, lambrolizumab), PDR-001, JS001 and STI-A1110, or, particularly a PD-L1 inhibitor selected from atezolizumab (Tecentriq, MPDL3280A), durvalumab (MEDI4736), avelumab (MSB0010718C), BMS-936559 (MDX1105) and LY3300054.

In accordance with another aspect, the present invention provides combinations of at least two components, preferably two components, component A and component B, component A being an inhibitor of ATR kinase, particularly Compound A, or a tautomer, an N-oxide, a hydrate, a solvate, or a pharmaceutically acceptable salt thereof, and component B being a PD-1/PD-L1 inhibitor, particularly a PD-1 inhibitor selected from nivolumab (Opdivo, BMS-936558, MDX1106), pembrolizumab (Keytruda, MK-3475, lambrolizumab), PDR-001 (spartalizumab), JS001 and STI-A1110, or, particularly a PD-L1 inhibitor selected from atezolizumab (Tecentriq, MPDL3280A), durvalumab (MEDI4736), avelumab (MSB0010718C), BMS-936559 (MDX1105) and LY3300054.

In accordance with another aspect, the present invention provides combinations of two components, component A and component B, component A being Compound A, or a tautomer, an N-oxide, a hydrate, a solvate, or a pharmaceutically acceptable salt thereof, and component B being a PD-1 inhibitor selected from nivolumab (Opdivo, BMS-936558, MDX1106), pembrolizumab (Keytruda, MK-3475, lambrolizumab), spartalizumab (PDR-001), JS001 and STI-A1110.

In accordance with another aspect, the present invention provides combinations of two components, component A and component B, component A being Compound A, or a tautomer, an N-oxide, a hydrate, a solvate, or a pharmaceutically acceptable salt thereof, and component B being nivolumab.

In accordance with another aspect, the present invention covers combinations of two components, component A and component B, component A being Compound A, or a tautomer, an N-oxide, a hydrate, a solvate, or a pharmaceutically acceptable salt thereof, and component B being pembrolizumab.

In accordance with another aspect, the present invention covers combinations of two components, component A and component B, component A being Compound A, or a tautomer, an N-oxide, a hydrate, a solvate, or a pharmaceutically acceptable salt thereof, and component B being spartalizumab.

In accordance with another aspect, the present invention covers combinations of two components, component A and component B, component A being Compound A, or a tautomer, an N-oxide, a hydrate, a solvate, or a pharmaceutically acceptable salt thereof, and component B being JS001.

In accordance with another aspect, the present invention covers combinations of two components, component A and component B, component A being Compound A, or a tautomer, an N-oxide, a hydrate, a solvate, or a pharmaceutically acceptable salt thereof, and component B being STI-A1110.

In accordance with another aspect, the present invention covers combinations of two components, component A and component B, component A being Compound A, or a tautomer, an N-oxide, a hydrate, a solvate, or a pharmaceutically acceptable salt thereof, and component B being a PD-L1 inhibitor selected from atezolizumab (Tecentriq, MPDL3280A), durvalumab (MEDI4736), avelumab (MSB0010718C), BMS-936559 (MDX1105) and LY3300054.

In accordance with another aspect, the present invention covers combinations of two components, component A and component B, component A being Compound A, or a tautomer, an N-oxide, a hydrate, a solvate, or a pharmaceutically acceptable salt thereof, and component B being atezolizumab.

In accordance with another aspect, the present invention covers combinations of two components, component A and component B, component A being Compound A, or a tautomer, an N-oxide, a hydrate, a solvate, or a pharmaceutically acceptable salt thereof, and component B being durvalumab.

In accordance with another aspect, the present invention covers combinations of two components, component A and component B, component A being Compound A, or a tautomer, an N-oxide, a hydrate, a solvate, or a pharmaceutically acceptable salt thereof, and component B being avelumab.

In accordance with another aspect, the present invention covers combinations of two components, component A and component B, component A being Compound A, or a tautomer, an N-oxide, a hydrate, a solvate, or a pharmaceutically acceptable salt thereof, and component B being BMS-936559.

In accordance with another aspect, the present invention covers combinations of two components, component A and component B, component A being Compound A, or a tautomer, an N-oxide, a hydrate, a solvate, or a pharmaceutically acceptable salt thereof, and component B being LY3300054.

In accordance with another aspect, the present invention covers a combination of any component A mentioned herein with any component B mentioned herein, optionally with any component C mentioned herein.

The combinations comprising at least two components A and B, preferably two components, as described and defined herein, are also referred to as "combinations of the present invention".

The surprising behavior of a combination of the present invention is demonstrated herein with one of the ATR kinase inhibitors ("Compound A") specifically disclosed in the Examples section.

Further, the present invention covers a kit comprising:
component A: one or more, preferably one, ATR kinase inhibitor(s) as described supra, particularly Compound A or a tautomer, an N-oxide, a hydrate, a solvate, or a pharmaceutically acceptable salt thereof;
component B: a PD-1/PD-L1 inhibitor, as described supra.

In the kit optionally either or both of said components A and B in any of the above-mentioned combinations are in the form of a pharmaceutical composition which is ready for use to be administered simultaneously, concurrently, separately or sequentially. The components A and B may be administered independently of one another by the oral, intravenous, topical, local installations, intraperitoneal or nasal route. Preferably components A and B are both administered by the oral route or component A is administered by the oral route and component B is administered by the intravenous route.

Further, the present invention covers a kit comprising:
component A: one or more, preferably one, ATR kinase inhibitor(s) as described supra, particularly Compound A or a stereoisomer, a tautomer, an N-oxide, a hydrate, a solvate, or a pharmaceutically acceptable salt thereof;
component B: a PD-1/PD-L1 inhibitor, as described supra; and, optionally,
component C: one or more, preferably one, further pharmaceutical agent(s),
in which optionally either or all of said components A, B and C in any of the above-mentioned combinations are in the form of a pharmaceutical composition which is ready for use to be administered simultaneously, concurrently, separately or sequentially. The components A and B, optionally C, may be administered independently of one another by the oral, intravenous, topical, local installations, intraperitoneal or nasal route.

In another embodiment the present invention covers a kit, in which said components A and B and optionally C each are in the form of a pharmaceutical composition and in which said component A is administered prior to component B and optionally A is administered prior to component C.

In a preferred embodiment the present invention covers a kit, in which said components A and B and optionally C each are in the form of a pharmaceutical composition and in which said component B is administered prior to component A, particularly prior to the first administration of component A, and optionally B is administered prior to component C.

In another embodiment the present invention covers a kit, in which said components A and B are in the form of two or more pharmaceutical compositions and in which said component A is administered prior to component B.

In another preferred embodiment the present invention covers a kit, in which said components A and B are in the form of two or more pharmaceutical compositions and in which said component B is administered prior to component A, particularly prior to the first administration of component A.

The term "component C" being at least one pharmaceutical agent includes the effective compound itself as well as its pharmaceutically acceptable salts, solvates, hydrates or stereoisomers as well as any pharmaceutical composition comprising such effective compound or its pharmaceutically acceptable salts, solvates, hydrates or stereoisomers. A list of such pharmaceutical agents of component C is being provided further below.

The combinations of component A and component B of this invention can be administered as the sole pharmaceutical agent or in combination with one or more further pharmaceutical agents C where the resulting combination of components A, B and C causes no unacceptable adverse effects. For example, the combinations of components A and B of this invention can be combined with component C, i.e. one or more further pharmaceutical agents, such as known anti-angiogenesis, anti-hyper-proliferative, antiinflammatory, analgesic, immunoregulatory, diuretic, antiarrhytmic, anti-hypercholsterolemia, anti-dyslipidemia, anti-diabetic or antiviral agents, and the like, as well as with admixtures and combinations thereof.

Optional pharmaceutical agents which can be added as component C to the combination of components A and B can be one or more pharmaceutical agents such as 131I-chTNT, abarelix, abiraterone, aclarubicin, adalimumab, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carbamazepine carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, Iasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, pentetreotide, nilotinib, nilutamide, nimorazole, nimotuzumab, nimustine, nintedanib, nitracrine, nivolumab, obinutuzumab, octreotide, ofatumumab, olaparib, olaratumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pembrolizumab, pemetrexed, pentazocine, pentostatin, peplomycin, perflubutane, perfosfamide, pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, rucaparib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Generally, the use of pharmaceutical agents as component C in combination with a combination of components A and B of the present invention will serve to:
(1) yield better efficacy in reducing the growth of a tumor and/or metastasis or even eliminate the tumor and/or metastasis as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Further, the present invention covers a pharmaceutical composition comprising a combination of the present invention as described herein together with one or more pharmaceutically acceptable excipients.

Further, the present invention covers a pharmaceutical composition comprising a combination of at least two components, particularly of two components, component A and component B, component A being an inhibitor of ATR kinase as described supra, particularly Compound A or a stereoisomer, a tautomer, an N-oxide, a hydrate, a solvate, or a pharmaceutically acceptable salt thereof, and component B being a PD-1/PD-L1 inhibitor, as described supra, together with one or more pharmaceutically acceptable excipients.

Further, the present invention covers a pharmaceutical composition comprising a combination of at least two components, particularly of two components, component A and component B, component A being an inhibitor of ATR kinase as described supra, particularly Compound A or a stereoisomer, a tautomer, an N-oxide, a hydrate, a solvate, or a pharmaceutically acceptable salt thereof, and component B being a PD-1/PD-L1 inhibitor, as described supra; optionally with any component C mentioned herein, together with one or more pharmaceutically acceptable excipients.

In another embodiment the components A and B, and optionally component C, are present in separate formulations. If present in separate formulations, component B is preferably administered prior to component A, particularly prior to the first administration of component A.

In another embodiment the components A and B, and optionally component C, are present in a joint formulation.

Pharmaceutically acceptable excipients are non-toxic, preferably they are non-toxic and inert. Pharmaceutically acceptable excipients include, inter alia,
fillers and excipients (for example cellulose, microcrystalline cellulose, such as, for example, Avicel®, lactose, mannitol, starch, calcium phosphate such as, for example, Di-Cafos®),
ointment bases (for example petroleum jelly, paraffins, triglycerides, waxes, wool wax, wool wax alcohols, lanolin, hydrophilic ointment, polyethylene glycols),
bases for suppositories (for example polyethylene glycols, cacao butter, hard fat)
solvents (for example water, ethanol, Isopropanol, glycerol, propylene glycol, medium chain-length triglycerides fatty oils, liquid polyethylene glycols, paraffins),
surfactants, emulsifiers, dispersants or wetters (for example sodium dodecyle sulphate, lecithin, phospholipids, fatty alcohols such as, for example, Lanette®, sorbitan fatty acid esters such as, for example, Span®, polyoxyethylene sorbitan fatty acid esters such as, for example, Tween®, polyoxyethylene fatty acid glycerides such as, for example, Cremophor®, polyoxethylene fatty acid esters, polyoxyethylene fatty alcohol ethers, glycerol fatty acid esters, poloxamers such as, for example, Pluronic®),
buffers and also acids and bases (for example phosphates, carbonates, citric acid, acetic acid, hydrochloric acid, sodium hydroxide solution, ammonium carbonate, trometamol, triethanolamine)
isotonicity agents (for example glucose, sodium chloride),
adsorbents (for example highly-disperse silicas)
viscosity-increasing agents, gel formers, thickeners and/or binders (for example polyvinylpyrrolidon, methylcellulose, hydroxypropylmethylcellulose, hydroxypropylcellulose, carboxymethylcellulose-sodium, starch, carbomers, polyacrylic acids such as, for example, Carbopol®, alginates, gelatine),
disintegrants (for example modified starch, carboxymethylcellulose-sodium, sodium starch glycolate such as, for example, Explotab®, cross-linked polyvinylpyrrolidon, croscarmellose-sodium such as, for example, AcDiSol®),
flow regulators, lubricants, glidant and mould release agents (for example magnesium stearate, stearic acid, talc, highly-disperse silicas such as, for example, Aerosil®),
coating materials (for example sugar, shellac) and film formers for films or diffusion membranes which dissolve rapidly or in a modified manner (for example polyvinylpyrrolidones such as, for example, Kollidon®, polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®),
capsule materials (for example gelatine, hydroxypropylmethylcellulose),
synthetic polymers (for example polylactides, polyglycolides, polyacrylates, polymethacrylates such as, for example, Eudragit®, polyvinylpyrrolidones such as, for example, Kollidon®, polyvinyl alcohols, polyvinyl acetates, polyethylene oxides, polyethylene glycols and their copolymers and blockcopolymers),
plasticizers (for example polyethylene glycols, propylene glycol, glycerol, triacetin, triacetyl citrate, dibutyl phthalate),
penetration enhancers,
stabilisers (for example antioxidants such as, for example, ascorbic acid, ascorbyl palmitate, sodium ascorbate, butylhydroxyanisole, butylhydroxytoluene, propyl gallate),
preservatives (for example parabens, sorbic acid, thiomersal, benzalkonium chloride, chlorhexidine acetate, sodium benzoate),
colourants (for example inorganic pigments such as, for example, iron oxides, titanium dioxide),
flavourings, sweeteners, flavour- and/or odour-masking agents.

Further excipients and procedures are described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

The components A, B and C may be administered independently of one another by the oral, intravenous, topical, local installations, intraperitoneal or nasal route.

Components A, B and C are preferably administered orally.

The pharmaceutical composition (formulation) varies by the route of administration. Components of this invention can be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

Components of this invention can also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions can be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs can be formulated with sweetening agents such as, for example, glycerol, propylene glycol, sorbitol or sucrose. Such formulations may also contain a demulcent, and preservative, such as methyl and propyl parabens and flavoring and coloring agents.

Components of this invention can also be administered parenterally, that is, subcutaneously, intravenously, intraocularly, intrasynovially, intramuscularly, or interperitoneally, as injectable dosages of the compound in preferably a pharmaceutically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions of the present invention can be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation can also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

Components of the invention can also be administered in the form of suppositories for rectal administration of the drug. These components can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It can be desirable or necessary to introduce a component of the present invention to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

In accordance with another aspect, the present invention concerns the use of the combination of the present invention as described supra for the treatment or prophylaxis of a disease, preferably a hyper-proliferative disease as described infra and/or metastases thereof, preferably metastases in bone.

In accordance with another aspect, the present invention concerns the kit as described supra for the treatment or prophylaxis of a disease, preferably a hyper-proliferative disease as described infra.

In accordance with another aspect, the present invention concerns the pharmaceutical composition as described supra for the treatment or prophylaxis of a disease, preferably a hyper-proliferative disease as described infra.

In accordance with another aspect, the present invention covers the use of such combinations as described supra for the preparation of a medicament for the treatment or prophylaxis of a disease, preferably a hyper-proliferative disease as described infra.

In accordance with another aspect, the present invention covers the use of such kit as described supra for the preparation of a medicament for the treatment or prophylaxis of a disease, preferably a hyper-proliferative disease as described infra.

In accordance with another aspect, the present invention covers the use of such pharmaceutical composition as described supra for the preparation of a medicament for the treatment or prophylaxis of a disease, preferably a hyper-proliferative disease as described infra.

In accordance with another aspect, the present invention concerns methods for the treatment and/or prophylaxis of a disease, preferably a hyper-proliferative disease as described infra, using an effective amount of the combination of the present invention as described supra.

In accordance with another aspect, the present invention concerns methods for the treatment and/or prophylaxis of a disease, preferably a hyper-proliferative disease as described infra, using an effective amount of the kit or pharmaceutical composition as described supra.

In accordance with another aspect, the present invention concerns a method of treating a disease in a patient, preferably a hyper-proliferative disease as described infra, comprising
  a) administering component A being an inhibitor of ATR kinase as described supra, particularly Compound A or a stereoisomer, a tautomer, an N-oxide, a hydrate, a solvate, or a pharmaceutically acceptable salt thereof, and
  b) administering component B being a PD-1/PD-L1 inhibitor, as described supra.

In accordance with another aspect, the present invention concerns a method of treating a disease in a patient, preferably a hyper-proliferative disease as described infra, comprising
  a) administering component A being an inhibitor of ATR kinase as described supra, particularly administering Compound A or a stereoisomer, a tautomer, an N-oxide, a hydrate, a solvate, or a pharmaceutically acceptable salt thereof, and
  b) administering component B being a PD-1/PD-L1 inhibitor, as described supra, wherein components A and B are administered simultaneously, concurrently, separately or sequentially.

In accordance with a preferred aspect, the present invention concerns a method of treating a disease in a patient, preferably a hyper-proliferative disease as described infra, comprising
  a) administering component A being an inhibitor of ATR kinase as described supra, particularly Compound A or a stereoisomer, a tautomer, an N-oxide, a hydrate, a solvate, or a pharmaceutically acceptable salt thereof, and b) administering component B being a PD-1/PD-L1 inhibitor, as described supra, wherein component B is administered prior to component A, particularly prior to Compound A, particularly prior to the first administration of Compound A.

In accordance with another aspect, the present invention concerns a method of treating a disease in a patient, preferably a hyper-proliferative disease as described infra, comprising
- a) administering Compound A or a stereoisomer, a tautomer, an N-oxide, a hydrate, a solvate, or a pharmaceutically acceptable salt thereof, and
- b) administering component B being a PD-1 inhibitor, as described supra, wherein component B is administered prior to Compound A, particularly prior to the first administration of Compound A.

In accordance with another aspect, the present invention concerns a method of treating a disease in a patient, preferably a hyper-proliferative disease as described infra, comprising
- a) administering Compound A or a stereoisomer, a tautomer, an N-oxide, a hydrate, a solvate, or a pharmaceutically acceptable salt thereof, and
- b) administering component B being a PD-1 inhibitor, wherein component B is administered prior to Compound A, particularly prior to the first administration of Compound A, and wherein component B is pembrolizumab.

In accordance with another aspect, the present invention concerns a method of treating a disease in a patient, preferably a hyper-proliferative disease as described infra, comprising
- a) administering Compound A or a stereoisomer, a tautomer, an N-oxide, a hydrate, a solvate, or a pharmaceutically acceptable salt thereof, and
- b) administering component B being a PD-L1 inhibitor, wherein component B is administered prior to Compound A, particularly prior to the first administration of Compound A, and wherein component B is spartalizumab.

In accordance with another aspect, the present invention concerns a method of treating a disease in a patient, preferably a hyper-proliferative disease as described infra, comprising
- a) administering Compound A or a stereoisomer, a tautomer, an N-oxide, a hydrate, a solvate, or a pharmaceutically acceptable salt thereof, and
- b) administering component B being a PD-L1 inhibitor, wherein component B is administered prior to Compound A, particularly prior to the first administration of Compound A, and wherein component B is JS001.

In accordance with another aspect, the present invention concerns a method of treating a disease in a patient, preferably a hyper-proliferative disease as described infra, comprising
- a) administering Compound A or a stereoisomer, a tautomer, an N-oxide, a hydrate, a solvate, or a pharmaceutically acceptable salt thereof, and
- b) administering component B being a PD-L1 inhibitor, wherein component B is administered prior to Compound A, particularly prior to the first administration of Compound A, and wherein component B is STI-A1110.

In accordance with another aspect, the present invention concerns a method of treating a disease in a patient, preferably a hyper-proliferative disease as described infra, comprising
- a) administering Compound A or a stereoisomer, a tautomer, an N-oxide, a hydrate, a solvate, or a pharmaceutically acceptable salt thereof, and
- b) administering component B being a PD-L1 inhibitor, wherein component B is administered prior to Compound A, particularly prior to the first administration of Compound A, and wherein component B is nivolumab.

In accordance with another aspect, the present invention concerns a method of treating a disease in a patient, preferably a hyper-proliferative disease as described infra, comprising
- a) administering Compound A or a stereoisomer, a tautomer, an N-oxide, a hydrate, a solvate, or a pharmaceutically acceptable salt thereof, and
- b) administering component B being a PD-L1 inhibitor, wherein component B is administered prior to Compound A, particularly prior to the first administration of Compound A, and wherein component B is durvalumab.

In accordance with another aspect, the present invention concerns a method of treating a disease in a patient, preferably a hyper-proliferative disease as described infra, comprising
- a) administering Compound A or a stereoisomer, a tautomer, an N-oxide, a hydrate, a solvate, or a pharmaceutically acceptable salt thereof, and
- b) administering component B being a PD-L1 inhibitor, wherein component B is administered prior to Compound A, particularly prior to the first administration of Compound A, and wherein component B is atezolizumab.

In accordance with another aspect, the present invention concerns a method of treating a disease in a patient, preferably a hyper-proliferative disease as described infra, comprising
- a) administering Compound A or a stereoisomer, a tautomer, an N-oxide, a hydrate, a solvate, or a pharmaceutically acceptable salt thereof, and
- b) administering component B being a PD-L1 inhibitor, wherein component B is administered prior to Compound A, particularly prior to the first administration of Compound A, and wherein component B is avelumab.

In accordance with another aspect, the present invention concerns a method of treating a disease in a patient, preferably a hyper-proliferative disease as described infra, comprising
- a) administering Compound A or a stereoisomer, a tautomer, an N-oxide, a hydrate, a solvate, or a pharmaceutically acceptable salt thereof, and
- b) administering component B being a PD-L1 inhibitor, wherein component B is administered prior to Compound A, particularly prior to the first administration of Compound A, and wherein component B is BMS-936559.

In accordance with another aspect, the present invention concerns a method of treating a disease in a patient, preferably a hyper-proliferative disease as described infra, comprising
- a) administering Compound A or a stereoisomer, a tautomer, an N-oxide, a hydrate, a solvate, or a pharmaceutically acceptable salt thereof, and
- b) administering component B being a PD-L1 inhibitor, wherein component B is administered prior to Compound A, particularly prior to the first administration of Compound A, and wherein component B is LY3300054.

In accordance with another aspect, the present invention concerns a method of treating a disease in a patient, preferably a hyper-proliferative disease as described infra comprising a) administering component A being an inhibitor of ATR kinase as described supra, particularly Compound A or a stereoisomer, a tautomer, an N-oxide, a hydrate, a solvate, or a pharmaceutically acceptable salt thereof, and b) administering component B being a PD-1/PD-L1 inhibitor, as described supra; and optionally c) administering component C being a pharmaceutical agent as described supra.

The combinations, kits or pharmaceutical compositions of the present invention thus can be used for the treatment or prophylaxis of hyper-proliferative diseases, including diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses, such as, for example, haematological tumors and/or metastases thereof, solid tumors, and/or metastases thereof, e.g. leukemias, multiple myeloma thereof and myelodysplastic syndrome, malignant lymphomas, breast tumors including and bone metastases thereof, tumors of the thorax including non-small cell and small cell lung tumors and bone metastases thereof, gastrointestinal tumors, endocrine tumors, mammary and other gynaecological tumors and bone metastases thereof, urological tumors including renal, bladder and prostate tumors, skin tumors, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Combinations, kits or pharmaceutical compositions of the present invention might be utilized to inhibit, block, reduce, decrease, etc. cell proliferation and/or cell division, and/or produce apoptosis.

This invention includes a method comprising administering to a mammal in need thereof, including a human, an amount of a component A and an amount of component B of this invention, or a pharmaceutically acceptable salt, isomer, polymorph, metabolite, hydrate, solvate or ester thereof, which is effective to treat the hyper-proliferative disease.

Hyper-proliferative diseases include but are not limited, e.g., psoriasis, keloids, and other hyperplasias affecting the skin, benign prostate hyperplasia (BPH), as well as malignant neoplasia. Examples of malignant neoplasia treatable with the compounds according to the present invention include solid and hematological tumors. Solid tumors can be exemplified by tumors of the breast, bladder, bone, brain, central and peripheral nervous system, colon, anum, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). Hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

Examples of breast cancer include, but are not limited to invasive ductal carcinoma, invasive lobular carcinoma, ductal carcinoma in situ, and lobular carcinoma in situ, particularly with bone metastases.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These diseases have been well characterized in humans, but also exist with a similar etiology in other mammals, and can be treated by administering pharmaceutical compositions of the present invention.

Combinations of the present invention might also be used for treating diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumor enlargement and metastases. Moreover, the growth of new blood and lymph vessels in a tumor provides an escape route for renegade cells, encouraging metastases and the consequence spread of the cancer. Thus, combinations of the present invention can be utilized to treat and/or prevent any of the aforementioned angiogenesis diseases, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

In another embodiment of the use of the combination/kit/pharmaceutical composition of the present invention the subject to be treated is chemotherapy-naïve.

The term "chemotherapy-naïve" as used herein means that the subject, prior to the treatment with the combination/kit/pharmaceutical composition of the present invention has not received a chemotherapy.

In another embodiment of the use of the combination/kit/pharmaceutical composition of the present invention the subject to be treated is a subject, wherein the subject has received a chemotherapy prior to the treatment with the combination/kit/pharmaceutical composition of the present invention.

The term "chemotherapy" as used herein means a category of cancer treatment that uses one or more chemotherapeutic agents as part of a standardized chemotherapy regimen. Chemotherapeutic agents are rather non-specific agents including but not limited to alkylating agents, anthracyclines, taxanes, epothilones, histone deacetylase inhibitors, inhibitors of topoisomerase I, inhibitors of topoisomerase II, nucleotide analogues, platinum-based agents, vinca alkaloids.

Dode and Administration

Component A

Based upon standard laboratory techniques known to evaluate compounds useful for the treatment of hyperproliferative diseases and angiogenic diseases, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredients to be administered in the treatment of one of these conditions can vary widely according to such considerations as the particular component and dosage unit employed, the mode of administration, the period of treatment, the age and sex of the patient treated, and the nature and extent of the condition treated. The total amount of the active ingredients to be administered will generally range from about 0.001 mg/kg to about 200 mg/kg body weight per day, and preferably from about 0.01 mg/kg to about 50 mg/kg body weight per day. Clinically useful dosing schedules of a compound will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Component B

Component B being a PD-1/PD-L1 inhibitor, as described supra, can be administered to a patient at a dosage which can range from about 1 to about 2000 mg per day. Particularly, the PD-1/PD-L1 inhibitor can be administered at a dosage of 0.005 to 10 mg/kg, preferably at a dosage of 1 to 10 mg/kg by weight of patient.

Also, the agents can be administered in conventional amounts routinely used in cancer chemotherapy. Typically, the following treatments are used:

Nivolumab: Administer as an intravenous infusion over 60 minutes.
  Unresectable or metastatic melanoma: 240 mg nivolumab every 2 weeks.
  Unresectable or metastatic melanoma: nivolumab with ipilimumab: nivolumab 1 mg/kg, followed by ipilimumab on the same day, every 3 weeks for 4 doses, then nivolumab 240 mg every 2 weeks.
  Metastatic non-small cell lung cancer: nivolumab 240 mg every 2 weeks.
  Advanced renal cell carcinoma nivolumab 240 mg every 2 weeks.
  Classical Hodgkin lymphoma: nivolumab 3 mg/kg every 2 weeks.
Pembrolizumab:
  Melanoma: 2 mg/kg every 3 weeks.
  NSCLC (=non small cell lung carcinoma): 200 mg every 3 weeks.
  HNSCC (=head and neck Squamous cell carcinoma): 200 mg every 3 weeks.
  cHL (=classical Hodgkin lymphoma): 200 mg every 3 weeks for adults; 2 mg/kg (up to 200 mg) every 3 weeks for pediatrics.
Atezolizumab: Administer 1200 mg as an intravenous infusion over 60 minutes every 3 weeks.
Durvulamab: 10 mg/kg as an intravenous infusion over 60 minutes every 2 weeks.
Avelumab: administer 10 mg/kg as an intravenous infusion over 60 minutes every 2 weeks. Premedicate with acetaminophen and an antihistamine for the first 4 infusions and subsequently as needed.

Of course the specific initial and continuing dosage regimen for each patient will vary according to the nature and severity of the condition as determined by the attending diagnostician, the activity of the specific compounds employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Suitable dose(s), administration regime(s) and administration route(s) for component B being a PD-1/PD-L1 inhibitor include those described in the NCCN Clinical Practice Guidelines in Oncology (NCCN guidelines), in particular in the NCCN Guidelines in Oncology, Version 1.2017.

Further, suitable dose(s), administration regime(s) and administration route(s) for component B may be readily determined by standard techniques known to the skilled person.

The dose(s), administration regime(s) and administration route(s) may have to be adapted according to, inter alia, the indication, the indication stage, the patient age and/or the patient gender, among other factors. Such adaptations can be readily determined by standard techniques known to the skilled person. For both, for the ATR kinase inhibitors, particularly Compound A, and for the PD-1/PD-L1 inhibitor the administered dosage of the compound(s) may be modified depending on any superior or unexpected results which may be obtained as routinely determined with this invention.

The ATR kinase inhibitor and the PD-1/PD-L1 inhibitor can be administered to a patient orally, topically, parenterally, rectally, by inhalation, and by injection. Administration by injection includes intravenous, intramuscular, subcutaneous, and parenterally as well as by infusion techniques. The agents can be administered by any of the conventional routes of administration for these compounds. The preferred route of administration for the ATR kinase inhibitor is typically orally and the PD-1/PD-L1 inhibitor is typically intravenously, which is the same route of administration used for each agent alone. Any of the PD-1/PD-L1 inhibitor described supra can be administered in combination with a compound of general formula (I) or (Ib) described supra, particularly with Compound A, by any of the mentioned routes of administration.

For administering the ATR kinase inhibitor, particularly Compound A, and the PD-1/PD-L1 inhibitor by any of the routes of administration herein discussed, the ATR kinase inhibitor, particularly Compound A, can be administered simultaneously with the PD-1/PD-L1 inhibitor. This can be performed by administering a single formulation which contains both the ATR kinase inhibitor, particularly Compound A, and the PD-1/PD-L1 inhibitor. Preferably, this can be performed by administering the ATR kinase inhibitor, particularly Compound A, and the PD-1/PD-L1 inhibitor in independent formulations at the same time to a patient.

Alternatively, the ATR kinase inhibitor described supra, particularly Compound A, can be administered in tandem with the PD-1/PD-L1 inhibitor. The ATR kinase inhibitor described supra, particularly Compound A, can be administered prior to the PD-1/PD-L1 inhibitor. For example, the ATR kinase inhibitor described supra, particularly Compound A, can be administered once or more times per day up to 28 consecutive days, or once or more times per week up to 4 consecutive weeks followed by administration of the PD-1/PD-L1 inhibitor described supra. Preferably, the PD-1/PD-L1 inhibitor as described supra is administered first followed by administration of the ATR kinase inhibitor described supra, particularly Compound A. The choice of sequence administration of the ATR kinase inhibitor described supra, particularly Compound A, relative to the PD-1/PD-L1 inhibitor may vary for different agents. Also, the PD-1/PD-L1 inhibitor described supra can be administered using any regimen which is conventionally used for these agents.

Another aspect of the invention concerns the combination, the kit or the pharmaceutical composition according to the present invention for use in the treatment or prophylaxis of a hyper-proliferative disease as described supra.

In accordance with another aspect, the present invention concerns the combination, the kit or the pharmaceutical composition according to the present invention for use in the treatment or prophylaxis of a disease, particularly of a hyper-proliferative disease as described supra, wherein components A and B are administered simultaneously, concurrently, separately or sequentially.

In accordance with another aspect, the present invention concerns the combination, the kit or the pharmaceutical composition according to the present invention for use in the treatment or prophylaxis of a disease, particularly of a hyper-proliferative disease as described supra, wherein component B is administered prior to component A, particularly prior to Compound A, particularly prior to the first administration of Compound A.

In accordance with another aspect, the present invention concerns the combination, the kit or the pharmaceutical composition according to the present invention for use in the treatment or prophylaxis of a disease, particularly of a hyper-proliferative disease as described supra, wherein component B is administered 1 day to 28 days, 7 to 28 days, 14 to 28 days, 21 to 28 days, 1 to 7 days, 7 to 14 days, 14 to 21 days, 18 to 24 days, 1 day to 21 days, 7 days to 21 days, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, or 28 days prior to the administration of component A, particularly prior to the administration of Compound A.

In accordance with another aspect, the present invention concerns the combination, the kit or the pharmaceutical composition according to the present invention for use in the treatment or prophylaxis of a disease, particularly of a hyper-proliferative disease as described supra, wherein component B is administered 1 day to 28 days, 7 to 28 days, 14 to 28 days, 21 to 28 days, 1 to 7 days, 7 to 14 days, 14 to 21 days, 18 to 24 days, 1 day to 21 days, 7 days to 21 days, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, or 28 days prior to the first administration of component A, particularly prior to the first administration of Compound A.

In another regimen of administration, the ATR kinase inhibitor described supra, particularly Compound A, and the PD-1/PD-L1 inhibitor can be administered once or more times per day on the day of administration.

Any of the routes and regimens of administration may be modified depending on any superior or unexpected results which may be obtained as routinely determined with this invention.

Figure 1A:
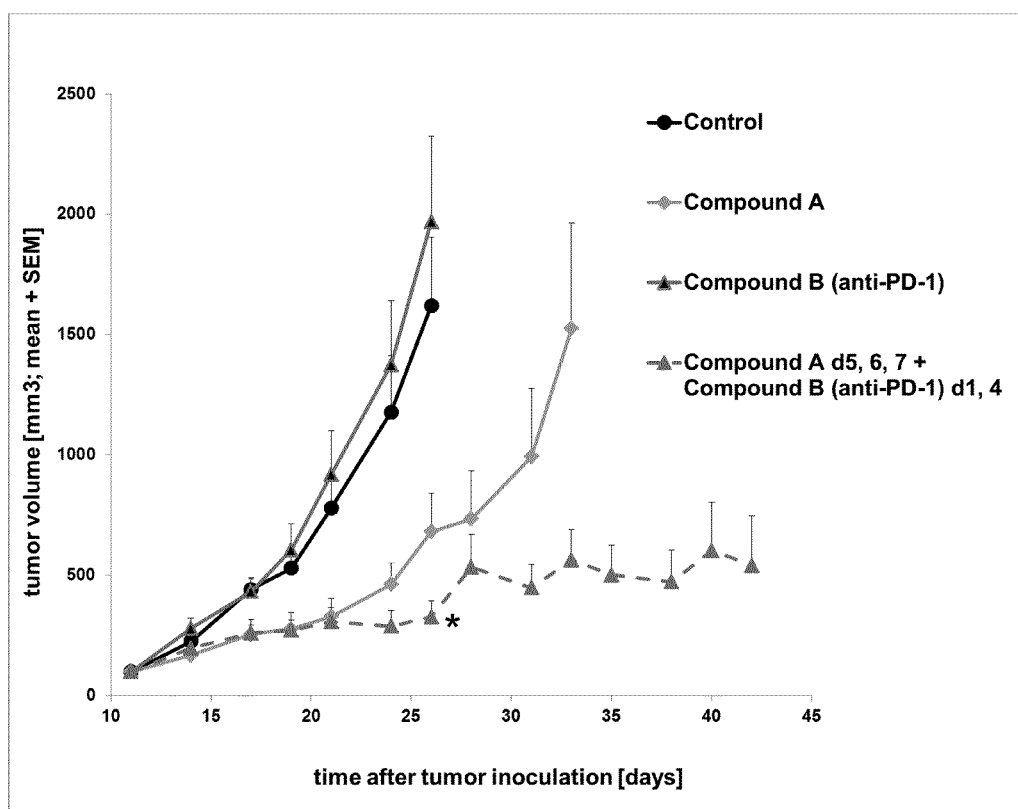
FIG. 1A shows tumor growth of the murine syngeneic lymphoma model A20 in female BALB/c mice after treatment with Compound A in combination with Compound B (=PD-1 antibody RMP1-14="anti-PD-1") (Schedule (2)) in comparison to the respective monotherapies and Control.

Legend for FIG. 1A:

Tumor growth murine B cell lymphoma A20 in BALB/c mice; *P<0.05, combination treatment compared to Control, one way ANOVA (analysis of variance), Dunn's method, on tumor volumes.

Figure 1B:
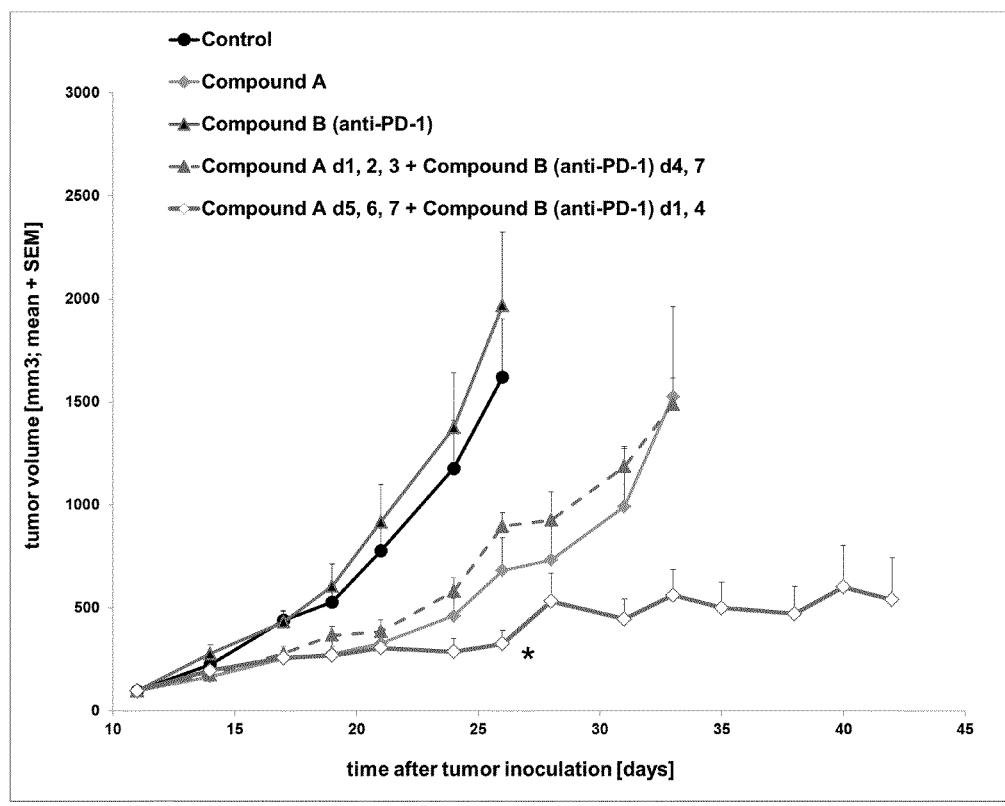

FIG. 1B shows tumor growth of the murine syngeneic lymphoma model A20 in female BALB/c mice after treatment with Compound A in combination with Compound B (=PD-1 antibody RMP1-14="anti-PD-1") upon different schedules in comparison to the respective monotherapies and Control.

Legend for FIG. 1B:

Tumor growth murine B cell lymphoma A20 in BALB/c mice; *P<0.05, combination treatment compared to Control, one way ANOVA (analysis of variance), Dunn's method, on tumor volumes.

Figure 2:
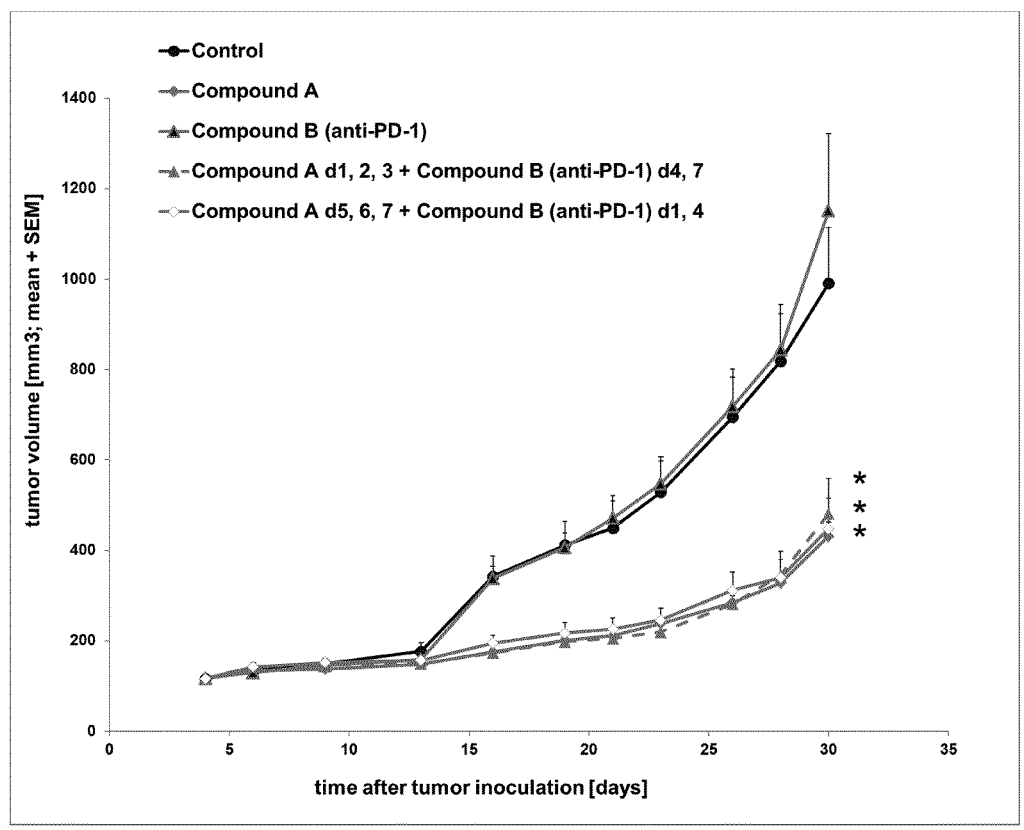

FIG. 2 shows tumor growth of the murine syngeneic lung carcinoma model KLN205 in male DBA/2 mice after treatment with Compound A in combination with Compound B (=PD-1 antibody RMP1-14="anti-PD-1") upon different schedules in comparison to the respective monotherapies and Control.

Legend for FIG. 2:

Tumor growth murine lung carcinoma model KLN205 in male DBA/2 mice; *P<0.05, treatment compared to Control, one way ANOVA (analysis of variance), Dunn's method, on tumor volumes.

Figure 3:
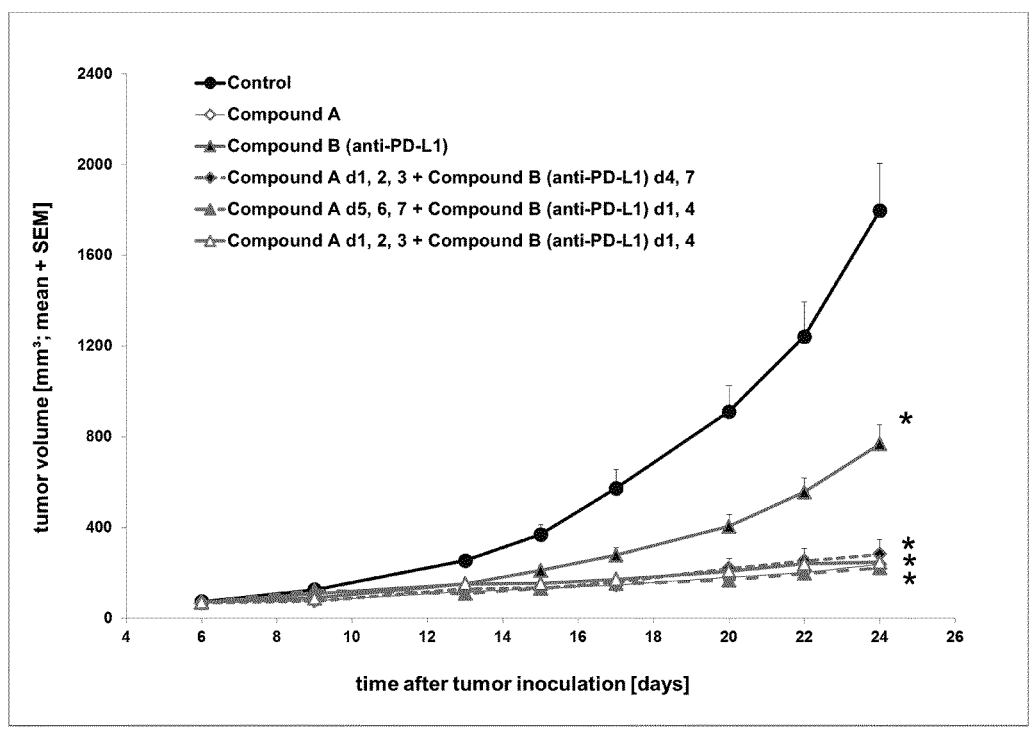

FIG. 3 shows tumor growth of the murine syngeneic colon carcinoma model MC38 in female C57BL/6N mice after treatment with Compound A in combination with Compound B (=PD-L1 antibody PPB-6721="anti-PD-L1") upon different schedules in comparison to the respective monotherapies and Control (study 1).

Legend for FIG. 3:

Tumor growth MC38 murine CRC model in C57BL/6N mice; *P<0.05, treatment compared to Control, one way ANOVA (analysis of variance), Dunn's method, on tumor volumes.

Figure 4:
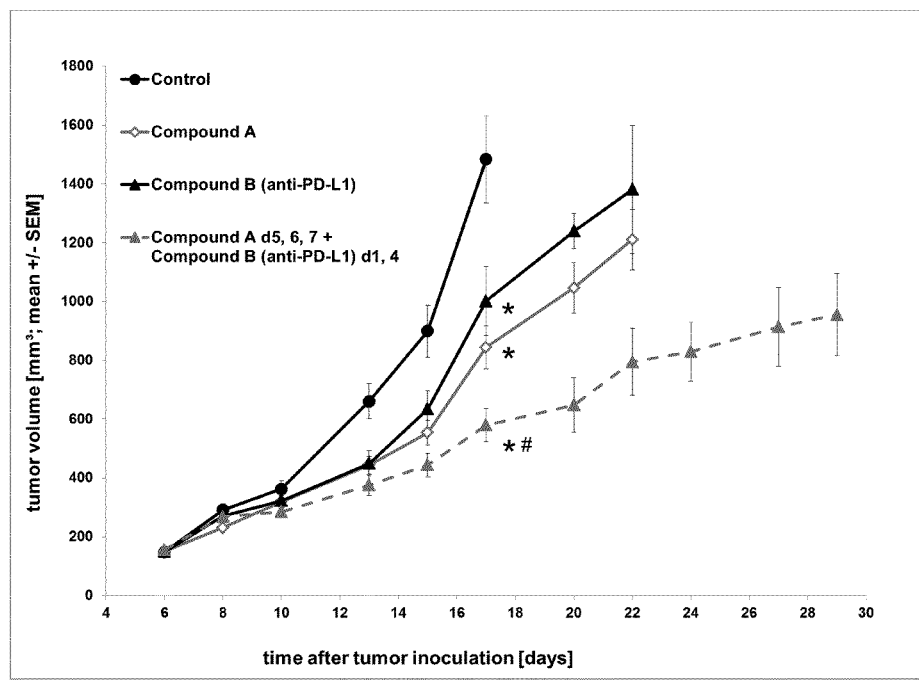

FIG. 4 shows tumor growth of the murine syngeneic colon carcinoma model MC38 in female C57BL/6N mice after treatment with Compound A in combination with Compound B (=PD-L1 antibody PPB-6721="anti-PD-L1") upon different schedules in comparison to the respective monotherapies and Control (study 2).

Legend for FIG. 4:

Tumor growth MC38 murine CRC model in C57BL/6N mice; *P<0.05, treatment compared to Control, one way ANOVA (analysis of variance), Dunn's method, on tumor volumes.

Figure 5A:
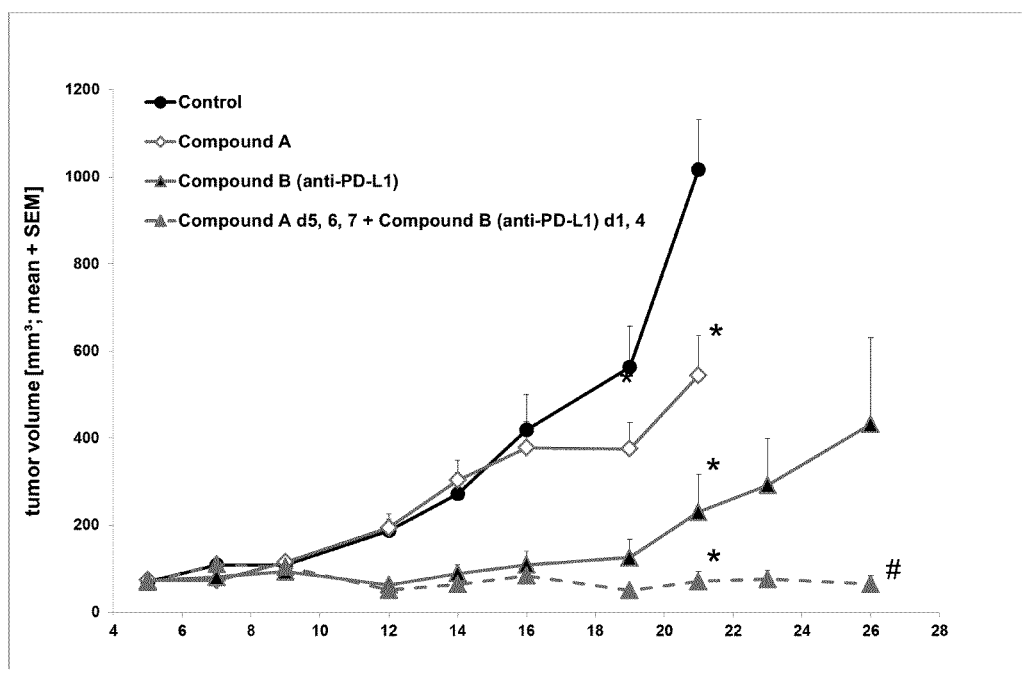

FIG. 5A shows tumor growth of the murine syngeneic colon carcinoma model CT26 in female BALB/c mice after treatment with Compound A in combination with Compound B (=PD-L1 antibody PPB-6721="anti-PD-L1") (Schedule (2)) in comparison to the respective monotherapies and Control.

Legend for FIG. 5A:

Tumor growth CT26 murine CRC model in BALB/c mice; *P<0.05, treatment compared to Control, #P<0.05, combination treatment compared to Compound B, one way ANOVA (analysis of variance), Dunn's method, on tumor volumes.

Figure 5B:
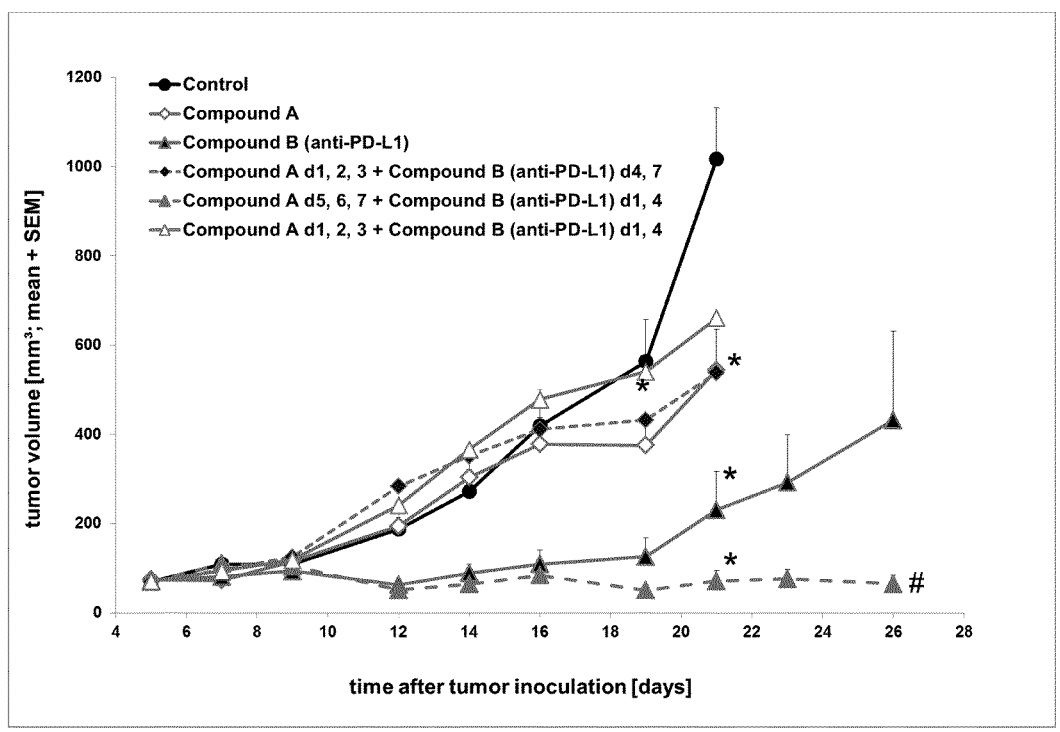

FIG. 5B shows tumor growth of the murine syngeneic colon carcinoma model CT26 in female BALB/c mice after treatment with Compound A in combination with Compound B (=PD-L1 antibody PPB-6721="anti-PD-L1") upon different schedules in comparison to the respective monotherapies and control.

Legend for FIG. 5B:

Tumor growth CT26 murine CRC model in BALB/c mice; *P<0.05, treatment compared to Control, #P<0.05, combination treatment compared to Compound B, one way ANOVA (analysis of variance), Dunn's method, on tumor volumes.

Experimental Section

Component A:

In this Experimental Section, the term "Compound A" is an example of component A.

Compound A is described in Example 111 of International Patent Application WO2016020320 (A1). As shown herein Compound A is 2-[(3R)-3-methylmorpholin-4-yl]-4-(1-methyl-1H-pyrazol-5-yl)-8-(1H-pyrazol-5-yl)-1,7-naphthyridine, of structure:

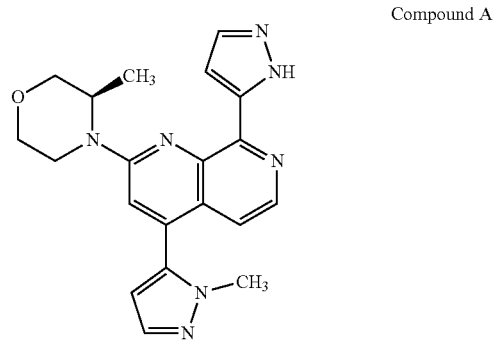 [SMILES: C[C@@H]1COCCN1c1cc(-c2ccnn2C)c2ccnc(-c3ccn[nH]3)c2n1]

Compound A

Component B:

Compound B used in the Examples below is either anti-mouse PD-1 antibody (RMP1-14; BioXcell, USA; Yamazaki et al., J Immunol, (2005) 175(3), 1586-1592) or anti-mouse PD-L1 antibody (PPB-6721, Bayer AG).

Anti-mouse PD-L1 antibody PPB-6721 was prepared as follows:

HEK293-6E cells were maintained in F17 medium (Invitrogen) supplemented with 4 mM GlutaMAX (Invitrogen), 0.1% Pluronic F-68 (Sigma) and 25 µg/ml G418 (Invitrogen). Genes encoding the antibody heavy and light chains were subcloned separately in expression vector pTT5 and co-transfected into HEK293-6E cells (Dyson and Durocher 2007). After 5-8 days of transient expression, the cleared supernatant was used to affinity purify the antibody on an Äkta System (Amersham Pharmacia Biotech) using a 10-ml HiTrap MabSelect Sure protein A column (GE Healthcare). Antibodies were eluted in two steps with 50 mM sodium acetate and 500 mM NaCl at pH 3.5 and pH 3.0. Combined elution fractions were neutralized using appropriate volumes of 2.5 M Tris base (pH>11). Aggregation products were removed by preparative size exclusion chromatography (SEC) on an Äkta Purifier System (GE Healthcare) using a custom-made Superdex™ 200 50/600 column (GE Healthcare), with a mobile phase of PBS (pH 7.4) at a flow rate of 6.0 ml/min.

Further information concerning methods for cloning, expression, and purification of anti-mouse PD-L1 antibody PPB-6721 are described in Hristodorov et al., Molecular biotechnology 53(3), (2013), 326-335.

TABLE 1

Test systems

| Cell line | Tumor entity | Mutation | Source |
|---|---|---|---|
| A20 | Lymphoma (mouse) | MSH2A733S | Crown Bioscience Inc., USA |
| KLN205 | Lung Carcinoma (mouse) | MSH2G247fs, MSH6T1100fs | Crown Bioscience Inc., USA |
| CT26 | Colon Carcinoma (mouse) | BRCA2R2066K, KRASG12D | ATCC CRL-2638 |
| MC38 | Colon Carcinoma (mouse) | ATMA2346S, MSH6T1100fs, BRAFW487C, CDKN2Adel, TRP53G242V, S258I | Bayer AG (Westhaven) |

ATCC = American Type Culture Collection

EXAMPLE 1

In Vivo Transplantation of Tumor

The anti-tumor activity of combination treatment of Compound A and Compound B (=anti-mouse PD-1 antibody or anti-mouse PD-L1 antibody) was evaluated in the murine syngeneic tumor models A20 (lymphoma), KLN205 (lung carcinoma), CT26 and MC38 (both colon carcinoma). For this purpose, female BALB/c mice from Shanghai Lingchang Bio-Technology Co. Ltd., China (A20) or from Charles River Sulzfeld, Germany (CT26) were implanted subcutaneously with A20 or CT26, male DBA/2 mice from Beijing Vital River Laboratory Animal Technology Co., Ltd. with KLN205 and female C57BL/6N mice from Charles River Sulzfeld, Germany with MC38 murine tumor cells, At a mean tumor volume of 100 mm$^3$ (A20), 117 mm$^3$ (KLN205), 70 mm$^3$ (CT26 and MC38 study 1) or 150 mm$^3$ (MC38 study 2) animals were randomized into treatment and control groups (n=8-10 animals/group) and treatment started with Compound A monotherapy (formulation: 60% PEG400, 10% Ethanol, 30% Water; application route: p.o./ peroral; dose/schedule: 50 mg/kg twice daily for 3 days on/4 days off each week), Compound B monotherapy (formulation: PBS; application route: i.v./intravenous; dose/schedule: 10 mg/kg once per day twice weekly), and combination of Compound A and Compound B at the same doses/schedules as in the respective monotherapies. Two (A20 and KLN205) or three (CT26 and MC38 study 1) or only one (MC38 study 2) different combination schedules were tested:

Schedule (1): Compound A applied on days 1, 2 and 3 each week, Compound B applied on days 4 and 7 each week;

Schedule (2): Compound A applied on days 5, 6 and 7 each week, Compound B applied on days 1 and 4 each week;

Schedule (3): Compound A applied on days 1, 2 and 3 each week, Compound B applied on days 1 and 4 each week.

The oral application volume was 10 ml/kg and the intravenous application volume 5 ml/kg. The time interval between two applications per day was 6-7 h. The tumor size and the body weight were determined three times weekly. Changes in the body weight were a measure of treatment-related toxicity (>10%=critical, stop of treatment until recovery, >20%=toxic, termination). The tumor volume was detected by means of an electronic caliper gauge [0.5×length in mm×(width in mm)$^2$]. Animals for which the tumor volume exceeded 2000 mm$^3$ (or for which the mean tumor volume of the group exceeds 2000 mm$^3$) were euthanized. In vivo anti-tumor efficacy is presented as T/C ratio (Treatment/Control) calculated with tumor volumes at day of control group termination by the formula [(tumor volume of treatment group at day x)−(tumor volume of treatment group at day before first treatment)]/[(tumor volume control group at day x)−(tumor volume of control group at day before first treatment)]. Compounds having a T/C ratio below 0.5 are defined as active (effective). Statistical analysis was assessed using SigmaStat software. A one-way analysis of variance was performed and differences to the control were compared by a pair-wise comparison procedure (Dunn's method). To evaluate the cooperativity of the combination of Compound A with Compound B expected additivity was calculated according to the Bliss model (C=A+B−A*B; wherein C is the expected T/C of the combination of drug A and drug B if they act additive, A is T/C of drug A, B is T/C of drug B). Excess>10% over the expected additive effect is assumed to indicate synergism of the two drugs, less than 10% of the expected additive effect is assumed to indicate antagonism (Bliss, C. I., The toxicity of poisons applied jointly. Ann. Appl. Biol. 26, 585-615, 1939).

Results:

In the murine syngeneic lymphoma model A20 treatment started at day 11 after tumor inoculation. Monotherapy of Compound A showed moderate anti-tumor efficacy determined at day 26 after tumor inoculation when control group was terminated due to maximal tumor size. Monotherapy of Compound B (anti-PD-1=RMP1-14) showed no anti-tumor efficacy. Combination of Compound A with Compound B in schedule (1), when Compound A was applied before Compound B, showed no effect of tumor growth inhibition. Combination treatment in schedule (2), when Compound B was applied before Compound A, showed synergistic anti-tumor efficacy at day 26 and statistically significant improvement of tumor growth inhibition in comparison to control. Treatments with Compound A alone and the two combination groups (schedules (1) and (2), respectively) of Compound A with Compound B were continued after day 26. Compound A monotherapy group as well as combination treatment group in schedule (1) were terminated on day 33 after tumor inoculation because tumors reached maximal size. Combination treatment with Compound A and Compound B in schedule (2) was further continued until day 42 after tumor inoculation, demonstrating clear tumor growth delay in comparison to respective monotherapies and control (Table 2, FIGS. 1A and 1B). Treatments were well tolerated.

TABLE 2

Anti-tumor activity of Compound A and Compound B (anti-PD-1) in monotherapy and in combination in the murine syngeneic lymphoma model A20 in female BALB/c mice.

| Substance | Dosage | T/C[a] | Excess over Bliss additivism [%] based on tumor size | Max. weight loss[b] (%) |
|---|---|---|---|---|
| Control | — | 1.00 | — | — |
| Compound A | 50 mg/kg, p.o., twice daily, 3 days on/4 days off, days 1,2, 3 each week | 0.38 | — | −2 |
| Compound B (anti-PD-1) | 10 mg/kg, i.v., once daily, twice weekly, days 1,4 each week | 1.23 | — | — |
| Schedule (1): Compound A + | 50 mg/kg, p.o., twice daily, | 0.52 | — | −4 |

TABLE 2-continued

Anti-tumor activity of Compound A and Compound B (anti-PD-1) in monotherapy and in combination in the murine syngeneic lymphoma model A20 in female BALB/c mice.

| Substance | Dosage | T/C[a] | Excess over Bliss additivism [%] based on tumor size | Max. weight loss[b] (%) |
|---|---|---|---|---|
| Compound B (anti-PD-1) | 3 days on/4 days off, days 1,2, 3 each week + 10 mg/kg, i.v., once daily, twice weekly, days 4,7 each week | | | |
| Schedule (2): Compound A + Compound B (anti-PD-1) | 50 mg/kg, p.o., twice daily, 3 days on/4 days off, days 5,6, 7 each week + 10 mg/kg, i.v., once daily, twice weekly, days 1,4 each week | 0.15* | 60 | −4 |

*P < 0.05 (compared to control at day 26 after tumor inoculation)
[a]T/C = ratio of the tumor volume of treatment versus control at day of control termination [(tumor volume of treatment group at day x) − (tumor volume of treatment group at day before first treatment)]/[(tumor volume control group at day x) − (tumor volume of control group at day before first treatment)].
[b]Loss of body weight: Changes in body weight compared to the initial body weight at the start of treatment (>10% = critical, stoppage in treatment until recovery, >20% = toxic, termination).
The abbreviation p.o. means peroral, i.v. means intravenous In the murine syngeneic lung carcinoma model KLN205 treatment started at day 4 after tumor inoculation. Monotherapy of Compound A showed moderate anti-tumor efficacy determined at day 30 after tumor inoculation when control group was terminated due to maximal tumor size. Monotherapy of Compound B (anti-PD-1=RMP1-14) showed no anti-tumor efficacy. Combination of Compound A with Compound B did not improve anti-tumor efficacy achieved by Compound A alone in the tested combination treatment schedules (1) and (2). Due to critical body weight loss in groups treated with Compound A alone or in combination with Compound B, Compound A has been applied upon reduced dose (40 mg/kg) from day 18 after tumor inoculation (Table 3, FIG. 2).

TABLE 3

Anti-tumor activity of Compound A and Compound B (anti-PD-1) in monotherapy and in combination in the murine syngeneic lung carcinoma model KLN205 in male DBA/2 mice.

| Substance | Dosage | T/C[a] | Excess over Bliss additivism [%] based on tumor size | Max. weight loss[b] (%) |
|---|---|---|---|---|
| Control | — | 1.00 | — | −7 |
| Compound A | 50/40(d 18) mg/kg, p.o., twice daily, 3 days on/4 days off, days 1,2,3 each week | 0.36* | — | −19 (d9) |
| Compound B (anti-PD-1) | 10 mg/kg, i.v., once daily, twice weekly, days 1,4 each week | 1.18 | — | −5 |
| Schedule (1): Compound A + Compound B (anti-PD-1) | 50/40(d 18) mg/kg, p.o., twice daily, 3 days on/4 days off, days 1,2,3 each week + 10 mg/kg, i.v., once daily, twice weekly, days 4,7 each week | 0.42* | — | −20 (d9) |
| Schedule (2): Compound A + Compound B (anti-PD-1) | 50/40(d 18) mg/kg, p.o., twice daily, 3 days on/4 days off, days 5,6,7 each week + 10 mg/kg, i.v., once daily, twice weekly, days 1,4 each week | 0.38* | — | −20 (d13) |

*P < 0.05 (compared to Control at day 30 after tumor inoculation)
[a]T/C = ratio of the tumor volume of treatment versus control at day of control termination [(tumor volume of treatment group at day x) − (tumor volume of treatment group at day before first treatment)]/[(tumor volume control group at day x) − (tumor volume of control group at day before first treatment)].
[b]Loss of body weight: Changes in body weight compared to the initial body weight at the start of treatment (>10% = critical, stoppage in treatment until recovery, >20% = toxic, termination).
The abbreviation d means day (after tumor inoculation), p.o. means peroral, i.v. means intravenous In the murine syngeneic colorectal carcinoma model MC38 two studies have been performed. In MC38 study 1, treatment started at day 6 after tumor inoculation at a tumor size of 70 mm³. Monotherapy of Compound A showed good anti-tumor efficacy and statistically significant improvement of tumor growth inhibition compared to control at day 24 after tumor inoculation, when control treatment group was terminated due to maximal tumor size. Monotherapy of Compound B (anti-PD-L1=PPB-6721) showed moderate anti-tumor efficacy at day 24 with statistically significant improvement of tumor growth inhibition in comparison to control. Combination of Compound A with Compound B did not enhance anti-tumor efficacy achieved by Compound A monotherapy in all tested schedules (1), (2) and (3) in this study. Treatments were well tolerated (Table 4, FIG. 3).

TABLE 4

Anti-tumor activity of Compound A and Compound B (anti-PD-L1) in monotherapy and in combination in the murine syngeneic colon carcinoma model MC38 in female C57BL/6N mice (MC38 study 1).

| Substance | Dosage | T/C[a] | Excess over Bliss additivism [%] based on tumor size | Max. weight loss[b] (%) |
|---|---|---|---|---|
| Control | — | 1.00 | — | — |
| Compound A | 50 mg/kg, p.o., twice daily, 3 days on/4 days off, days 1,2,3 each week | 0.10* | — | −3 |

TABLE 4-continued

Anti-tumor activity of Compound A and Compound
B (anti-PD-L1) in monotherapy and in combination
in the murine syngeneic colon carcinoma model
MC38 in female C57BL/6N mice (MC38 study 1).

| Substance | Dosage | T/C$^a$ | Excess over Bliss additivism [%] based on tumor size | Max. weight loss$^b$ (%) |
|---|---|---|---|---|
| Compound B (anti-PD-L1) | 10 mg/kg, i.v., once daily, twice weekly, days 1,4 each week | 0.41* | — | −4 |
| Schedule (1) Compound A + Compound B (anti-PD-L1) | 50 mg/kg, p.o., twice daily, 3 days on/4 days off, days 1,2,3 each week + 10 mg/kg, i.v., once daily, twice weekly, days 4,7 each week | 0.12* | — | −4 |
| Schedule (2) Compound A + Compound B (anti-PD-L1) | 50 mg/kg, p.o., twice daily, 3 days on/4 days off, days 5,6,7 each week + 10 mg/kg, i.v., once daily, twice weekly, days 1,4 each week | 0.09* | — | −6 |
| Schedule (3) Compound A + Compound B (anti-PD-L1) | 50 mg/kg, p.o., twice daily, 3 days on/4 days off, days 1,2,3 each week + 10 mg/kg, i.v., once daily, twice weekly, days 1,4 each week | 0.10* | — | −6 |

*P < 0.05 (compared to Control at day 24 after tumor inoculation)
$^a$T/C = ratio of the tumor volume of treatment versus control at day of control termination [(tumor volume of treatment group at day x) − (tumor volume of treatment group at day before first treatment)]/[(tumor volume control group at day x) − (tumor volume of control group at day before first treatment)].
$^b$Loss of body weight: Changes in body weight compared to the initial body weight at the start of treatment (>10% = critical, stoppage in treatment until recovery, >20% = toxic, termination).
The abbreviation p.o. means peroral, i.v. means intravenous.

In MC38 study 2, treatment started also at day 6 after tumor inoculation but at a tumor size of 150 mm$^3$. Monotherapy of Compound A showed moderate anti-tumor efficacy and statistically significant improvement of tumor growth inhibition compared to control at day 17 after tumor inoculation, when control treatment group was terminated due to maximal tumor size. Monotherapy of Compound B (anti-PD-L1=PPB-6721) showed moderate to weak anti-tumor efficacy at day 17 with statistically significant improvement of tumor growth inhibition in comparison to control. Remarkably, in contrast to MC38 study 1, in this study combination of Compound A with Compound B in schedule (2) did significantly enhance anti-tumor efficacy achieved by Compound A or Compound B monotherapy, which is probably due to treatment start at larger tumor size. Treatments were well tolerated (Table 5, FIG. 4).

TABLE 5

Anti-tumor activity of Compound A and Compound
B (anti-PD-L1) in monotherapy and in combination
in the murine syngeneic colon carcinoma model
MC38 in female C57BL/6N mice (MC38 study 2).

| Substance | Dosage | T/C$^a$ | Excess over Bliss additivism [%] based on tumor size | Max. weight loss$^b$ (%) |
|---|---|---|---|---|
| Control | — | 1.00 | — | −3 |
| Compound A | 50 mg/kg, p.o., twice daily, 3 days on/4 days off, days 1,2,3 each week | 0.46* | — | −5 |
| Compound B (anti-PD-L1) | 10 mg/kg, i.v., once daily, twice weekly, days 1,4 each week | 0.78* | — | −3 |
| Schedule (2) Compound A + Compound B (anti-PD-L1) | 50 mg/kg, p.o., twice daily, 3 days on/4 days off, days 5,6,7 each week + 10 mg/kg, i.v., once daily, twice weekly, days 1,4 each week | 0.33* | 4 | −4 |

*P < 0.05 (compared to Control at day 17 after tumor inoculation)
$^a$T/C = ratio of the tumor volume of treatment versus control at day of control termination [(tumor volume of treatment group at day x) − (tumor volume of treatment group at day before first treatment)]/[(tumor volume control group at day x) − (tumor volume of control group at day before first treatment)].
$^b$Loss of body weight: Changes in body weight compared to the initial body weight at the start of treatment (>10% = critical, stoppage in treatment until recovery, >20% = toxic, termination).
The abbreviation p.o. means peroral, i.v. means intravenous.

In the murine syngeneic colorectal carcinoma model CT26 monotherapy of Compound A showed moderate anti-tumor efficacy but statistically significant improvement of tumor growth inhibition compared to control at day 21 after tumor inoculation, when control and Compound A treatment group were terminated due to maximal tumor size. Monotherapy of Compound B (anti-PD-L1=PPB-6721) showed good anti-tumor efficacy at day 21 with statistically significant improvement of tumor growth inhibition in comparison to control. Combination of Compound A with Compound B in schedule (2), when Compound B was applied before Compound A, enhanced anti-tumor efficacy of Compound B monotherapy at day 21, demonstrating synergistic anti-tumor activity of Compound A and Compound B in this combination schedule. Treatments of groups with Compound B alone and the combination of Compound A with Compound B in schedule (2) were continued until study termination at day 26 after tumor inoculation. Prolonged combination treatment of Compound A with Compound B in schedule (2) achieved strong and continuous tumor growth inhibition, as shown by statistically significant improvement of anti-tumor efficacy in comparison to Compound B alone, determined at day 26 after tumor inoculation (Table 6). In contrast, combination of Compound A with Compound B in schedules (1) and (3), when Compound A was applied before Compound B (schedule (1)) or when Compound A and Compound B were applied at the same time (schedule (3)), did not show any synergy, but rather a reduction of anti-tumor activity that is achieved by Compound B alone (FIGS. 5A and 5B).-Both groups (schedules (1) and (3), respectively) were terminated at day 21 after tumor inoculation, due to maximal tumor size. Treatments were well tolerated.

TABLE 6

Anti-tumor activity of Compound A and Compound B (anti-PD-L1) in monotherapy and in combination in the murine syngeneic colon carcinoma model CT26 in female BALB/c mice.

| Substance | Dosage | T/C$^a$ | Excess over Bliss additivism [%] based on tumor size | Max. weight loss$^b$ (%) |
|---|---|---|---|---|
| Control | — | 1.00 | — | — |
| Compound A | 50 mg/kg, p.o., twice daily, 3 days on/4 days off, days 1,2,3 each week | 0.50* | — | −1 |
| Compound B (anti-PD-L1) | 10 mg/kg, i.v., once daily, twice weekly, days 1,4 each week | 0.17* | — | — |
| Schedule (1) Compound A + Compound B (anti-PD-L1) | 50 mg/kg, p.o., twice daily, 3 days on/4 days off, days 1,2,3 each week + 10 mg/kg, i.v., once daily, twice weekly, days 4,7 each week | 0.49 | — | −1 |
| Schedule (2) Compound A + Compound B (anti-PD-L1) | 50 mg/kg, p.o., twice daily, 3 days on/4 days off, days 5,6,7 each week + 10 mg/kg, i.v., once daily, twice weekly, days 1,4 each week | 0.00*# | 9 | −1 |
| Schedule (3) Compound A + Compound B (anti-PD-L1) | 50 mg/kg, p.o., twice daily, 3 days on/4 days off, days 1,2,3 each week + 10 mg/kg, i.v., once daily, twice weekly, days 1,4 each week | 0.62 | — | −1 |

*P < 0.05 (compared to Control at day 21 after tumor inoculation)
P < 0.05 (compared to Compound B monotherapy at termination day 26 after tumor inoculation)
$^a$T/C = ratio of the tumor volume of treatment versus control at day of control termination [(tumor volume of treatment group at day x) − (tumor volume of treatment group at day before first treatment)]/[(tumor volume control group at day x) − (tumor volume of control group at day before first treatment)].
$^b$Loss of body weight: Changes in body weight compared to the initial body weight at the start of treatment (>10% = critical, stoppage in treatment until recovery, >20% = toxic, termination).
The abbreviation p.o. means peroral, i.v. means intravenous.

The invention claimed is:

1. A method for treatment of a hyper-proliferative disease that is a cancer, comprising administering to a patient in need thereof, an effective amount of a combination-comprising at least two components, component A and component B, wherein component A is an inhibitor of ATR kinase having the structure:

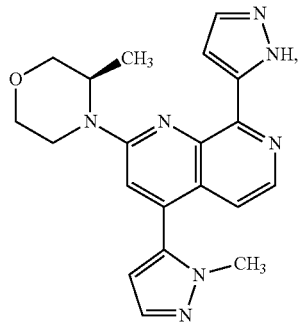 [SMILES: C[C@@H]1COCCN1c1cc(-c2ccnn2C)c2ccnc(-c3ccn[nH]3)c2n1]

or a stereoisomer, a tautomer, an N-oxide, a hydrate, a solvate, or a pharmaceutically acceptable salt thereof; and wherein component B is a PD-1 inhibitor or a PD-L1 inhibitor, and wherein component B is administered to the patient prior to the first administration of component A.

2. The method according to claim 1, wherein component B is a PD-1 inhibitor.

3. The method according to claim 2, wherein the PD-1 inhibitor of component B is selected from the group consisting of nivolumab, pembrolizumab, PDR-001, JS001, STI-A1110, atezolizumab, durvalumab, avelumab, BMS-936559 and LY3300054.

4. The method according to claim 3, wherein the PD-1 inhibitor of component B is pembrolizumab.

5. The method according to claim 1, wherein component B is a PD-L1 inhibitor.

6. The method combination according to claim 5, wherein the PD-L1 inhibitor of component B is selected from the group consisting of nivolumab, pembrolizumab, atezolizumab, durvalumab and avelumab.

7. The method according to claim 6, wherein the PD-L1 inhibitor of component B is atezolizumab.

8. The method according to claim 1, wherein the hyper-proliferative disease is lymphoma, lung carcinoma or colon carcinoma.

9. The method according to claim 1, wherein the hyper-proliferative disease is lung carcinoma.

10. The method according to claim 1, wherein the hyper-proliferative disease is colon carcinoma.

11. The method according to claim 1, wherein the hyper-proliferative disease is lymphoma.

12. The method according to claim 1, wherein either or both of said components A and B are in the form of a pharmaceutical composition.

13. The method according to claim 12, wherein the pharmaceutical composition comprises one or more pharmaceutically acceptable excipients.

14. The method according to claim 1, wherein the components A and B are present in separate formulations.

15. The method according to claim 1 wherein the combination further comprises a component C, wherein component C is one or more further pharmaceutical agents.

* * * * *

UNITED STATES PATENT AND TRADEMARK OFFICE
CERTIFICATE OF CORRECTION

PATENT NO. : 11,690,911 B2
APPLICATION NO. : 16/635812
DATED : July 4, 2023
INVENTOR(S) : Wengner Page 1 of 2

It is certified that error appears in the above-identified patent and that said Letters Patent is hereby corrected as shown below:

In the Drawings

In Fig. 1A, Sheet 1 of 7, and on the title page, the illustrative print figure, delete "[mm3;" and insert -- [mm$^3$; --, therefor.
In Fig. 1B, Sheet 2 of 7, delete "[mm3;" and insert -- [mm$^3$; --, therefor.
In Fig. 2, Sheet 3 of 7, delete "[mm3;" and insert -- [mm$^3$; --, therefor.
In Fig. 5A, Sheet 6 of 7, delete "4  6  8  10  12  14  16  18  20  22  24  26  28" and insert -- 4  6  8  10  12  14  16  18  20  22  24  26  28  time after tumor inoculation [days] --, therefor.

In the Specification

In Column 2, Line 39, delete "most" and insert -- is most --, therefor.
In Column 5, Line 54, delete "in identically" and insert -- identically --, therefor.
In Column 6, Line 13, delete "in identically" and insert -- identically --, therefor.
In Column 9, Line 48, delete "$^{32}$PF," and insert -- $^{32}$P, --, therefor.
In Column 12, Line 18, delete "limited" and insert -- limited to --, therefor.
In Column 12, Line 31, delete "a" and insert -- A --, therefor.
In Column 17, Line 15, delete "(methylsulfonyflpyridin" and insert -- (methylsulfonyl)pyridin --, therefor.
In Column 17, Line 21, delete "(methylsulfonyflpyridin" and insert -- (methylsulfonyl)pyridin --, therefor.
In Column 17, Line 42, delete "(methylsulfonyflpyridin" and insert -- (methylsulfonyl)pyridin --, therefor.
In Column 19, Line 26, delete "(methylsulfonyflpyridin" and insert -- (methylsulfonyl)pyridin --, therefor.
In Column 32, Line 26, delete "Component of the Combination" and insert -- Component B of the Combination --, therefor.

Signed and Sealed this
Second Day of April, 2024

Katherine Kelly Vidal
*Director of the United States Patent and Trademark Office*

In Column 43, Line 10, delete "form" and insert -- from --, therefor.
In Column 49, Line 17, delete "consequence" and insert -- consequent --, therefor.
In Column 49, Line 48, delete "Dode" and insert -- Dose --, therefor.

In the Claims

In Column 62, Line 58, in Claim 15, delete "claim 1" and insert -- claim 1, --, therefor.